(12) United States Patent
Watabe et al.

(10) Patent No.: US 9,991,471 B2
(45) Date of Patent: Jun. 5, 2018

(54) LIGHT-EMITTING ELEMENT, LIGHT-EMITTING DEVICE, DISPLAY DEVICE, AND ELECTRONIC DEVICE

(71) Applicant: Semiconductor Energy Laboratory Co., Ltd., Kanagawa-ken (JP)

(72) Inventors: Takeyoshi Watabe, Kanagawa (JP); Toshiki Sasaki, Kanagawa (JP); Satoshi Seo, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 196 days.

(21) Appl. No.: 14/978,034

(22) Filed: Dec. 22, 2015

(65) Prior Publication Data

US 2016/0190500 A1 Jun. 30, 2016

(30) Foreign Application Priority Data

Dec. 26, 2014 (JP) ................. 2014-264945

(51) Int. Cl.
| | |
|---|---|
| *C09K 11/00* | (2006.01) |
| *H01L 51/52* | (2006.01) |
| *C07F 15/00* | (2006.01) |
| *C09K 11/06* | (2006.01) |
| *H01L 51/50* | (2006.01) |

(Continued)

(52) U.S. Cl.
CPC ...... *H01L 51/5265* (2013.01); *C07F 15/0033* (2013.01); *C09K 11/06* (2013.01); *H01L 51/5016* (2013.01); *H01L 27/323* (2013.01); *H01L 51/006* (2013.01); *H01L 51/0059* (2013.01); *H01L 51/0072* (2013.01); *H01L 51/0074* (2013.01); *H01L 51/0085* (2013.01); *H01L 2251/5384* (2013.01)

(58) Field of Classification Search
CPC .......... H01L 2251/5384; H01L 27/323; H01L 51/5016; H01L 51/5265; C09K 11/06; C07F 15/0033
USPC ...................................... 257/40, 89
See application file for complete search history.

(56) References Cited

U.S. PATENT DOCUMENTS

| | | |
|---|---|---|
| 7,129,634 B2 | 10/2006 | Boroson et al. |
| 7,291,969 B2 | 11/2007 | Tsutsui |
| 7,906,226 B2 | 3/2011 | Matsuura et al. |

(Continued)

FOREIGN PATENT DOCUMENTS

| | | |
|---|---|---|
| JP | 2001-33732 | 12/2001 |
| JP | 2010-182699 | 8/2010 |

*Primary Examiner* — Amanda C Walke
(74) *Attorney, Agent, or Firm* — Husch Blackwell LLP

(57) ABSTRACT

A light-emitting element that emits light with high color purity, a light-emitting element that emits light at high emission efficiency, or a light-emitting element with reduced power consumption. The light-emitting element includes a first electrode, a second electrode, and an EL layer. The first electrode is configured to reflect light. The second electrode is configured to reflect light and transmit light. The EL layer is between the first electrode and the second electrode. The EL layer includes a guest material. The guest material is configured to convert triplet excitation energy into light emission. The emission spectrum of the guest material in a dichloromethane solution has a peak in a wavelength region ranging from 440 nm to 470 nm and has a full width at half maximum of greater than or equal to 20 nm and less than or equal to 80 nm.

20 Claims, 42 Drawing Sheets

(51) Int. Cl.
*H01L 27/32* (2006.01)
*H01L 51/00* (2006.01)

(56) References Cited

U.S. PATENT DOCUMENTS

| | | | |
|---|---|---|---|
| 8,633,473 B2 | 1/2014 | Noda et al. | |
| 2007/0164285 A1* | 7/2007 | Nakamura | H01L 51/002 257/59 |
| 2008/0093981 A1* | 4/2008 | Nakamura | C09K 11/06 313/504 |
| 2013/0161598 A1 | 6/2013 | Inoue et al. | |
| 2013/0187166 A1* | 7/2013 | Yamazaki | H01L 27/12 257/66 |
| 2013/0228765 A1* | 9/2013 | Nakashima | C07D 209/88 257/40 |
| 2013/0256637 A1* | 10/2013 | Seo | H01L 51/5004 257/40 |
| 2013/0320368 A1* | 12/2013 | Seo | H01L 27/3206 257/89 |
| 2014/0034927 A1* | 2/2014 | Seo | H01L 51/504 257/40 |
| 2014/0159097 A1* | 6/2014 | Yamazaki | H01L 33/504 257/98 |
| 2014/0291645 A1* | 10/2014 | Inoue | C07D 491/048 257/40 |
| 2015/0243918 A1* | 8/2015 | Sasaki | H01L 51/5016 257/40 |
| 2016/0079314 A1* | 3/2016 | Seo | H01L 51/0054 257/40 |

* cited by examiner

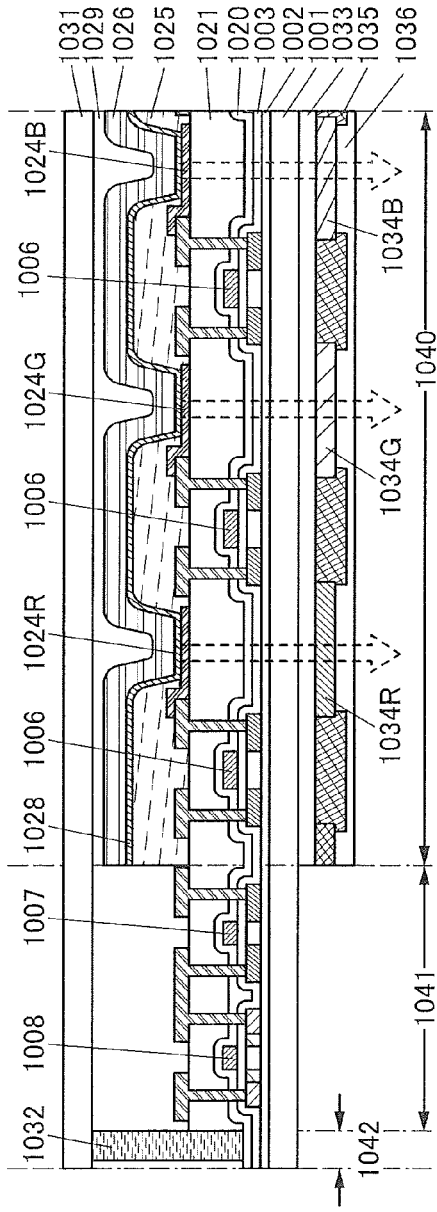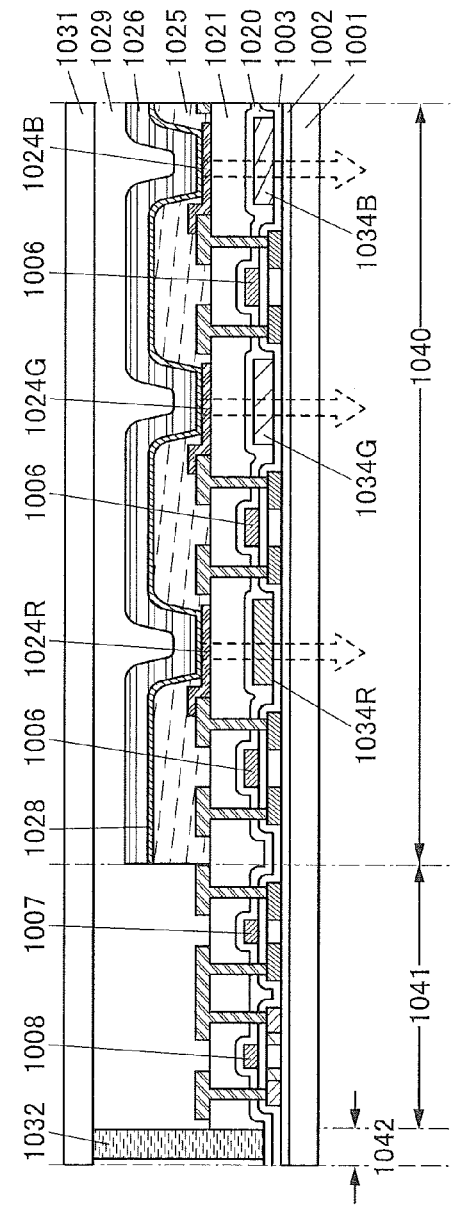

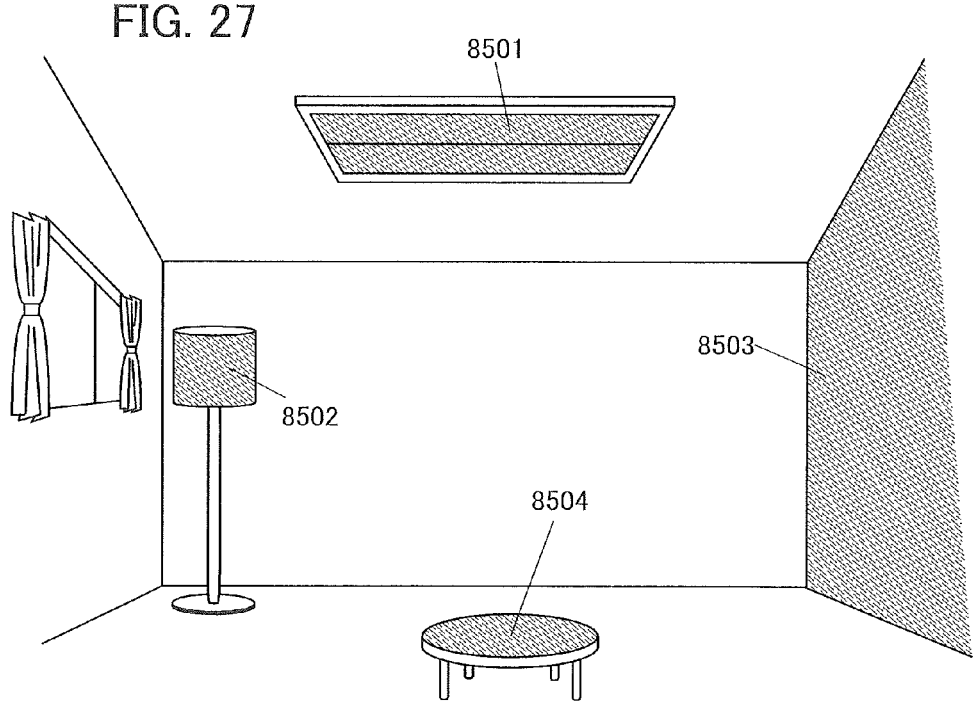

LIGHT-EMITTING ELEMENT, LIGHT-EMITTING DEVICE, DISPLAY DEVICE, AND ELECTRONIC DEVICE

BACKGROUND OF THE INVENTION

1. Field of the Invention

One embodiment of the present invention relates to a light-emitting element, a light-emitting device including the light-emitting element, a display device including the light-emitting element, an electronic device including the light-emitting element, and the like.

Note that one embodiment of the present invention is not limited to the above technical field. The technical field of one embodiment of the invention disclosed in this specification and the like relates to an object, a method, or a manufacturing method. One embodiment of the present invention relates to a process, a machine, manufacture, or a composition of matter. Specifically, examples of the technical field of one embodiment of the present invention disclosed in this specification include a semiconductor device, a display device, a liquid crystal display device, a light-emitting device, a lighting device, a power storage device, a memory device, a method for driving any of them, and a method for manufacturing any of them.

2. Description of the Related Art

In recent years, research and development have been extensively conducted on light-emitting elements utilizing electroluminescence (EL). In a basic structure of these light-emitting elements, a layer containing a light-emitting substance (an EL layer) is provided between a pair of electrodes. By application of a voltage between the electrodes of this element, light emission from the light-emitting substance can be obtained.

Since the above light-emitting element is a self-luminous type, a light-emitting device using this light-emitting element has advantages such as high visibility, no necessity of a backlight, and low power consumption. The light-emitting device using the light-emitting element also has advantages in that it can be manufactured to be thin and lightweight and has high response speed.

In a light-emitting element (e.g., an organic EL element) whose EL layer contains an organic compound as a light-emitting substance and is provided between a pair of electrodes, application of a voltage between the pair of electrodes causes injection of electrons from a cathode and holes from an anode into the EL layer having a light-emitting property and thus a current flows. By recombination of the injected electrons and holes, the organic compound having a light-emitting property is brought into an excited state to provide light emission.

Note that an excited state formed by an organic compound can be a singlet excited state (S*) or a triplet excited state (T*). Light emission from the singlet-excited state is referred to as fluorescence, and light emission from the triplet excited state is referred to as phosphorescence. The formation ratio of S* to T* in the light-emitting element is statistically considered to be 1:3. In other words, a light-emitting element containing a compound emitting phosphorescence (a phosphorescent compound) has higher emission efficiency than a light-emitting element containing a compound emitting fluorescence (a fluorescent compound). Therefore, light-emitting elements including phosphorescent compounds capable of converting a triplet excited state into light emission has been actively developed in recent years (for example, see Patent Document 1).

The light-emitting element can emit light of a variety of colors depending on the kind of light-emitting substance included in the EL layer. A light-emitting element which can emit white light or light of color close to white with high efficiency has been particularly required to be applied to a lighting and a display device utilizing the white EL+color filter method. In addition, a light-emitting element having low power consumption is required.

[Patent Document 1] Japanese Published Patent Application No. 2010-182699

SUMMARY OF THE INVENTION

For reducing power consumption of a light-emitting device or display device including the light-emitting element, it is important to enhance the emission efficiency of a light-emitting element, especially a light-emitting element emitting blue light. It is also important to increase the color purity of the light-emitting element emitting blue light.

In view of the above-described problems, an object of one embodiment of the present invention is to provide a novel light-emitting element. Another object is to provide a novel light-emitting element emitting light with high color purity. Another object is to provide a novel light-emitting element having high emission efficiency. Another object is to provide a novel light-emitting element with low power consumption. Another object is to provide a method for fabricating a novel light-emitting element.

Note that the descriptions of the above objects do not disturb the existence of other objects. In one embodiment of the present invention, there is no need to achieve all the objects. Other objects will be apparent from and can be derived from the descriptions of the specification and the like.

One embodiment of the present invention is a light-emitting element including a first electrode, a second electrode, and an EL layer. The first electrode is configured to reflect light. The second electrode is configured to reflect light and transmit light. The EL layer is between the first electrode and the second electrode, and includes a first guest material. The first guest material is configured to convert triplet excitation energy into light emission. The emission spectrum of the first guest material in a dichloromethane solution has a maximum value (a peak) in a wavelength region ranging from 440 nm to 470 nm and has a full width at half maximum of greater than or equal to 20 nm and less than or equal to 80 nm.

Another embodiment of the present invention is a light-emitting element including a first electrode, a second electrode, a first EL layer, a second EL layer, and a charge-generation layer. The first electrode is configured to reflect light. The second electrode is configured to reflect light and transmit light. The first EL layer, the second EL layer, and the charge-generation layer are between the first electrode and the second electrode. The first EL layer includes a first guest material. The first guest material is configured to convert triplet excitation energy into light emission. The emission spectrum of the first guest material in a dichloromethane solution has a maximum value (a peak) in a wavelength region ranging from 440 nm to 470 nm and has a full width at half maximum of greater than or equal to 20 nm and less than or equal to 80 nm.

In each of the above structures, the light intensity of the first guest material in the dichloromethane solution at a wavelength of 530 nm is preferably greater than or equal to 0% and less than or equal to 50% of the maximum value.

In each of the above structures, the chromaticity y in CIE 1931 chromaticity coordinates of the first guest material is preferably greater than or equal to 0.01 and less than or equal to 0.3. The chromaticity y is calculated from an emission spectrum of the first guest material in the dichloromethane solution.

Each of the light-emitting elements with the above structures preferably emits light whose chromaticity y in CIE 1931 chromaticity coordinates is greater than or equal to 0.01 and less than or equal to 0.06 at a current efficiency greater than or equal to 3 cd/A.

Each of the light-emitting elements with the above structures preferably emits light whose chromaticity y in CIE 1931 chromaticity coordinates is greater than 0.06 and less than or equal to 0.08 at a current efficiency greater than or equal to 8 cd/A.

Each of the light-emitting elements with the above structures preferably emits light whose chromaticity y in CIE 1931 chromaticity coordinates is greater than 0.08 and less than or equal to 0.1 at a current efficiency greater than or equal to 10 cd/A.

In each of the above structures, it is preferable that the second EL layer include a second guest material, and that the emission spectrum of the second guest material have a maximum value (a peak) in any one of a green wavelength region, a yellow-green wavelength region, a yellow wavelength region, an orange wavelength region, and a red wavelength region.

In each of the above structure, the second guest material is preferably configured to convert triplet excitation energy into light emission.

In each of the above structures, the first guest material preferably includes iridium.

In the above structure, it is preferable that the first guest material include a ligand coordinated to the iridium, and that the ligand include a nitrogen-containing five-membered heterocyclic skeleton.

In the above structure, the ligand preferably includes an imidazole skeleton or a triazole skeleton.

In the above structure, it is preferable that the first electrode include at least one of Al and Ag, and that the second electrode include at least one of Mg and Ag.

One embodiment of the present invention includes, in its category, a display device including the light-emitting element with any one of the above-described structures and at least one of a color filter and a transistor; an electronic device including the display device and at least one of a housing and a touch sensor; and a lighting device including the light-emitting element with any one of the above-described structures and at least one of a housing and a touch sensor. Note that a light-emitting device in this specification means an image display device or a light source (including a lighting device). In addition, a display module in which a light-emitting device is provided with a connector such as a flexible printed circuit (FPC) or a tape carrier package (TCP), a display module in which a printed wiring board is provided on the tip of a TCP, and a display module in which an integrated circuit (IC) is directly mounted on a light-emitting device by a chip on glass (COG) method may include the light-emitting element.

With one embodiment of the present invention, a novel light-emitting element can be provided. With one embodiment of the present invention, a novel light-emitting element emitting light with high color purity can be provided. With one embodiment of the present invention, a novel light-emitting element having high emission efficiency can be provided. With one embodiment of the present invention, a novel light-emitting element having high emission efficiency can be provided. With one embodiment of the present invention, a novel light-emitting element with low power consumption can be provided. With one embodiment of the present invention, a method for fabricating a novel light-emitting element can be provided.

Note that the descriptions of these effects do not disturb the existence of other effects. In one embodiment of the present invention, there is no need to achieve all the above effects. Other effects will be apparent from and can be derived from the descriptions of the specification, the drawings, the claims, and the like.

BRIEF DESCRIPTION OF THE DRAWINGS

FIGS. 10A and 10B are schematic cross-sectional views each illustrating a display device of one embodiment of the present invention.

FIG. 27 illustrates lighting devices of embodiments of the present invention.

DETAILED DESCRIPTION OF THE INVENTION

Figure 1A:
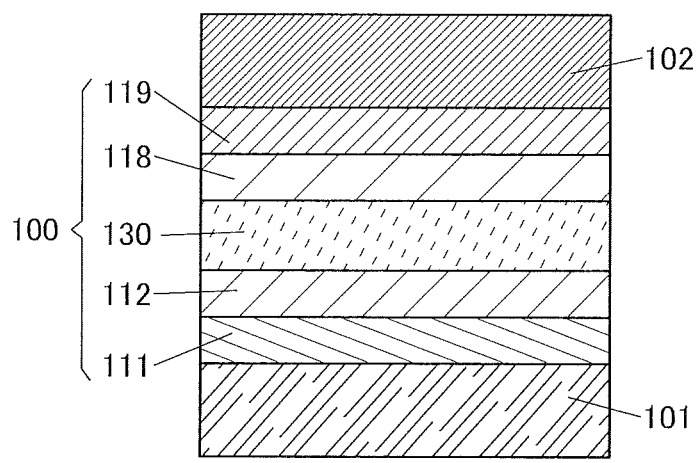
FIGS. 1A and 1B are schematic cross-sectional views illustrating a light-emitting element of one embodiment of the present invention.

Embodiments of the present invention will be described below with reference to the drawings. Note that the present invention is not limited to the following description, and various changes and modifications can be made without departing from the spirit and scope of the present invention. Therefore, the present invention should not be construed as being limited to the description in the following embodiments.

Note that the position, size, range, or the like of each component illustrated in drawings and the like is not accurately represented in some cases for easy understanding. Therefore, the disclosed invention is not necessarily limited to the position, size, range, or the like disclosed in the drawings and the like.

Ordinal numbers such as "first" and "second" in this specification and the like are used for convenience and do not denote the order of steps or the stacking order of layers in some cases. Therefore, for example, the term "first" can be replaced with the term "second", "third", or the like as appropriate. In addition, the ordinal numbers in this specification and the like are not necessarily the same as the ordinal numbers used to specify one embodiment of the present invention.

In the description of modes of the present invention in this specification and the like with reference to the drawings, the same components in different diagrams are commonly denoted by the same reference numeral.

In general, color is defined by three aspects of hue (corresponding to the wavelength of light of a single color), chroma (saturation, i.e., the degree to which it differs from white), and value (brightness, i.e., the intensity of light). In this specification and the like, color may be defined by only one of the above three aspects or two of the aspects which are selected arbitrarily. In this specification, a difference between two colors of light means a difference in at least one of the above three aspects and includes a difference in the shapes of two spectra of light or in the distributions of the relative intensity of the peaks in the spectra.

In this specification and the like, a blue wavelength region is a wavelength region greater than or equal to 440 nm and less than or equal to 470 nm and blue light has at least one peak of emission spectrum in the blue wavelength region; a green wavelength region is a wavelength region greater than 470 nm and less than 550 nm and green light has at least one peak of emission spectrum in the green wavelength region; a yellow wavelength region is a wavelength region greater than or equal to 550 nm and less than 590 nm and yellow light has at least one peak of emission spectrum in the yellow wavelength region; and a red wavelength region is a wavelength region greater than or equal to 590 nm and less than or equal to 740 nm and red light has at least one peak of emission spectrum in the red wavelength region.

In this specification and the like, a fluorescent material refers to a material that emits light in the visible light region when the level of the lowest singlet excited state ($S_1$ level) relaxes to the ground state. A phosphorescent material refers to a material that emits light in the visible light region at room temperature when the level of the lowest triplet excited state ($T_1$ level) relaxes to the ground state. That is, the phosphorescent material refers to a material that can convert triplet excitation energy into visible light.

Note that in this specification and the like, "room temperature" refers to a temperature in a range of 0° C. to 40° C.

In this specification and the like, the terms "film" and "layer" can be interchanged with each other. For example, the term "conductive layer" can be changed into the term "conductive film" in some cases, and the term "insulating film" can be changed into the term "insulating layer" in some cases.

Embodiment 1

In this embodiment, light-emitting elements each of which is one embodiment of the present invention are described below with reference to FIGS. 1A and 1B to FIGS. 7A to 7C and FIG. 28 to FIG. 42.

<1. Structure Example 1 of Light-Emitting Element>

FIG. 1A is a cross-sectional view illustrating a light-emitting element of one embodiment of the present invention. A light-emitting element 150 illustrated in FIG. 1A includes a pair of electrodes (an electrode 101 and an electrode 102) and an EL layer 100 between the pair of electrodes. The EL layer 100 includes at least a light-emitting layer 130.

The EL layer 100 illustrated in FIG. 1A includes, in addition to the light-emitting layer 130, functional layers such as a hole-injection layer 111, a hole-transport layer 112, an electron-transport layer 118, and an electron-injection layer 119.

Note that in this embodiment, although description is given assuming that the electrode 101 serves as an anode and the electrode 102 serves as a cathode, respectively, they can be interchanged for the structure of the light-emitting element 150. That is, the stacking order of the layers between the electrodes may be reversed assuming that the electrode 101 serves as a cathode and the electrode 102 serves as an anode. Therefore, In other words, the hole-injection layer 111, the hole-transport layer 112, the light-emitting layer 130, the electron-transport layer 118, and the electron-injection layer 119 may be stacked in this order from the anode side.

Note that the structure of the EL layer 100 is not limited to the structure illustrated in FIG. 1A, and a structure may be employed in which at least one selected from the hole-injection layer 111, the hole-transport layer 112, the electron-transport layer 118, and the electron-injection layer 119 is included. Alternatively, the EL layer 100 may include a functional layer which is capable of lowering a hole injection barrier or an electron injection barrier, improving a hole-transport property or an electron-transport property, inhibiting a hole-transport property or an electron-transport property, or suppressing a quenching phenomenon by an electrode, for example. Each of the light-emitting layer 130 and the functional layers may be a single layer or a stacked layer formed of a plurality of layers.

Figure 1B:
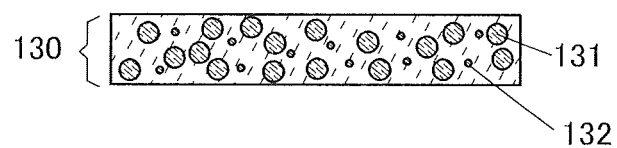

FIG. 1B is a schematic cross-sectional view of an example of the light-emitting layer 130 in FIG. 1A. The light-emitting layer 130 in FIG. 1B includes at least a host material 131 and a guest material 132.

A light-emitting organic compound can be used as the guest material 132. The light-emitting organic compound preferably has a function of converting triplet excitation energy into light emission. Alternatively, the light-emitting organic compound preferably has a function of emitting phosphorescence at room temperature. In these cases, triplet excitation energy of excitons generated in the light-emitting layer 130 can be used for light emission as well as singlet excitation energy.

To that end, each of the lowest energy levels in a singlet excited state (S1 level) and in a triplet excited state (T1 level) of the host material 131 is preferably higher than the lowest energy level in a triplet excited state (T1 level) of the guest material 132.

Figure 2A:
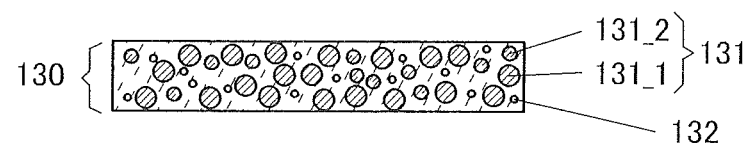
FIGS. 2A and 2B are schematic cross-sectional views each illustrating a light-emitting element of one embodiment of the present invention.

FIG. 2A is a schematic cross-sectional view illustrating another example of the light-emitting layer 130 in FIG. 1A. The host material 131 may be consisted of one kind of substance as illustrated in FIG. 1B or may be consisted of plural kinds of substances as illustrated in FIG. 2A. In the case where the host material 131 is consisted of plural kinds of substances, these materials preferably form an excited complex (also referred to as an exciplex).

The guest material 132 may be consisted of one kind of material or may be consisted of plural kinds of materials. In the case where the guest material 132 is consisted of plural kinds of materials, the kinds of materials can emit light with different colors from one another.

In the description below, a phosphorescent material is used as the guest material 132. Therefore, the guest material 132 may also referred to as a light-emitting material or a phosphorescent material.

<<1-1. Microcavity>>

The light-emitting element 150 illustrated in FIG. 1A preferably has a microresonator (microcavity) structure. The microcavity structure is described below.

Light emitted from the light-emitting layer 130 resonates between a pair of electrodes (the electrode 101 and the electrode 102). Therefore, the light-emitting layer 130 is preferably formed in a position at which the wavelength of light emitted from the light-emitting layer 130 is intensified. For example, each of an optical distance between a reflective region of the electrode 101 and a light-emitting region of the light-emitting layer 130 and an optical distance between a reflective region of the electrode 102 and the light-emitting region of the light-emitting layer 130 is adjusted to be close to $(2m'-1)\lambda_B/4$ (m' is a natural number, and $\lambda_B$ is the wavelength of a desired color), whereby light at a desired wavelength emitted from the light-emitting layer 130 can be intensified. In other words, in order to meet the above optical distance condition of the light-emitting element 150, it is preferable to adjust the optical distance between the reflective region of the electrode 101 and the reflective region of the electrode 102 to be close to $m\lambda_B/2$ (m is a natural number). Note that the optical distance is represented by the product of distance and refractive index.

It is difficult to precisely determine the reflective regions of the electrode 101 and the electrode 102; therefore, the optical distance for intensifying light emitted from the light-emitting layer 130 may be derived on the assumption that certain regions of the electrode 101 and the electrode 102 are the reflective regions. It is also difficult to precisely determine the light-emitting region of the light-emitting layer 130; therefore, the optical distance for intensifying light emitted from the light-emitting layer 130 may be derived on the assumption that a certain region of the light-emitting layer 130 is the light-emitting region.

Since the light-emitting element 150 has a microcavity structure, light emitted from the light-emitting layer 130 can have a narrow spectrum width; thus, light emission with high color purity can be obtained.

For the microcavity structure, it is preferable that the electrode 101 have a function of reflecting light and the electrode 102 have a function of reflecting light and a function of transmitting light. Therefore, the electrode 101 preferably includes a conductive layer having a function of reflecting visible light. The electrode 102 preferably includes a conductive layer having a function of reflecting visible light and a function of transmitting visible light. Note that functions of the electrode 101 and the electrode 102 may be interchanged. That is, the electrode 101 may have a function of reflecting light and a function of transmitting light while the electrode 102 has a function of reflecting light.

Figure 2B:
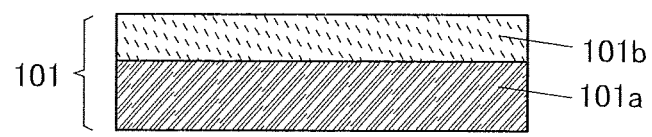

FIG. 2B is a schematic cross-sectional view illustrating another example of the electrode 101 in FIG. 1A. The electrode 101 may be a single layer or a stacked layer formed of a plurality of layers. In the case where the electrode 101 includes a conductive layer 101a and a conductive layer 101b as illustrated in FIG. 2B, the conductive layer 101a preferably has a function of reflecting visible light and the conductive layer 101b preferably has a function of transmitting visible light. In that case, by controlling the thickness of the conductive layer 101b in the electrode 101, the optical distance between the reflective region of the electrode 101 and the reflective region of the electrode 102 in the light-emitting element 150 can be adjusted to be close to $m\lambda_B/2$ (m is a natural number and $\lambda_B$ is the wavelength of a desired color).

To set the optical distance between the reflective region of the electrode 101 and the reflective region of the electrode 102 to the distance with which light at a desired wavelength is intensified, it is preferable to control the thickness of the hole-injection layer 111 in addition to the thickness of the conductive layer 101b in the electrode 101. Note that the layers whose thicknesses are controlled for adjusting the optical distance are not limited to these layers.

To increase the reflectance of the electrode 101 and the emission efficiency of the light-emitting element 150, it is preferable that the electrode 101 or the conductive layer 101a include at least one of aluminum (Al) and silver (Ag). Al is preferable because the material cost is low and patterning can be easily performed, leading to a reduction in the manufacturing cost of the light-emitting element 150. Ag is a material having a particularly high reflectivity, and suitable for increasing the emission efficiency of the light-emitting element 150. Note that in the case where the electrode 101 is a stacked layer of a plurality of layers, at least one of the layers includes Al and/or Ag.

The electrode 102 preferably includes a conductive layer having a function of reflecting visible light and a function of transmitting visible light. To increase the emission efficiency of the light-emitting element 150, the electrode 102 preferably includes at least one of magnesium (Mg) and Ag. Mg is preferable because Mg has a low work function and high electron-injection properties, leading to a reduction in driving voltage of the light-emitting element. Ag is preferable because Ag has a low light absorptance, and thus the electrode 102 with high reflectance and high transmittance can be formed by controlling the thickness of a layer including Ag as appropriate. Specifically, the thickness of the layer including Ag is preferably greater than or equal to 5 nm and less than or equal to 30 nm. Note that in the case where the electrode 102 is a stacked layer of a plurality of layers, at least one of the layers includes Mg and/or Ag.

With the above-described microcavity structure, light scattering and light absorption in the vicinity of the electrodes of the light-emitting element can be prevented and the light extraction efficiency can be improved.

<<1-2. Emission Spectrum of Guest Material>>

In the microcavity structure, to increase the light extraction efficiency and emission efficiency of a light-emitting element, the optical distance is preferably set such that the wavelength of light intensified by the microcavity structure is close to the wavelength of the emission spectrum of a guest material contained in the light-emitting element. In particular, the optical distance is preferably such that the wavelength of light intensified by the microcavity structure is close to the wavelength of the emission spectrum peak of the guest material contained in the light-emitting element. Note that the full width at half maximum of the emission spectrum of the guest material contained in the light-emitting element is preferably smaller, in which case the microcavity structure is more effective in narrowing the spectrum. Specifically, the full width at half maximum of the emission spectrum of the guest material contained in the light-emitting element is preferably greater than or equal to 20 nm and less than or equal to 80 nm, more preferably greater than or equal to 20 nm and less than or equal to 70 nm.

High emission efficiency and high color purity are important for a light-emitting element used in a display device. A display device in which a light-emitting element with high color purity is used for a pixel can perform display in a wide color gamut, and thus can have a high added value. It is preferable to use a light-emitting element with high emission efficiency and high color purity particularly for a blue sub-pixel among sub-pixels, in which case a display device including the light-emitting element can reduce power consumption and perform display in a wide color gamut.

Note that the major color gamut standards used for display devices such as televisions and mobile devices are described below as examples.

The Standard RGB (sRGB) standard and the high definition television (HDTV, also referred to as high-vision) standard (ITU-R BT.709) are color spaces widely used for display devices included in electronic devices such as personal computers, digital cameras, and printers. In the sRGB standard and the HDTV standard, the chromaticity coordinates (x, y) in CIE 1931 chromaticity coordinates (xy chromaticity coordinates), which are defined by the International Commission on Illumination (CIE), of red are (0.64, 0.33); green, (0.30, 0.60); and blue, (0.15, 0.06). In the phase alternating line (PAL) standard, which is a standard of color space used for television broadcasting, the chromaticity coordinates (x, y) of red are (0.64, 0.33); green, (0.29, 0.60); and blue, (0.15, 0.06). In the national television system committee (NTSC) standard, which is also a standard of color space used for television broadcasting, the chromaticity coordinates (x, y) of red are (0.67, 0.33); green, (0.21, 0.71); and blue, (0.14, 0.08). In the digital cinema initiatibes (DCI)-P3 standard, which is a standard of color space used for digital cinema projection, the chromaticity coordinates (x, y) of red are (0.68, 0.32); green, (0.265, 0.69); and blue, (0.15, 0.06). In the standard (ITU-R BT.2020) used for ultra-high definition television (UHDTV, also referred to as super high vision) typified by 4 k×2 k (3840 pixels in the horizontal direction and 2160 pixels in the perpendicular direction) or 8 k×4 k (7680 pixels in the horizontal direction and 4320 pixels in the perpendicular direction), the chromaticity coordinates (x, y) of red are (0.708, 0.292); green, (0.170, 0.779); and blue, (0.131, 0.046).

Accordingly, in a light-emitting element containing a guest material emitting blue light, the chromaticity y is preferably less than or equal to 0.08 to meet the NTSC standard. The chromaticity y is preferably less than or equal to 0.06 to meet the sRGB standard, the ITU-R BT.709 standard, the PAL standard, and the DCI-P3 standard. The chromaticity y is preferably less than or equal to 0.046 for achieving the ITU-R BT.2020 standard.

Note that the chromaticity coordinates (x, y) of monochromatic light with a wavelength of 440 nm are (0.1644, 0.0109) and those of monochromatic light with a wavelength of 470 nm are (0.1241, 0.0578); thus, the values of chromaticity y are sufficiently low.

Therefore, to achieve the above standards, the emission spectrum of the guest material emitting blue light preferably has a peak in a wavelength region ranging from 440 nm to 470 nm. The full width at half maximum of this emission spectrum is preferably greater than or equal to 20 nm and less than or equal to 80 nm, and more preferably greater than or equal to 20 nm and less than or equal to 70 nm.

Note that the chromaticity coordinates (x, y) of monochromatic light with a wavelength of 530 nm are (0.1547, 0.8059); thus, the value of chromaticity y is high.

Therefore, to meet the above standards, as to light emission from the guest material emitting blue light, the light intensity at a wavelength of 530 nm is preferably greater than or equal to 0% and less than or equal to 50% of the maximum value of the light intensity. The chromaticity y in the CIE 1931 chromaticity coordinates, which is calculated from this emission spectrum, is preferably greater than or equal to 0.01 and less than or equal to 0.3. With use of the microcavity structure for the light-emitting element containing the guest material that emits such light, the light-emitting element can emit light with the chromaticity meeting the above standards.

Note that for measurement of the emission spectrum of the guest material, it is preferable to measure the emission spectrum of a solution containing the guest material, in particular, a dichloromethane solution containing the guest material. Alternatively, as a solvent of the solution containing the guest material, for example, an organic solvent such as methanol, ethanol, propanol, butanol, toluene, hexane, benzene, acetone, acetonitrile, chloroform, diethyl ether, dimethylsulfoxide, ethyl acetate, tetrahydrofuran, dimethylformamide, acetic acid, or formic acid, or water may be used.

In order to increase the emission efficiency of the light-emitting element, the guest material preferably has a function of converting the triplet excitation energy into light emission. Alternatively, the guest material preferably has a function of emitting phosphorescence at room temperature.

Alternatively, the guest material preferably contains iridium. Alternatively, the guest material preferably includes a nitrogen-containing five-membered heterocyclic skeleton which is coordinated to iridium. Alternatively, a ligand coordinated to iridium preferably includes an imidazole skeleton or a triazole skeleton.

Examples of the guest material include tris{2-[4-(2-adamantyl)-5-methyl-4H-1,2,4-triazol-3-yl-κN2]phenyl-κC}iridium(III) (abbreviation: Ir(Mptz-Adm2)₃), and tris(1,3-dimethyl-5-phenyl-1H-1,2,4-triazolato)iridium(III) (abbreviation: Ir(Mptz1-Me)₃). Note that the guest material that can be used for the light-emitting element of one embodiment of the present invention is not limited to these.

<<1-3. Emission Spectrum of Solution Containing Guest Material>>

Figure 28:
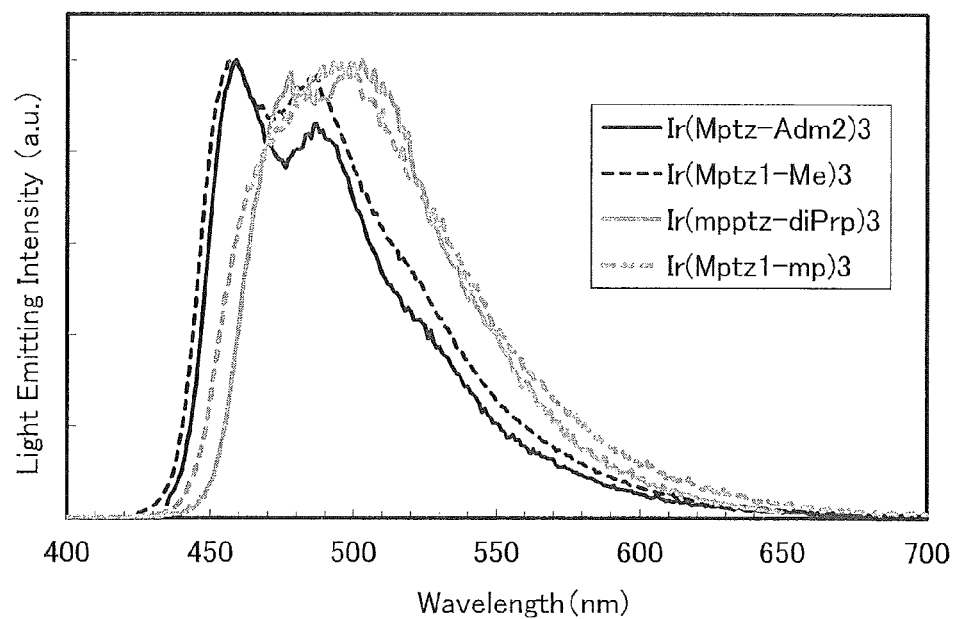
FIG. 28 is a graph showing emission spectra of guest materials used in embodiments of the present invention.

FIG. 28 shows emission spectra of Ir(Mptz-Adm2)₃ in a dichloromethane solution and Ir(Mptz1-Me)₃ in a dichloromethane solution. For comparison, FIG. 28 also shows emission spectra of tris{2-[5-(2-methylphenyl)-4-(2,6-diisopropylphenyl)-4H-1,2,4-triazol-3-yl-κN2]phenyl-κC}iridium(III) (abbreviation: Ir(mpptz-diPrp)₃) in a dichloromethane solution and tris[3-methyl-1-(2-methylphenyl)-5-phenyl-1H-1,2,4-triazolato]iridium(III) (abbreviation: Ir(Mptz1-mp)₃) in a dichloromethane solution. Structural formulae of these compounds are shown below. Table 1 lists the wavelengths of the peaks of emission spectra, the full widths at half maximum, and the CIE chromaticity coordinates (x, y) calculated from the emission spectra of these compounds.

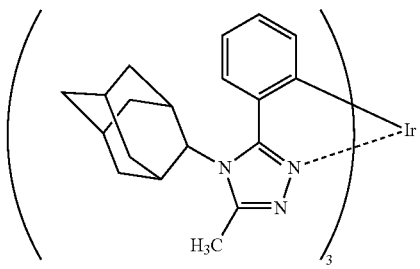

Ir(Mptz-Adm2)₃

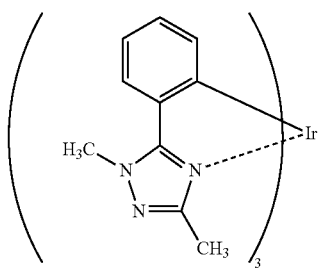

Ir(Mptz1-Me)₃

-continued

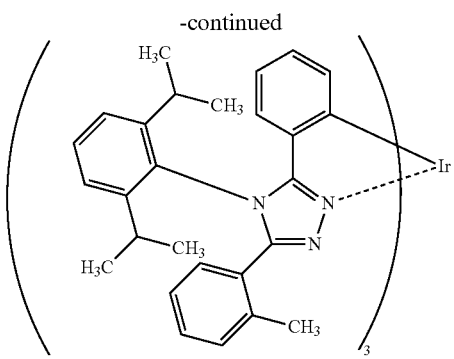

Ir(mpptz-diPrp)₃
(comparative example)

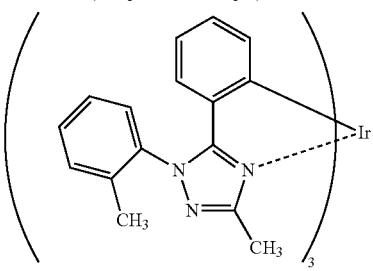

Ir(Mptz1-mp)₃
(comparative example)

TABLE 1

| | Wavelength of the emission spectrum peak (nm) | Full width at half maximum (nm) | CIE cromaticity coordinates (x, y) |
|---|---|---|---|
| Ir(Mptz-Adm2)₃ | 459 | 65 | (0.165, 0.267) |
| Ir(Mptz1-Me)₃ | 457 | 79 | (0.170, 0.273) |
| Ir(mpptz-diPrp)₃ | 503 | 77 | (0.185, 0.425) |
| Ir(Mptz1-mp)₃ | 493 | 88 | (0.201, 0.395) |

The emission spectrum of each of Ir(Mptz-Adm2)₃ and Ir(Mptz1-Me)₃ has a peak in a wavelength region ranging from 440 nm to 470 nm and has a full width at half maximum of greater than or equal to 20 nm and less than or equal to 80 nm. The light intensity at a wavelength of 530 nm is greater than or equal to 0% and less than or equal to 50% of the maximum light intensity. The chromaticities y in the CIE 1931 chromaticity coordinates, which are calculated from these emission spectra, are greater than or equal to 0.01 and less than or equal to 0.3. Therefore, Ir(Mptz-Adm2)₃ and Ir(Mptz1-Me)₃ are guest materials suitable for the light-emitting element of one embodiment of the present invention. In particular, Ir(Mptz-Adm2)₃ is preferable because its full width at half maximum of the emission spectrum is greater than or equal to 20 nm and less than or equal to 70 nm.

<<1-4. Structure of Light-Emitting Element Subjected to Emission Spectrum Measurement>>

Next, emission spectra and element characteristics of light-emitting elements containing the above guest materials are described with reference to FIGS. 29 to 42 and Tables 2 to 7.

Each of Light-emitting elements 1-1 to 1-8 is a light-emitting element of one embodiment of the present invention, and contains Ir(Mptz1-Me)₃ as a guest material. Light-emitting elements 2-1 to 2-8, Light-emitting elements 3-1 to 3-8, and Light-emitting elements 4-1 to 4-4 are comparative light-emitting elements, and contain Ir(mpptz-diPrp)₃, Ir(Mptz1-mp)₃, and N,N'-bis(3-methylphenyl)-N,N'-bis[3-(9-phenyl-9H-fluoren-9-yl)phenyl]pyrene-1,6-diamine (abbreviation: 1,6mMemFLPAPrn), respectively, as a guest material.

Structures and abbreviations of compounds used for these light-emitting elements and structures of the light-emitting elements are shown below.

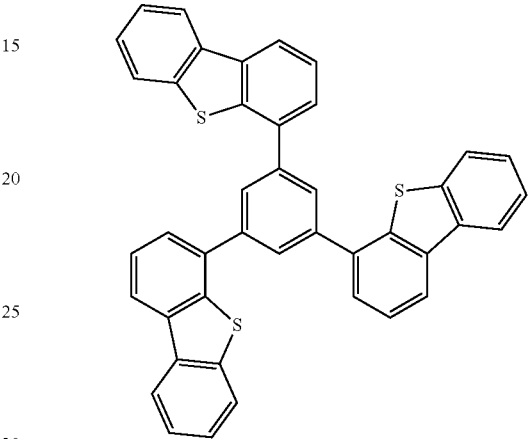

DBT3P-II

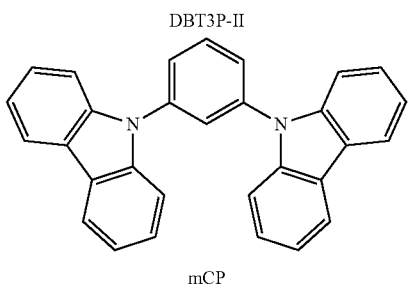

mCP

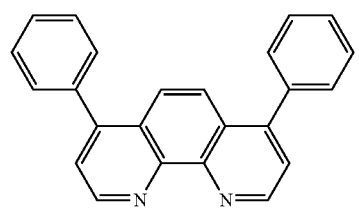

Bphen

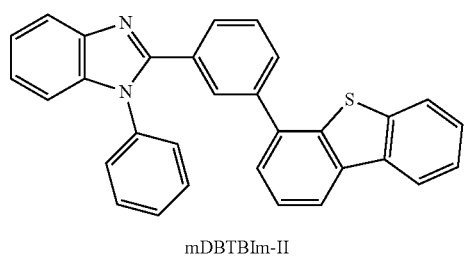

mDBTBIm-II

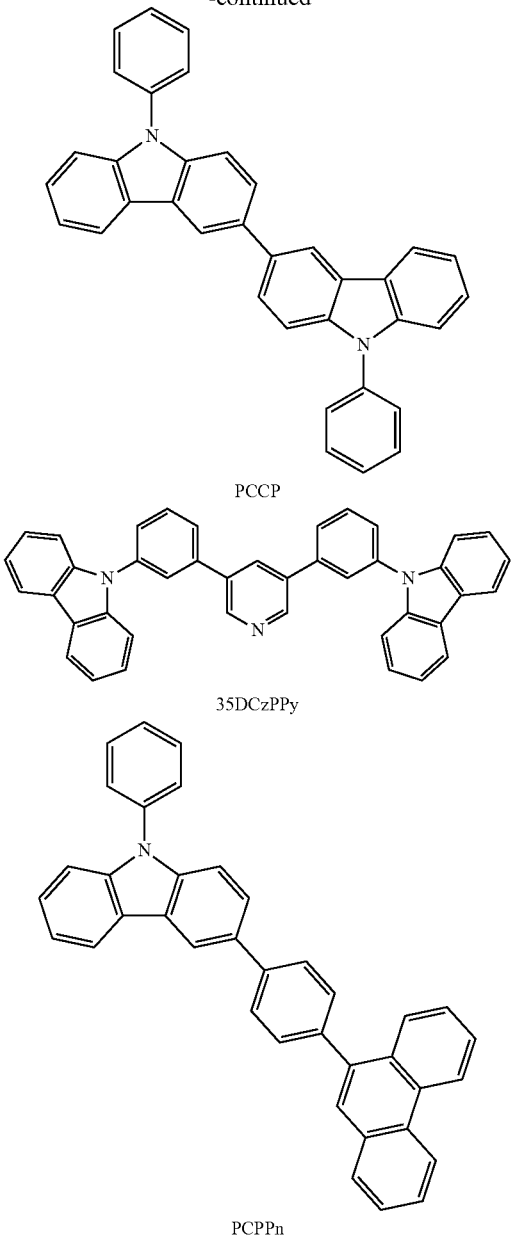

PCCP

35DCzPPy

PCPPn

CzPA 1,6mMemFLPAPrn

TABLE 2

| | Layer | Reference numeral | Thickness (nm) | Material | Weight ratio *1) |
|---|---|---|---|---|---|
| Light-emitting elements 1-1 to 1-8 | Electrode | 102(2) | 70 | DBT3P-II | — |
| | | 102(1) | 15 | Ag:Mg | 1:0.1 |
| | Electron-injection layer | 119 | 1 | LiF | — |
| | Electron-transport layer | 118(2) | Y1 *)2 | Bphen | — |
| | | 118(1) | 10 | mDBTBIm-II:Ir(Mptz1-Me)$_3$ | 1:0.08 |
| | Light-emitting layer | 130 | 30 | mCP:Ir(Mptz1-Me)$_3$ | 1:0.08 |
| | Hole-transport layer | 112 | 20 | mCP | — |
| | Hole-injection layer | 111 | X1 *)2 | DBT3P-II:MoO$_3$ | 1:0.5 |
| | Electrode | 101(3) | 30 | ITSO | — |
| | | 101(2) | 6 | Ti | — |
| | | 101(1) | 200 | Al—Ti | — |

*1) The ratio of Ag:Mg is represented in volume ratio.
*2)                    Thicknesss    Thickness
                         X1 (nm)      Y1 (nm)

TABLE 2-continued

| Layer | Reference numeral | Thickness (nm) | Material | Weight ratio *1) |
|---|---|---|---|---|
| Light-emitting element 1-1 | 70 | 20 | | |
| Light-emitting element 1-2 | 70 | 25 | | |
| Light-emitting element 1-3 | 70 | 30 | | |
| Light-emitting element 1-4 | 70 | 35 | | |
| Light-emitting element 1-5 | 80 | 20 | | |
| Light-emitting element 1-6 | 80 | 25 | | |
| Light-emitting element 1-7 | 80 | 30 | | |
| Light-emitting element 1-8 | 80 | 35 | | |

TABLE 3

| Layer | | Reference numeral | Thickness (nm) | Material | Weight ratio *1) |
|---|---|---|---|---|---|
| Light-emitting elements 2-1 to 2-8 | Electrode | 102(2) | 70 | DBT3P-II | — |
| | | 102(1) | 16 | Ag:Mg | 1:0.2 |
| | Electron-injection layer | 119 | 1 | LiF | — |
| | Electron-transport layer | 118(2) | Z2 *3) | Bphen | — |
| | | 118(1) | Y2 *3) | 35DCzPPy | — |
| | Light-emitting layer | 130(2) | 10 | 35DCzPPy:Ir(mpptz-diPrp)$_3$ | 1:0.06 |
| | | 130(1) | 20 | 35DCzPPy:PCCP:Ir(mpptz-diPrp)$_3$ | 0.3:1:0.06 |
| | Hole-transport layer | 112 | 20 | PCCP | — |
| | Hole-injection layer | 111 | X2 *3) | DBT3P-II:MoO$_3$ | 1:0.5 |
| | Electrode | 101(3) | 30 | ITSO | — |
| | | 101(2) | 6 | Ti | — |
| | | 101(1) | 200 | Al—Ti | — |

*1) The ratio of Ag:Mg is represented in volume ratio.

*3)

| | Thickness X2 (nm) | Thickness Y2 (nm) | Thickness Z2 (nm) |
|---|---|---|---|
| Light-emitting element 2-1 | 50 | 5 | 10 |
| Light-emitting element 2-2 | 50 | 10 | 15 |
| Light-emitting element 2-3 | 60 | 5 | 10 |
| Light-emitting element 2-4 | 60 | 10 | 15 |
| Light-emitting element 2-5 | 70 | 5 | 10 |
| Light-emitting element 2-6 | 70 | 10 | 15 |
| Light-emitting element 2-7 | 80 | 5 | 10 |
| Light-emitting element 2-8 | 80 | 10 | 15 |

TABLE 4

| Layer | | Reference numeral | Thickness (nm) | Material | Weight ratio *1) |
|---|---|---|---|---|---|
| Light-emitting elements 3-1 to 3-8 | Electrode | 102(2) | 70 | DBT3P-II | — |
| | | 102(1) | 15 | Ag:Mg | 1:0.1 |
| | Electron-injection layer | 119 | 1 | LiF | — |
| | Electron-transport layer | 118(2) | Z3 *4) | Bphen | — |
| | | 118(1) | Y3 *4) | 35DCzPPy | — |
| | Light-emitting layer | 130(2) | 10 | 35DCzPPy:Ir(Mptz1-mp)$_3$ | 1:0.05 |
| | | 130(1) | 20 | 35DCzPPy:PCCP:Ir(Mptz1-mp)$_3$ | 0.65:0.35:0.05 |
| | Hole-transport layer | 112 | 20 | PCCP:Ir(Mptz1-mp)$_3$ | 0.8:0.2 |
| | Hole-injection layer | 111 | X3 *4) | DBT3P-II:MoO$_3$ | 1:0.5 |
| | Electrode | 101(3) | 30 | ITSO | — |
| | | 101(2) | 6 | Ti | — |
| | | 101(1) | 200 | Al—Ti | — |

*1) The ratio of Ag:Mg is represented in volume ratio.

*4)

| | Thickness X3 (nm) | Thickness Y3 (nm) | Thickness Z3 (nm) |
|---|---|---|---|
| Light-emitting element 3-1 | 60 | 5 | 15 |
| Light-emitting element 3-2 | 60 | 10 | 15 |
| Light-emitting element 3-3 | 60 | 10 | 20 |
| Light-emitting element 3-4 | 60 | 15 | 20 |
| Light-emitting element 3-5 | 70 | 5 | 15 |
| Light-emitting element 3-6 | 70 | 10 | 15 |
| Light-emitting element 3-7 | 70 | 10 | 20 |
| Light-emitting element 3-8 | 70 | 15 | 20 |

TABLE 5

| Layer | | Reference numeral | Thickness (nm) | Material | Weight ratio *1) |
|---|---|---|---|---|---|
| Light-emitting elements 4-1 to 4-4 | Electrode | 102(2) | 70 | ITO | — |
| | | 102(1) | 15 | Ag:Mg | 1:0.1 |
| | Electron-injection layer | 119 | 1 | LiF | — |
| | Electron-transport layer | 118(2) | 15 | Bphen | — |
| | | 118(1) | Y4 *5) | CzPA | — |
| | Light-emitting layer | 130 | 25 | CzPA:1,6mMemFLPAPrn | 1:0.05 |
| | Hole-transport layer | 112 | 20 | PCPPn | — |
| | Hole-injection layer | 111 | X4 *5) | DBT3P-II:MoO$_3$ | 1:0.5 |
| | Electrode | 101(3) | 10 | ITSO | — |
| | | 101(2) | 6 | Ti | — |
| | | 101(1) | 200 | Al—Ti | — |

*1) The ratio of Ag:Mg is represented in volume ratio.
*5)

| | Thickness X4 (nm) | Thickness Y4 (nm) |
|---|---|---|
| Light-emitting element 4-1 | 100 | 5 |
| Light-emitting element 4-2 | 100 | 15 |
| Light-emitting element 4-3 | 105 | 5 |
| Light-emitting element 4-4 | 105 | 15 |

Examples of methods for fabricating the above-described light-emitting elements are described below.

<<Method for Fabricating Light-Emitting Element 1-1>>

A 200 nm thick Al—Ti film is formed as a conductive layer for forming the electrode 101 in Light-emitting element 1-1. Next, a 6 nm thick Ti film is formed over the Al—Ti film. After the Ti film is formed, baking treatment is performed at 300° C. for one hour to oxidize the Ti film, whereby a titanium oxide film is formed. Then, a 30 nm thick indium tin oxide film containing silicon oxide (abbreviation: ITSO) is formed over the Ti film. Note that the area of the electrode 101 is set to 4 mm$^2$ (2 mm×2 mm).

As the hole-injection layer 111 over the electrode 101, 1,3,5-tri(dibenzothiophen-4-yl)benzene (abbreviation: DBT3P-II) and molybdenum oxide (abbreviation: MoO$_3$) are deposited by co-evaporation in a weight ratio of DBT3P-II:MoO$_3$=1:0.5 to a thickness of 70 nm. Note that co-evaporation is an evaporation method in which a plurality of different substances are concurrently vaporized from their respective evaporation sources. As the hole-transport layer 112, 1,3-bis(N-carbazolyl)benzene (abbreviation: mCP) is deposited by evaporation to a thickness of 20 nm.

As the light-emitting layer 130, mCP and Ir(Mptz1-Me)$_3$ are deposited by co-evaporation in a weight ratio of mCP:Ir(Mptz1-Me)$_3$)=1:0.08 to a thickness of 30 nm. Note that in the light-emitting layer 130, mCP is a host material and Ir(Mptz1-Me)$_3$ is a guest material (a phosphorescent material).

As the electron-transport layer 118, 2-[3-(dibenzothiophen-4-yl)phenyl]-1-phenyl-1H-benzimidazole (abbreviation: mDBTBIm-II) and Ir(Mptz1-Me)$_3$ are deposited over the light-emitting layer 130 by co-evaporation in a weight ratio of mDBTBIm-II:Ir(Mptz1-Me)$_3$)=1:0.08 to a thickness of 10 nm, and successively, bathophenanthroline (Bphen) is deposited by evaporation to a thickness of 20 nm. Next, as the electron-injection layer 119, lithium fluoride (LiF) is deposited by evaporation to a thickness of 1 nm.

As the electrode 102, silver (Ag) and magnesium (Mg) are deposited by co-evaporation in a volume ratio of Ag:Mg=1:0.1 to a thickness of 15 nm, and then, DBT3P-II is deposited to a thickness of 70 nm.

The above-described process is an example of a method for fabricating Light-emitting element 1-1, which is a light-emitting element of one embodiment of the present invention. In Light-emitting elements 1-2 to 1-8, the thicknesses of the hole-injection layer 111 and the electron-transport layer 118 are set as shown in Table 2. Since the optical distance in Light-emitting element 1-1 is relatively short, Light-emitting element 1-1 has a structure suitable for light emission at a relatively short wavelength. Since the optical distance in Light-emitting element 1-8 is relatively long, Light-emitting element 1-8 has a structure suitable for light emission at a relatively long wavelength. Light-emitting elements 1-2 to 1-7 have a structure suitable for light emission at a wavelength longer than the wavelength of light from Light-emitting element 1-1 and shorter than the wavelength of light from Light-emitting element 1-8.

<<Method for Fabricating Light-Emitting Element 2-1>>

The structure of the electrode 101 in Light-emitting element 2-1 is similar to that in Light-emitting element 1-1.

As the hole-injection layer 111 over the electrode 101, DBT3P-II and MoO$_3$ are deposited by co-evaporation in a weight ratio of DBT3P-II:MoO$_3$=1:0.5 to a thickness of 50 nm. As the hole-transport layer 112, 9-phenyl-9H-3-(9-phenyl-9H-carbazol-3-yl)carbazole (abbreviation: PCCP) is deposited by evaporation to a thickness of 20 nm.

As the light-emitting layer 130, 3,5-bis[3-(9H-carbazol-9-yl)phenyl]pyridine (abbreviation: 35DCzPPy), PCCP, and Ir(mpptz-diPrp)$_3$ are deposited by co-evaporation in a weight ratio of 35DCzPPy:PCCP:Ir(mpptz-diPrp)$_3$=0.3:1:0.06 to a thickness of 20 nm, and successively, 35DCzPPy and Ir(mpptz-diPrp)$_3$ are deposited by co-evaporation in a weight ratio of 35DCzPPy:Ir(mpptz-diPrp)$_3$=1:0.06 to a thickness of 10 nm. Note that in the light-emitting layer 130, 35DCzPPy and PCCP are host materials and Ir(mpptz-diPrp)$_3$ is a guest material (a phosphorescent material).

As the electron-transport layer 118, 35DCzPPy is deposited over the light-emitting layer 130 by evaporation to a thickness of 5 nm, and successively, Bphen is deposited by evaporation to a thickness of 10 nm. Next, as the electron-injection layer 119, lithium fluoride (LiF) is deposited by evaporation to a thickness of 1 nm.

As the electrode 102, Ag and Mg are deposited by co-evaporation in a volume ratio of Ag:Mg=1:0.2 to a thickness of 16 nm, and then, DBT3P-II is deposited to a thickness of 70 nm.

The above-described process is an example of a method for fabricating Light-emitting element 2-1, which is a comparative light-emitting element. In Light-emitting elements 2-2 to 2-8, the thicknesses of the hole-injection layer 111 and the electron-transport layer 118 are set as shown in Table 3. Since the optical distance in Light-emitting element 2-1 is relatively short, Light-emitting element 2-1 is suitable for light emission at a relatively short wavelength. Since the optical distance in Light-emitting element 2-8 is relatively long, Light-emitting element 2-8 is suitable for light emission at a relatively long wavelength. Light-emitting elements 2-2 to 2-7 are suitable for light emission at a wavelength longer than the wavelength of light from Light-emitting element 2-1 and shorter than the wavelength of light from Light-emitting element 2-8.

<<Method for Fabricating Light-Emitting Element 3-1>>

The structure of the electrode 101 in Light-emitting element 3-1 is similar to that in Light-emitting element 1-1.

As the hole-injection layer 111 over the electrode 101, DBT3P-II and $MoO_3$ are deposited by co-evaporation in a weight ratio of DBT3P-II:$MoO_3$=1:0.5 to a thickness of 60 nm. As the hole-transport layer 112, PCCP and Ir(Mptz1-mp)$_3$ are deposited by co-evaporation in a weight ratio of PCCP:Ir(Mptz1-mp)$_3$=0.8:0.2 to a thickness of 20 nm.

As the light-emitting layer 130, 35DCzPPy, PCCP, and Ir(Mptz1-mp)$_3$ are deposited by co-evaporation in a weight ratio of 35DCzPPy:PCCP:Ir(Mptz1-mp)$_3$=0.65:0.35:0.05 to a thickness of 20 nm, and successively, 35DCzPPy and Ir(Mptz1-mp)$_3$ are deposited by co-evaporation in a weight ratio of 35DCzPPy:Ir(Mptz1-mp)$_3$=1:0.05 to a thickness of 10 nm. Note that in the light-emitting layer 130, 35DCzPPy and PCCP are host materials and Ir(Mptz1-mp)$_3$ is a guest material (a phosphorescent material).

As the electron-transport layer 118, 35DCzPPy is deposited over the light-emitting layer 130 by evaporation to a thickness of 5 nm, and successively, Bphen is deposited by evaporation to a thickness of 15 nm. Next, as the electron-injection layer 119, lithium fluoride (LiF) is deposited by evaporation to a thickness of 1 nm.

As the electrode 102, Ag and Mg are deposited by co-evaporation in a volume ratio of Ag:Mg=1:0.1 to a thickness of 15 nm, and then, DBT3P-II is deposited to a thickness of 70 nm.

The above-described process is an example of a method for fabricating Light-emitting element 3-1, which is a comparative light-emitting element. In Light-emitting elements 3-2 to 3-8, the thicknesses of the hole-injection layer 111 and the electron-transport layer 118 are set as shown in Table 4. Since the optical distance in Light-emitting element 3-1 is relatively short, Light-emitting element 3-1 is suitable for light emission at a relatively short wavelength. Since the optical distance in Light-emitting element 3-8 is relatively long, Light-emitting element 3-8 is suitable for light emission at a relatively long wavelength. Light-emitting elements 3-2 to 3-7 are suitable for light emission at a wavelength longer than the wavelength of light from Light-emitting element 3-1 and shorter than the wavelength of light from Light-emitting element 3-8.

<<Method for Fabricating Light-Emitting Element 4-1>>

A 200 nm thick Al—Ti film is formed as a conductive layer for forming the electrode 101 in Light-emitting element 4-1. Next, a 6 nm thick Ti film is formed over the Al—Ti film. After the Ti film is formed, baking treatment is performed at 300° C. for one hour to oxidize the Ti film, whereby a titanium oxide film is formed. Then, an ITSO film with a thickness of 10 nm is formed over the Ti film. Note that the area of the electrode 101 is set to 4 mm$^2$ (2 mm×2 mm).

As the hole-injection layer 111 over the electrode 101, DBT3P-II and $MoO_3$ are deposited by co-evaporation in a weight ratio of DBT3P-II:$MoO_3$=1:0.5 to a thickness of 100 nm. As the hole-transport layer 112, 3-[4-(9-phenanthryl)-phenyl]-9-phenyl-9H-carbazole (abbreviation: PCPPn) is deposited by evaporation to a thickness of 20 nm.

As the light-emitting layer 130, 9-[4-(10-phenyl-9-anthracenyl)phenyl]-9H-carbazole (abbreviation: CzPA) and 1,6mMemFLPAPrn are deposited by co-evaporation in a weight ratio of CzPA:1,6mMemFLPAPrn=1:0.05 to a thickness of 25 nm. Note that in the light-emitting layer 130, CzPA is a host material and 1,6mMemFLPAPrn is a guest material (a fluorescent material).

As the electron-transport layer 118, CzPA is deposited over the light-emitting layer 130 by evaporation to a thickness of 5 nm, and successively, Bphen is deposited by evaporation to a thickness of 15 nm. Next, as the electron-injection layer 119, lithium fluoride (LiF) is deposited by evaporation to a thickness of 1 nm.

As the electrode 102, Ag and Mg are deposited by co-evaporation in a volume ratio of Ag:Mg=1:0.1 to a thickness of 15 nm, and then, an indium tin oxide (ITO) film is formed to a thickness of 70 nm.

The above-described process is an example of a method for fabricating Light-emitting element 4-1, which is a comparative light-emitting element. In Light-emitting elements 4-2 to 4-4, the thicknesses of the hole-injection layer 111 and the electron-transport layer 118 are set as shown in Table 5. Since the optical distance in Light-emitting element 4-1 is relatively short, Light-emitting element 4-1 is suitable for light emission at a relatively short wavelength. Since the optical distance in Light-emitting element 4-4 is relatively long, Light-emitting element 4-8 is suitable for light emission at a relatively long wavelength. Light-emitting elements 4-2 and 4-3 are suitable for light emission at a wavelength longer than the wavelength of light from Light-emitting element 4-1 and shorter than the wavelength of light from Light-emitting element 4-4.

<<1-5. Emission Spectra and Element Characteristics of Light-Emitting Elements>>

Figure 29:
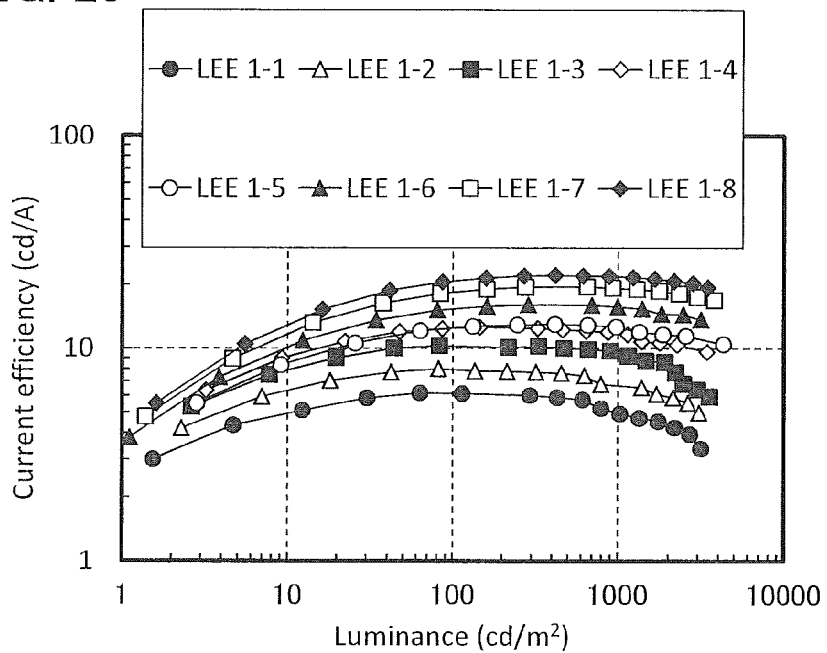
FIG. 29 is a graph showing current efficiency-luminance characteristics of light-emitting elements LEEs of embodiments of the present invention.
Figure 30:
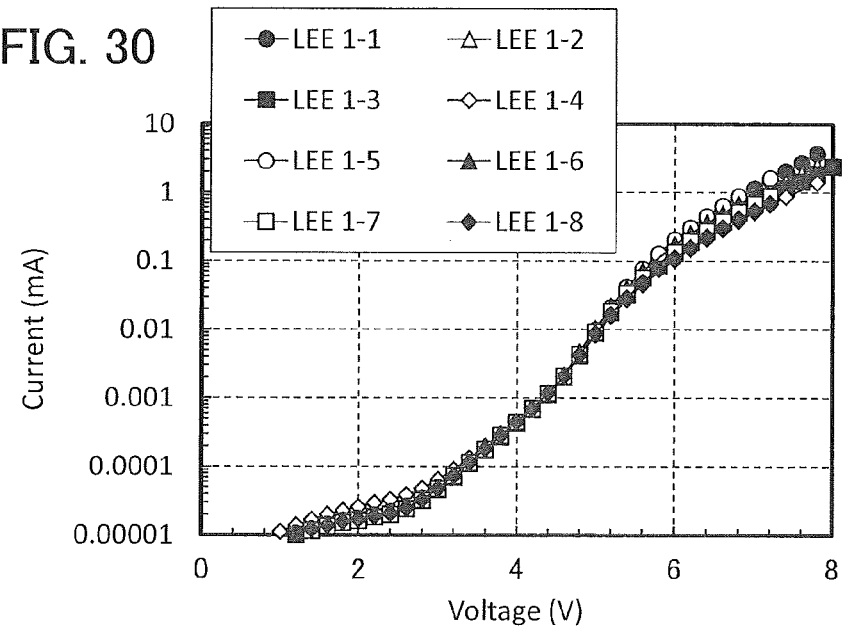
FIG. 30 is a graph showing current-voltage characteristics of light-emitting elements LEEs of embodiments of the present invention.
Figure 31:
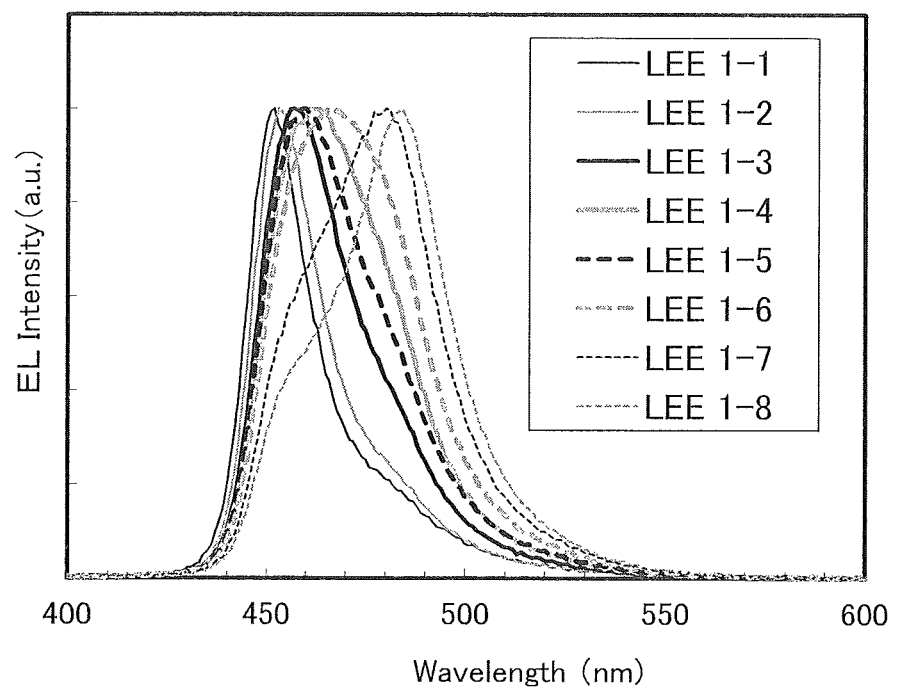
FIG. 31 is a graph showing emission spectra of light-emitting elements LEEs of embodiments of the present invention.
Figure 32:
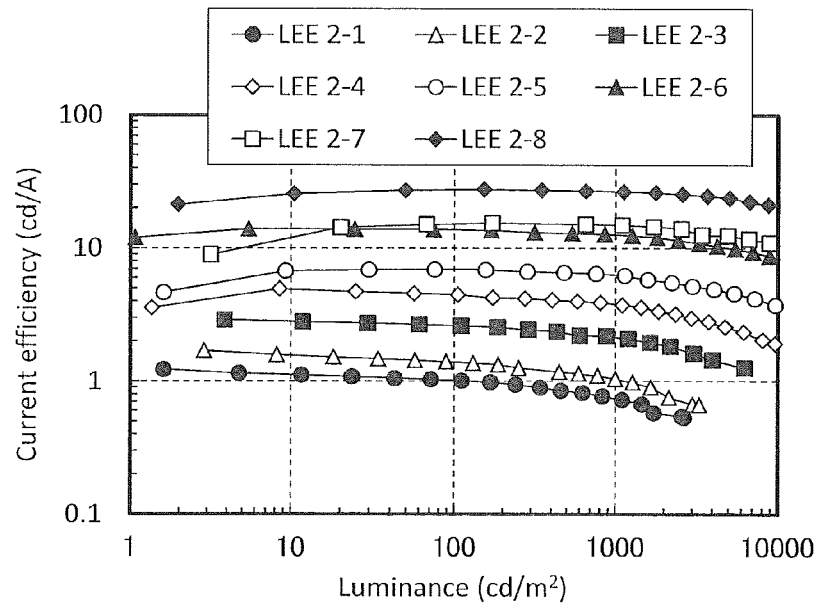
FIG. 32 is a graph showing current efficiency-luminance characteristics of light-emitting elements LEEs of embodiments of the present invention.
Figure 33:
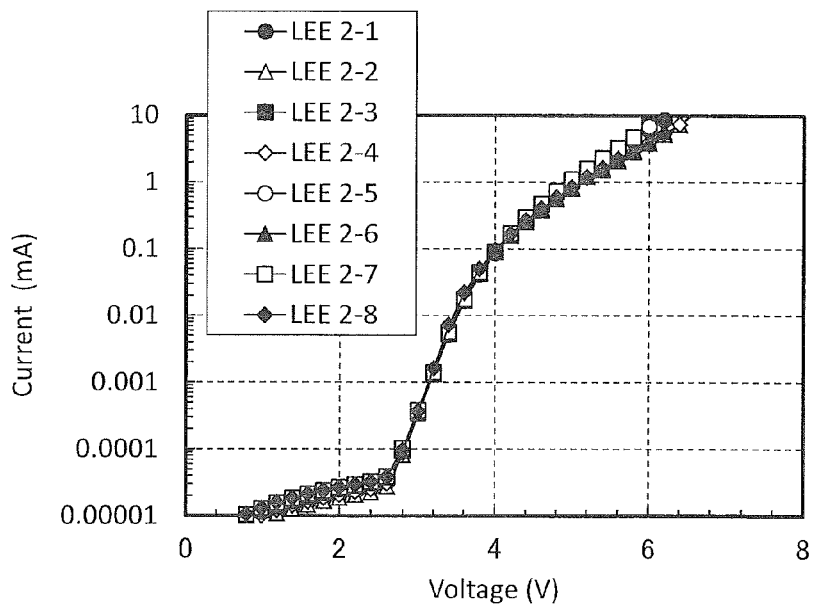
FIG. 33 is a graph showing current-voltage characteristics of light-emitting elements of embodiments LEEs of the present invention.
Figure 34:
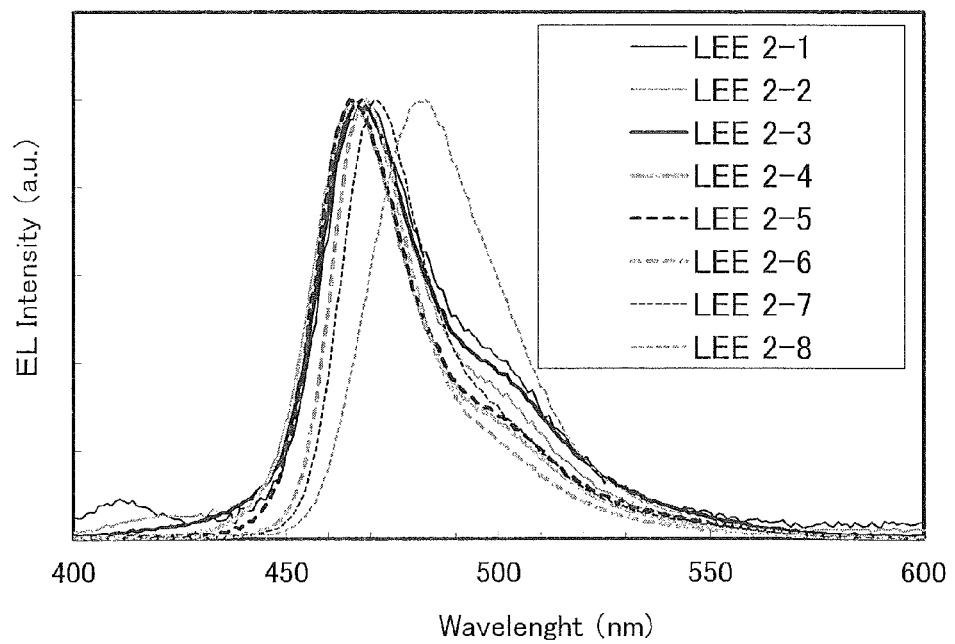
FIG. 34 is a graph showing emission spectra of light-emitting elements of embodiments LEEs of the present invention.
Figure 35:
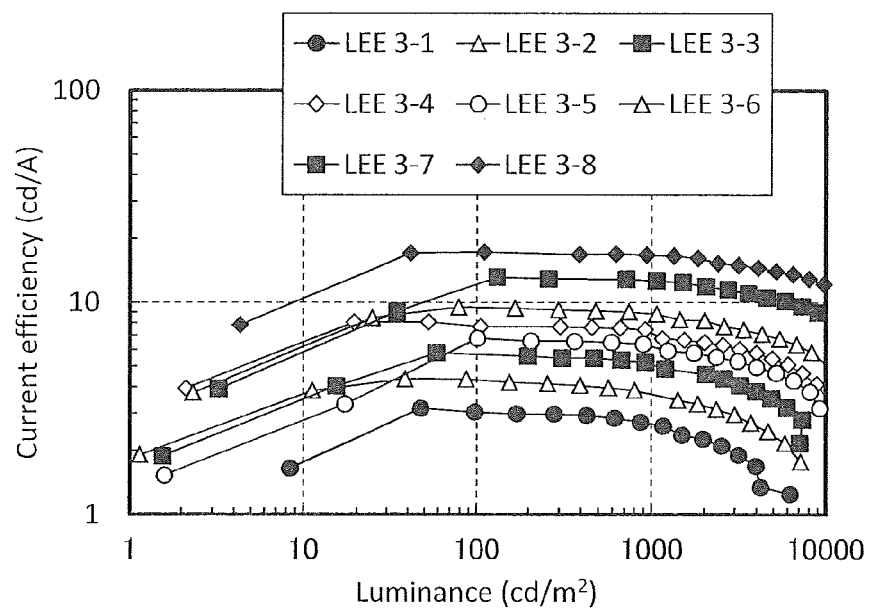
FIG. 35 is a graph showing current efficiency-luminance characteristics of light-emitting elements LEEs of embodiments of the present invention.
Figure 36:
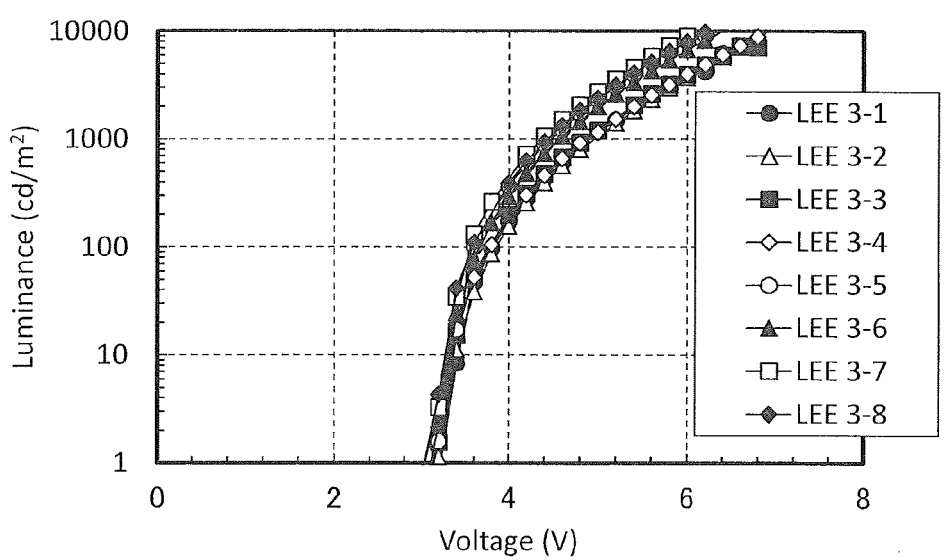
FIG. 36 is a graph showing current-voltage characteristics of light-emitting elements LEEs of embodiments of the present invention.
Figure 37:
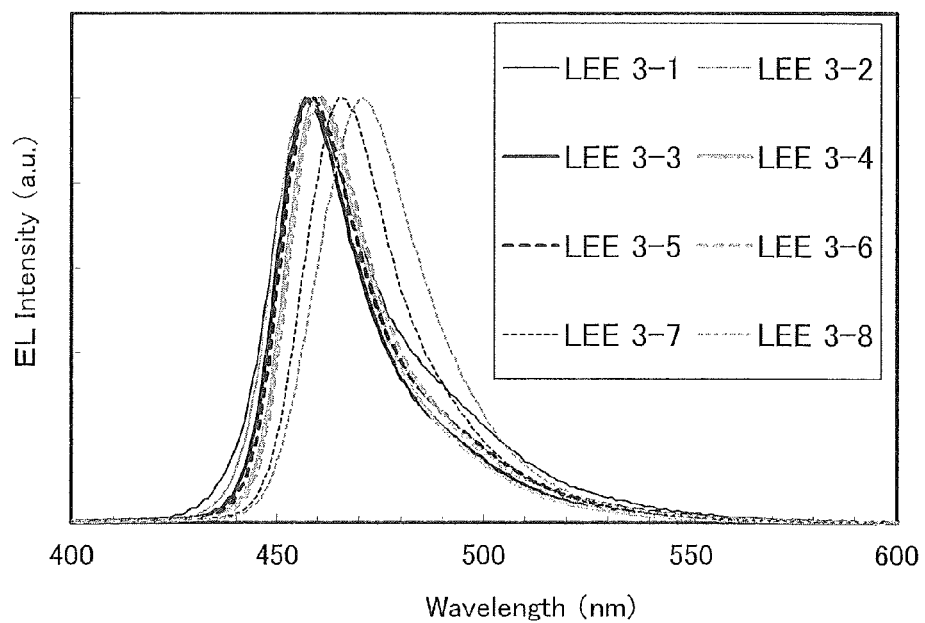
FIG. 37 is a graph showing emission spectra of light-emitting elements LEEs of embodiments of the present invention.
Figure 38:
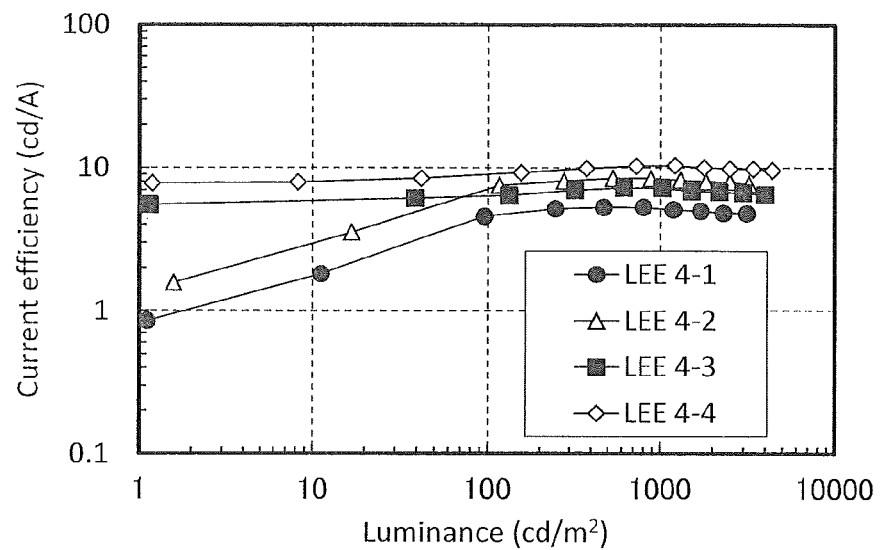
FIG. 38 is a graph showing current efficiency-luminance characteristics of light-emitting elements LEEs of embodiments of the present invention.
Figure 39:
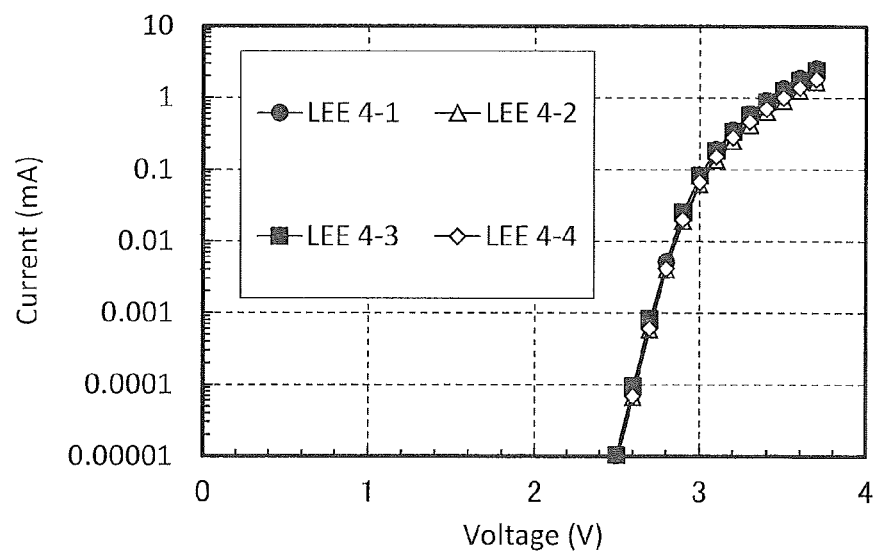
FIG. 39 is a graph showing current-voltage characteristics of light-emitting elements LEEs of embodiments of the present invention.
Figure 40:
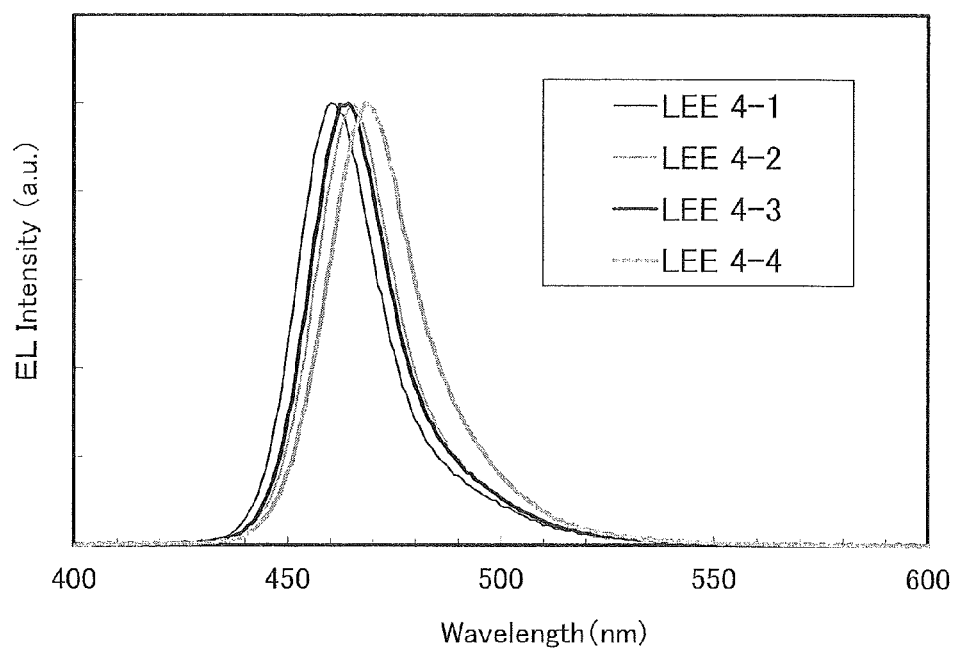
FIG. 40 is a graph showing emission spectra of light-emitting elements of embodiments LEEs of the present invention.

Tables 6 and 7 show element characteristics of Light-emitting elements 1-1 to 1-8, Light-emitting elements 2-1 to 2-8, Light-emitting elements 3-1 to 3-8, and Light-emitting elements 4-1 to 4-4 fabricated by the above methods at around 1000 cd/m$^2$. FIG. 29 shows current efficiency-luminance characteristics of Light-emitting elements 1-1 to 1-8, FIG. 30 shows current-voltage characteristics thereof, and FIG. 31 shows emission spectra thereof. FIG. 32 shows current efficiency-luminance characteristics of Light-emitting elements 2-1 to 2-8, FIG. 33 shows current-voltage characteristics thereof, and FIG. 34 shows emission spectra thereof. FIG. 35 shows current efficiency-luminance characteristics of Light-emitting elements 3-1 to 3-8, FIG. 36 shows current-voltage characteristics thereof, and FIG. 37 shows emission spectra thereof. FIG. 38 shows current efficiency-luminance characteristics of Light-emitting elements 4-1 to 4-4, FIG. 39 shows current-voltage characteristics thereof, and FIG. 40 shows emission spectra thereof. The measurements of the light-emitting elements are performed at room temperature (in an atmosphere kept at 23° C.). The emission spectra of the light-emitting elements are measured when a current at a density of 2.5 mA/cm$^2$ is supplied to the light-emitting elements.

TABLE 6

|  | Voltage (V) | Current density (mA/cm$^2$) | CIE chromaticity coordinates (x, y) | Luminance (cd/m$^2$) | Current efficiency (cd/A) |
| --- | --- | --- | --- | --- | --- |
| Light-emitting element 1-1 | 6.8 | 21 | (0.14, 0.044) | 1000 | 4.9 |
| Light-emitting element 1-2 | 6.8 | 16 | (0.14, 0.050) | 1000 | 6.5 |
| Light-emitting element 1-3 | 6.6 | 9.3 | (0.14, 0.073) | 900 | 10 |
| Light-emitting element 1-4 | 6.6 | 7.3 | (0.13, 0.094) | 870 | 12 |
| Light-emitting element 1-5 | 6.2 | 7.7 | (0.14, 0.091) | 980 | 13 |
| Light-emitting element 1-6 | 6.2 | 6.4 | (0.13, 0.12) | 1000 | 16 |
| Light-emitting element 1-7 | 6.2 | 4.8 | (0.13, 0.16) | 930 | 19 |
| Light-emitting element 1-8 | 6.2 | 4.0 | (0.12, 0.20) | 880 | 22 |
| Light-emitting element 2-1 | 6.0 | 150 | (0.16, 0.18) | 1100 | 0.73 |
| Light-emitting element 2-2 | 6.0 | 96 | (0.15, 0.15) | 1000 | 1.0 |
| Light-emitting element 2-3 | 5.2 | 40 | (0.14, 0.17) | 880 | 2.2 |
| Light-emitting element 2-4 | 5.2 | 29 | (0.14, 0.13) | 1100 | 3.8 |
| Light-emitting element 2-5 | 4.8 | 18 | (0.14, 0.15) | 1100 | 6.2 |
| Light-emitting element 2-6 | 4.4 | 6.7 | (0.13, 0.16) | 860 | 13 |
| Light-emitting element 2-7 | 4.4 | 7.4 | (0.13, 0.20) | 1100 | 15 |
| Light-emitting element 2-8 | 4.2 | 4.2 | (0.12, 0.31) | 1100 | 27 |

TABLE 7

|  | Voltage (V) | Current density (mA/cm$^2$) | CIE chromaticity coordinates (x, y) | Luminance (cd/m$^2$) | Current efficiency (cd/A) |
| --- | --- | --- | --- | --- | --- |
| Light-emitting element 3-1 | 4.8 | 32 | (0.14, 0.095) | 870 | 2.7 |
| Light-emitting element 3-2 | 5.0 | 29 | (0.14, 0.083) | 1000 | 3.4 |
| Light-emitting element 3-3 | 4.8 | 18 | (0.14, 0.079) | 930 | 5.2 |
| Light-emitting element 3-4 | 4.8 | 12 | (0.14, 0.084) | 920 | 7.4 |
| Light-emitting element 3-5 | 4.4 | 14 | (0.14, 0.092) | 900 | 6.4 |
| Light-emitting element 3-6 | 4.6 | 12 | (0.14, 0.10) | 1100 | 8.8 |
| Light-emitting element 3-7 | 4.4 | 8.4 | (0.14, 0.12) | 1100 | 13 |
| Light-emitting element 3-8 | 4.4 | 5.6 | (0.13, 0.15) | 940 | 17 |
| Light-emitting element 4-1 | 3.4 | 23 | (0.14, 0.063) | 1200 | 5.1 |
| Light-emitting element 4-2 | 3.3 | 10 | (0.14, 0.084) | 880 | 8.5 |
| Light-emitting element 4-3 | 3.3 | 14 | (0.14, 0.079) | 1000 | 7.2 |
| Light-emitting element 4-4 | 3.3 | 12 | (0.13, 0.11) | 1200 | 10 |

Figure 41:
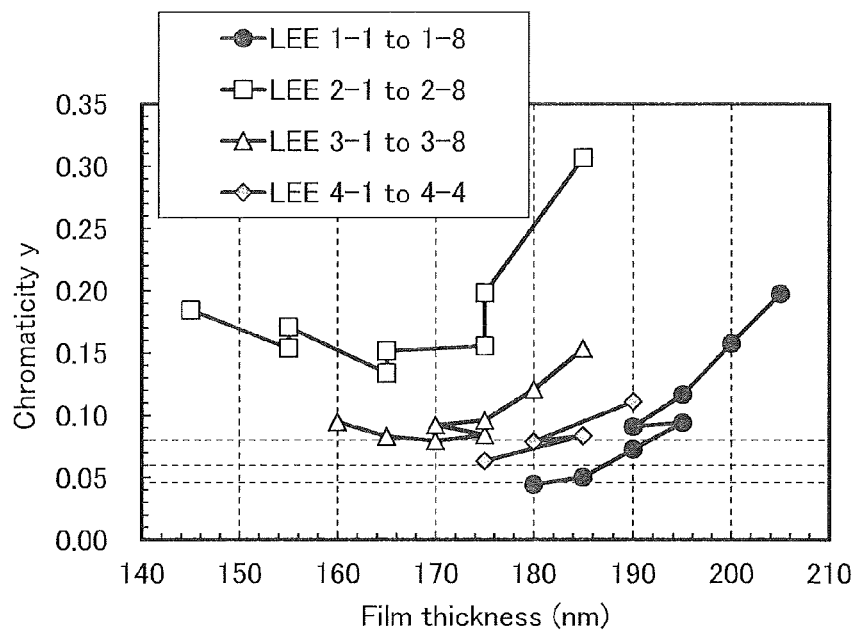
FIG. 41 is a graph showing the correlation between the chromaticity y of light-emitting elements LEEs of embodiments of the present invention and a film thickness between electrodes.
Figure 42:
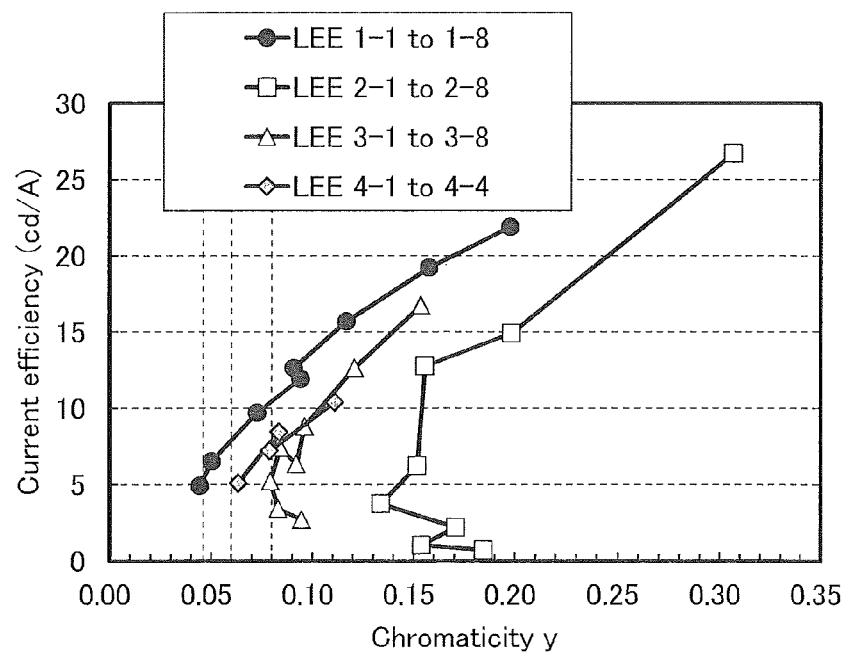
FIG. 42 is a graph showing the correlation between current efficiency of light-emitting elements LEEs of embodiments of the present invention and the chromaticity y.

As to Light-emitting elements 1-1 to 1-8, Light-emitting elements 2-1 to 2-8, Light-emitting elements 3-1 to 3-8, and Light-emitting elements 4-1 to 4-4, FIG. 41 shows the relationship, at around 1000 cd/m$^2$, between the chromaticity y and a film thickness (distance) from the reflective region of the electrode 101 to the reflective region of the electrode 102, and FIG. 42 shows the relationship, at around 1000 cd/m$^2$, between the current efficiency and the chromaticity y. Here, the film thickness between reflective regions used for calculating the optical distance is calculated on the assumption that the reflective region of the electrode 101 refers to an interface between Ti and ITSO in the electrode 101, and the reflective region of the electrode 102 refers to an interface between the electron-injection layer 119 and the electrode 102.

The results of emission spectra in FIG. 31, FIG. 34, FIG. 37, and FIG. 40 show that in the light-emitting elements, the wavelength of light intensified by the microcavity effect is changed depending on the film thickness from the reflective region of the electrode 101 to the reflective region of the electrode 102; that is, the emission spectrum of light extracted to the outside can be changed. Therefore, in order to obtain a desired emission spectrum, it is preferable to adjust the film thickness from the reflective region of the electrode 101 to the reflective region of the electrode 102 in the light-emitting element to be suitable for the emission spectrum.

FIG. 30, FIG. 33, FIG. 36, and FIG. 39 show that the driving voltage in each of Light-emitting elements 1-1 to 1-8 hardly changes even when the film thickness from the reflective region of the electrode 101 to the reflective region of the electrode 102 is changed. The same applies to Light-emitting elements 2-1 to 2-8, Light-emitting elements 3-1 to 3-8, and Light-emitting elements 4-1 to 4-4. Thus, in the structure of the light-emitting element of one embodiment of the present invention, the emission spectrum can be changed by controlling the film thickness from the reflective region of the electrode 101 to the reflective region of the electrode 102 without an increase in driving voltage.

Since the wavelength of light intensified by the microcavity effect is changed depending on the film thickness from the reflective region of the electrode 101 to the reflective region of the electrode 102 in each of the light-emitting elements, the current efficiency is changed as shown in the current efficiency-luminance characteristics in FIG. 29, FIG. 32, FIG. 35, and FIG. 38. This is because the current efficiency is influenced by the change in emission spectrum and the level of the microcavity effect varies between the light-emitting elements. Therefore, in order to increase the current efficiency, it is important that the wavelength of light intensified by the microcavity effect correspond to the wavelength of the emission spectrum, in particular, the wavelength of the emission spectrum peak, of a light-emitting material in each of the light-emitting elements.

In order to obtain deeper blue light or blue light with higher color purity, it is preferable that the optical distance in a light-emitting element be adjusted to intensify light with a shorter wavelength. In Light-emitting elements 1-1 to 1-8, the film thickness from the reflective region of the electrode 101 to the reflective region of the electrode 102 is reduced to shorten the wavelength of light intensified by the microcavity effect; thus, an emission spectrum appears on a short wavelength side, and as a result, a small chromaticity y can be obtained as shown in FIG. 41. Light-emitting elements 1-1 to 1-8 contain Ir(Mptz1-Me)$_3$ as a guest material. The emission spectrum of Ir(Mptz1-Me)$_3$ in a dichloromethane solution has a peak in a wavelength region ranging from 440 nm to 470 nm and a full width at half maximum of greater than or equal to 20 nm and less than or equal to 80 nm. Therefore, Light-emitting elements 1-1 to 1-3 can emit light with a chromaticity y less than or equal to 0.08 which is the chromaticity of blue defined by NTSC. Light-emitting elements 1-1 and 1-2 can emit light with a chromaticity y less than or equal to 0.06 which is the chromaticity of blue defined by sRGB, ITU-R BT.709, PAL, DCI-P3, and the like. Light-emitting element 1-1 can emit light with a chromaticity y less than or equal to 0.046 which is the chromaticity of blue defined by ITU-R BT.2020. As shown in FIG. 42, Light-emitting elements 1-1 and 1-2 can emit light of significantly deep blue with a chromaticity y greater than or equal to 0.01 and less than or equal to 0.06 at a high current efficiency greater than or equal to 3 cd/A. Light-emitting element 1-3 can emit light of excellent blue with a chromaticity y greater than 0.06 and less than or equal to 0.08 at a high current efficiency greater than or equal to 8 cd/A. Light-emitting elements 1-4 and 1-5 can emit light of favorable blue with a chromaticity y greater than 0.08 and less than or equal to 0.1 at a high current efficiency greater than or equal to 10 cd/A.

Similarly in Light-emitting elements 2-1 to 2-8, the film thickness from the reflective region of the electrode 101 to the reflective region of the electrode 102 is reduced to shorten the wavelength of light intensified by the microcavity effect; thus, an emission spectrum with a short wavelength can be obtained, and as a result, a small chromaticity y can be obtained. However, the chromaticity y of light from each of Light-emitting elements 2-1 to 2-8 is greater than or equal to 0.13. This is because the emission spectrum of (Ir(mpptz-diPrp)$_3$) contained in Light-emitting elements 2-1 to 2-8 as a guest material has a peak in a wavelength region greater than 470 nm, which is not sufficient for obtaining light of deeper blue (the color with a chromaticity y less than 0.13). Also in Light-emitting elements 3-1 to 3-8, the film thickness from the reflective region of the electrode 101 to the reflective region of the electrode 102 is reduced to shorten the wavelength of light intensified by the microcavity effect; thus, an emission spectrum with a short wavelength can be obtained, and as a result, a small chromaticity y can be obtained. However, the chromaticity y of light from each of Light-emitting elements 3-1 to 3-8 is greater than 0.07. This is because the emission spectrum of (Ir(Mptz1-mp)$_3$) contained as a guest material in Light-emitting elements 3-1 to 3-8 has a peak in a wavelength region greater than 470 nm, which is not sufficient for obtaining light of deeper blue (the color with a chromaticity y less than or equal to 0.07).

In Light-emitting elements 4-1 to 4-4, the film thickness from the reflective region of the electrode 101 to the reflective region of the electrode 102 is reduced to shorten the wavelength of light intensified by the microcavity effect; thus, an emission spectrum with a short wavelength can be obtained, and as a result, a small chromaticity y can be obtained. Accordingly, Light-emitting elements 4-1 to 4-3 can have a chromaticity y less than or equal to 0.08 which is the chromaticity of blue defined by NTSC. Although Light-emitting elements 4-1 to 4-3 can emit light of excellent blue whose chromaticity y greater than 0.06 and less than or equal to 0.08, the current efficiency is less than 8 cd/A.

Therefore, it is preferable that a guest material contained in the light-emitting element of one embodiment of the present invention have a function of converting the triplet excitation energy into light emission, and that the emission spectrum of the guest material in a dichloromethane solution have a peak in a wavelength region ranging from 440 nm to 470 nm and have a full width at half maximum of greater than or equal to 20 nm and less than or equal to 80 nm. The light intensity at a wavelength of 530 nm is preferably greater than or equal to 0% and less than or equal to 50% of the maximum light intensity. The chromaticity y in the CIE 1931 chromaticity coordinates, which is calculated from the emission spectrum of the guest material in the dichloromethane solution, is preferably greater than or equal to 0.01 and less than or equal to 0.3. With the above guest material, a light-emitting element that emits light with a chromaticity y (the CIE 1931 chromaticity coordinates) greater than or equal 0.01 and less than or equal to 0.06 at a current efficiency greater than or equal to 3 cd/A can be fabricated. Alternatively, a light-emitting element that emits light with a chromaticity y greater than 0.06 and less than or equal to 0.08 at a current efficiency greater than or equal to 8 cd/A can be fabricated. Alternatively, a light-emitting element that emits light with a chromaticity y greater than 0.08 and less than or equal to 0.1 at a current efficiency greater than or equal to 10 cd/A can be fabricated.

Furthermore, blue light with high color purity is blue light whose chromaticity z is larger than the sum of the chromaticity x and the chromaticity y in the CIE 1931 chromaticity coordinates. The chromaticity z is obtained by the following formula: 1−(chromaticity x)−(chromaticity y). Therefore, blue light with a large chromaticity z is blue light whose sum of the chromaticity x and the chromaticity y is small. Specifically, the sum of the chromaticity x and the chromaticity y is preferably less than or equal to 0.3, more preferably less than or equal to 0.23.

In order that the sum of the chromaticity x and the chromaticity y of light emitted from the light-emitting element of one embodiment of the present invention emits light is within the above range, the sum of the chromaticity x and the chromaticity y of the guest material contained in the light-emitting element, which is calculated from the emission spectrum of the guest material in a dichloromethane solution, is preferably greater than or equal to 0.2 and less than or equal to 0.5, like the chromaticities in Table 1. Thus, as shown in Table 6, a light-emitting element that emits light whose sum of the chromaticity x and the chromaticity y is greater than or equal to 0.15 and less than or equal to 0.19 at a current efficiency greater than or equal to 3 cd/A can be fabricated. Alternatively, a light-emitting element that emits light whose sum of the chromaticity x and the chromaticity y is greater than 0.19 and less than or equal to 0.21 at a current efficiency greater than or equal to 8 cd/A can be fabricated. Alternatively, a light-emitting element that emits light whose sum of the chromaticity x and the chromaticity y is greater than 0.21 and less than or equal to 0.23 at a current efficiency greater than or equal to 10 cd/A can be fabricated.

The CIF 1931 chromaticity coordinates (x, y) can be expressed by the CIE 1976 chromaticity coordinates (u', v'). In that case, the chromaticity v' in the CIE 1976 chromaticity coordinates of the guest material contained in the light-emitting element of one embodiment of the present invention, which is calculated from the emission spectrum in the dichloromethane solution, is preferably greater than or equal to 0.035 and less than or equal to 0.45. Thus, a light-emitting element that emits light whose chromaticity v' in the CIE 1976 chromaticity coordinates is greater than or equal to 0.1 and less than or equal to 0.16 at a current efficiency greater than or equal to 3 cd/A can be fabricated. Alternatively, a light-emitting element that emits light whose chromaticity v' is greater than 0.16 and less than or equal to 0.2 at a current efficiency greater than or equal to 8 cd/A can be fabricated. Alternatively, a light-emitting element that emits light whose chromaticity v' is greater than 0.2 and less than or equal to 0.23 at a current efficiency greater than or equal to 10 cd/A can be fabricated.

Note that the chromaticity u' and the chromaticity v' in the CIE 1976 chromaticity coordinates can be expressed by Formula 1 and Formula 2, respectively, using the chromaticity x and the chromaticity y in the CIE 1931 chromaticity coordinates.

[Formula 1]

$$u'=4x/(3-2x+12y) \quad (1)$$

[Formula 2]

$$v'=9y/(3-2x+12y) \quad (2)$$

When a color filter is provided over the electrode through which light is extracted, the color purity of the light-emitting element 150 can be improved. Therefore, the color purity of a display device including the light-emitting element 150 can be improved.

<2. Structure Example 2 of Light-Emitting Element>

Next, a structure example different from the light-emitting element 150 illustrated in FIG. 1A is described below with reference to FIG. 3.

Figure 3:
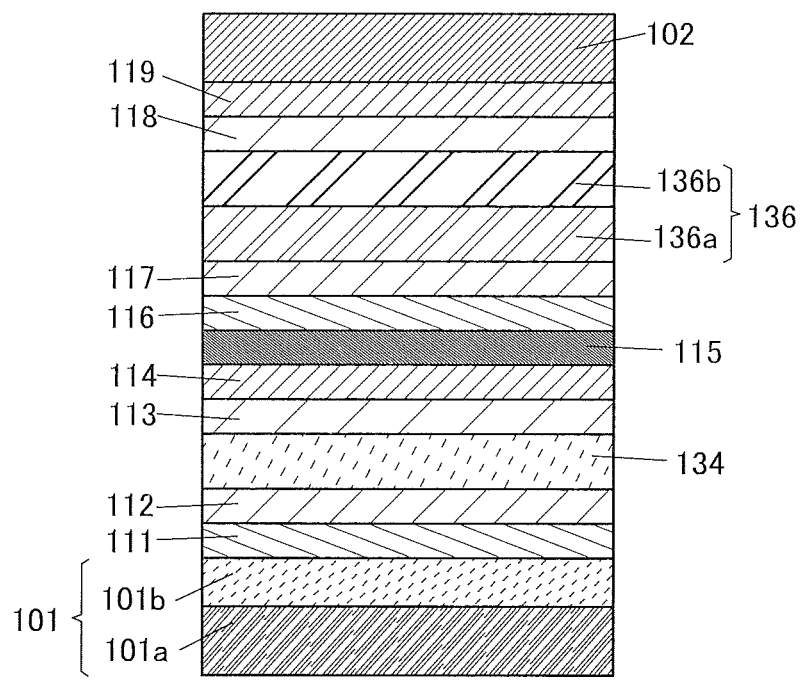
FIG. 3 is a schematic cross-sectional view illustrating a light-emitting element of one embodiment of the present invention.

FIG. 3 is a cross-sectional view illustrating a light-emitting element of one embodiment of the present invention. In FIG. 3, a portion having a function similar to that in FIG. 1A is represented by the same hatch pattern as in FIG. 1A and not especially denoted by a reference numeral in some cases. In addition, common reference numerals are used for portions having similar functions, and a detailed description of the portions is omitted in some cases.

A light-emitting element 152 illustrated in FIG. 3 is a structure example of a tandem light-emitting element in which a plurality of EL layers each including a light-emitting layer are stacked between a pair of electrodes (the electrodes 101 and 102) with a charge-generation layer provided between the EL layers. The tandem light-emitting element 152 includes a light-emitting layer 134, a charge-generation layer 115, and a light-emitting layer 136 between the electrode 101 and the electrode 102. In addition, the hole-injection layer 111, the hole-transport layer 112, an electron-transport layer 113, an electron-injection layer 114, a hole-injection layer 116, a hole-transport layer 117, the electron-transport layer 118, and the electron-injection layer 119 are included.

The light-emitting layers 134 and 136 each contain a light-emitting guest material. The light-emitting layers 134 and 136 can each have a stacked-layer structure of two layers, for example, a light-emitting layer 136a and a light-emitting layer 136b in the light-emitting element 152 in FIG. 3. Two kinds of guest materials (a first material and a second material) having functions of emitting light of different colors are used for the two light-emitting layers, so that light of a plurality of emission colors can be obtained at the same time. It is particularly preferable to select guest materials for the light-emitting layers 134 and 136 so that white light can be obtained by combining light emission from the light-emitting layers.

The light-emitting layer 134 or 136 may have a structure in which three or more layers are stacked or may include a layer that does not contain a guest material.

The light-emitting element 152 preferably has a microcavity structure.

Light emitted from the light-emitting layer 134 and the light-emitting layer 136 resonates between a pair of electrodes (the electrodes 101 and 102). The light-emitting layer 134 is formed at a position such that light at a desired wavelength emitted from the light-emitting layer 134 is intensified. For example, an optical distance from the reflective region of the electrode 101 to the light-emitting region of the light-emitting layer 134 and an optical distance from the reflective region of the electrode 102 to the light-emitting region of the light-emitting layer 134 are adjusted, whereby light at a desired wavelength emitted from the light-emitting layer 134 can be intensified. In addition, the light-emitting layer 136 is formed at a position such that light at a desired wavelength emitted from the light-emitting layer 136 is intensified. For example, an optical distance from the reflective region of the electrode 101 to the light-emitting region of the light-emitting layer 136 and an optical distance from the reflective region of the electrode 102 to the light-emitting region of the light-emitting layer 136 are adjusted, whereby light at a desired wavelength emitted from the light-emitting layer 136 can be intensified.

In the light-emitting layers 134 and 136, the above optical distances are satisfied, and the optical distance between the electrode 101 and the electrode 102 is adjusted to be close to $m\lambda_B/2$ (m is a natural number and $\lambda_B$ is the wavelength of a desired color).

In the case of a tandem light-emitting element in which a plurality of light-emitting layers (here, the light-emitting layers 134 and 136) are stacked with the charge-generation layer 115 provided therebetween, the optical distances of the light-emitting layers 134 and 136 are preferably optimized.

In the light-emitting element 152, one of the light-emitting layer 134 and the light-emitting layer 136 contains a first guest material. The first guest material has a function of converting the triplet excitation energy into light emission. It is preferable that the emission spectrum of the first guest material in a dichloromethane solution have a peak in a wavelength region ranging from 440 nm to 470 nm and have a full width at half maximum of greater than or equal to 20 nm and less than or equal to 80 nm. At this time, the light intensity of the guest material in the dichloromethane solution at a wavelength of 530 nm is preferably greater than or equal to 0% and less than or equal to 50% of the maximum light intensity. The chromaticity y in the CIE 1931 chromaticity coordinates, which is calculated from the emission spectrum of the guest material in the dichloromethane solution, is preferably greater than or equal to 0.01 and less than or equal to 0.3. The other of the light-emitting layer 134 and the light-emitting layer 136 contains a second guest material. The second guest material preferably has a function of emitting any one of green light, yellow-green light, yellow light, orange light, and red light, with the maximum light intensity. The second guest material preferably has a function of converting the triplet excitation energy into light emission.

For the other components in the microcavity structure of the light-emitting element 152, the structure of the light-emitting element 150 can be referred to.

<3. Structure Example 3 of Light-Emitting Element>

Next, structure examples different from the light-emitting elements illustrated in FIG. 1A and FIG. 3 are described below with reference to FIGS. 4A and 4B.

Figure 4A:
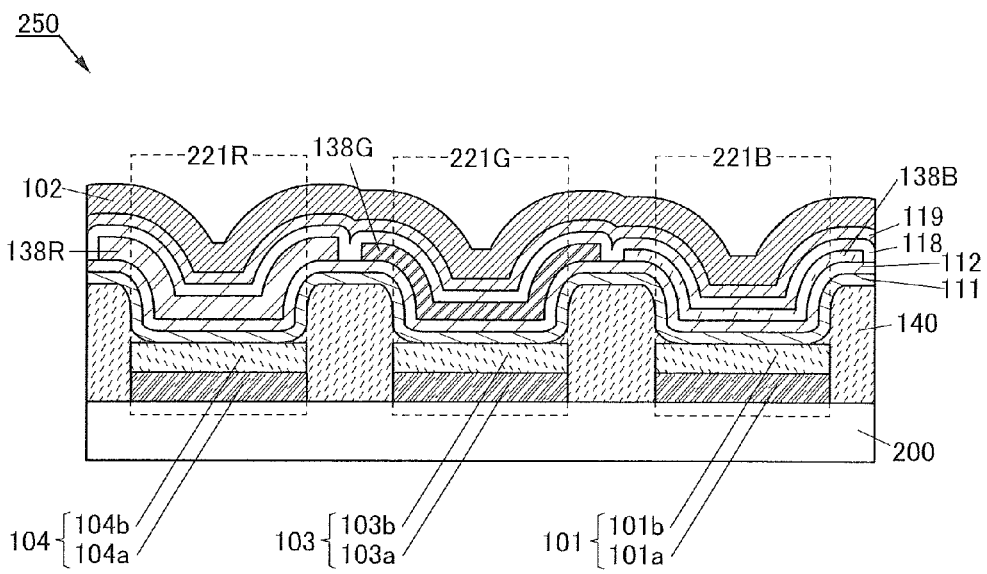
FIGS. 4A and 4B are schematic cross-sectional views each illustrating a light-emitting element of one embodiment of the present invention.
Figure 4B:
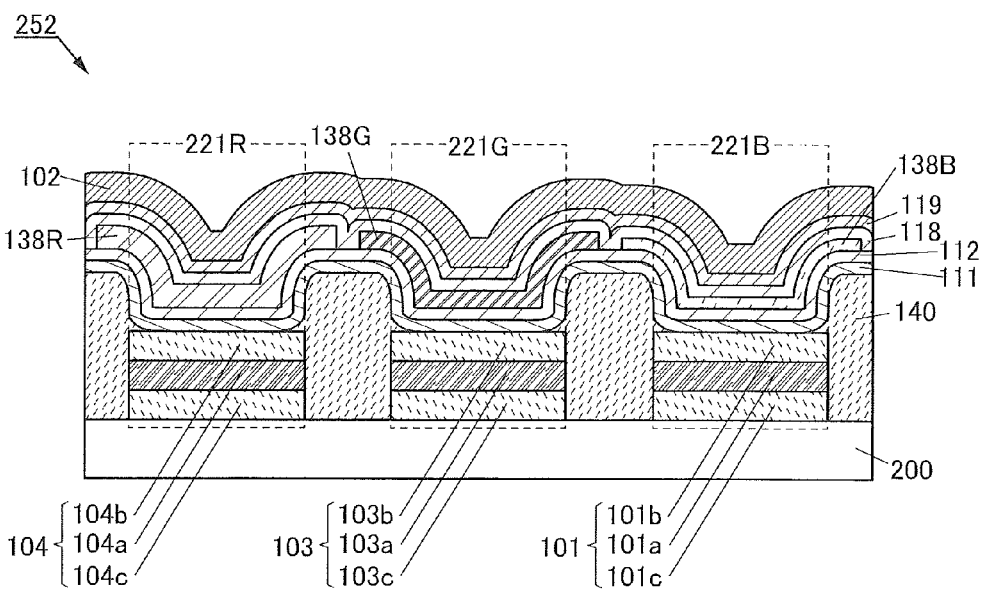

FIGS. 4A and 4B are cross-sectional views each illustrating a light-emitting element of one embodiment of the present invention. In FIGS. 4A and 4B, a portion having a function similar to that in FIGS. 1A and 1B and FIG. 3 is represented by the same hatch pattern as in FIGS. 1A and 1B and FIG. 3 and not especially denoted by a reference numeral in some cases. In addition, common reference numerals are used for portions having similar functions, and a detailed description of the portions is omitted in some cases.

FIGS. 4A and 4B illustrates a structure example of a light-emitting element 250 and a light-emitting element 252 each having a structure different from the structures of the light-emitting elements illustrated in FIGS. 1A and 1B and FIG. 3. Each of the light-emitting elements 250 and 252 illustrated in FIGS. 4A and 4B includes the electrode 101, the electrode 102, an electrode 103, and an electrode 104 over a substrate 200. The electrode 101 includes the conductive layer 101a and the conductive layer 101b over and in contact with the conductive layer 101a. The electrode 103 includes a conductive layer 103a and a conductive layer 103b over and in contact with the conductive layer 103a. The electrode 104 includes a conductive layer 104a and a conductive layer 104b over and in contact with the conductive layer 104a.

The light-emitting element 252 further includes, as part of the electrode 101, a conductive layer 101c under and in contact with the conductive layer 101a. In other words, FIG. 4B illustrates a structure example of the electrode 101 in which the conductive layer 101a is sandwiched by the conductive layer 101b and the conductive layer 101c. The electrode 103 further includes a conductive layer 103c under and in contact with the conductive layer 103a. In other words, FIG. 4B illustrates a structure example of the electrode 103 in which the conductive layer 103a is sandwiched between the conductive layer 103b and the conductive layer 103c. The electrode 104 further includes a conductive layer 104c under and in contact with the conductive layer 104a. In other words, FIG. 4B illustrates a structure example of the electrode 104 in which the conductive layer 104a is sandwiched between the conductive layer 104b and the conductive layer 104c.

In the light-emitting element 252, the conductive layer 101b and the conductive layer 101c may be formed with different materials or the same material. The electrode 101 preferably has a structure in which the conductive layer 101a is sandwiched by the layers formed of the same conductive material, in which case patterning by etching can be performed easily. Similarly, the conductive layer 103b and the conductive layer 103c may be formed with different materials or the same material; and the conductive layer 104b and the conductive layer 104c may be formed with different materials or the same material. Alternatively, the electrode 101, the electrode 103, and the electrode 104 may include different materials or the same material. The electrode 101, the electrode 103, and the electrode 104 preferably include the same conductive material, in which case the manufacturing cost of the light-emitting element 252 can be reduced.

In the light-emitting element 252, the electrode 101 may include one of the conductive layer 101b and the conductive layer 101c; the electrode 103 may include one of the conductive layer 103b and the conductive layer 103c; and the electrode 104 may include one of the conductive layer 104b and the conductive layer 104c.

Each of the light-emitting elements 250 and 252 further includes the hole-injection layer 111, the hole-transport layer 112, a light-emitting layer 138B, the electron-transport layer 118, and the electron-injection layer 119 between the electrode 101 and the electrode 102. Each of the light-emitting elements 250 and 252 further includes the hole-injection layer 111, the hole-transport layer 112, a light-emitting layer 138G, the electron-transport layer 118, and the electron-injection layer 119 between the electrode 102 and the electrode 103. Each of the light-emitting elements 250 and 252 further includes the hole-injection layer 111, the hole-transport layer 112, a light-emitting layer 138R, the electron-transport layer 118, and the electron-injection layer 119 between the electrode 102 and the electrode 104.

In FIGS. 4A and 4B, a partition wall 140 is provided between a region 221B sandwiched between the electrode 101 and the electrode 102, a region 221G sandwiched between the electrode 102 and the electrode 103, and a region 221R sandwiched between the electrode 102 and the electrode 104. The partition wall 140 has an insulating property. The partition wall 140 covers end portions of the electrodes 101, 103, and 104 and has openings overlapping with the electrodes. With the partition wall 140, the electrodes provided over the substrate 200 in the regions can be separated into island shapes like the electrodes 101, 103, and 104.

Note that the light-emitting layer 138B and the light-emitting layer 138G may overlap with each other in a region where they overlap with the partition wall 140. The light-emitting layer 138G and the light-emitting layer 138R may overlap with each other in a region where they overlap with the partition wall 140. The light-emitting layer 138R and the light-emitting layer 138B may overlap with each other in a region where they overlap with the partition wall 140.

The light-emitting layers 138R, 138G, and 138B preferably contain light-emitting materials having functions of emitting light of different colors. When the light-emitting layer 138R contains a light-emitting material having a function of emitting red, the region 221R emits red light. When the light-emitting layer 138G contains a light-emitting material having a function of emitting green, the region 221G emits green light. When the light-emitting layer 138B contains a light-emitting material having a function of emitting blue, the region 221B emits blue light. The light-emitting element 250 or 252 having such a structure is used in a pixel of a display device, whereby a full-color display device can be fabricated.

The guest material contained in the light-emitting layer 138B preferably has a function of converting the triplet excitation energy into light emission. It is preferable that the emission spectrum of the guest material in a dichloromethane solution have a peak in a wavelength region ranging mine from 440 nm to 470 nm and have a full width at half maximum of greater than or equal to 20 nm and less than or equal to 80 nm. The light intensity of the guest material in the dichloromethane solution at a wavelength of 530 nm is preferably greater than or equal to 0% and less than or equal to 50% of the maximum light intensity. The chromaticity y in the CIE 1931 chromaticity coordinates, which is calculated from the emission spectrum of the guest material in the dichloromethane solution, is preferably greater than or equal to 0.01 and less than or equal to 0.3.

By providing a color filter over the electrode through which light is extracted, the color purity of each of the light-emitting elements 250 and 252 can be improved. Therefore, the color purity of a display device including the light-emitting element 250 or 252 can be improved.

By providing a polarizing plate over the electrode through which light is extracted, the reflection of external light by each of the light-emitting elements 250 and 252 can be reduced. Therefore, the contrast ratio of a display device including the light-emitting element 250 or 252 can be improved.

<4. Structure Example 4 of Light-Emitting Element>

Next, structure examples different from the light-emitting element illustrated in FIG. 1A, FIG. 3, and FIGS. 4A and 4B are described below with reference to FIGS. 5A and 5B.

Figure 5A:
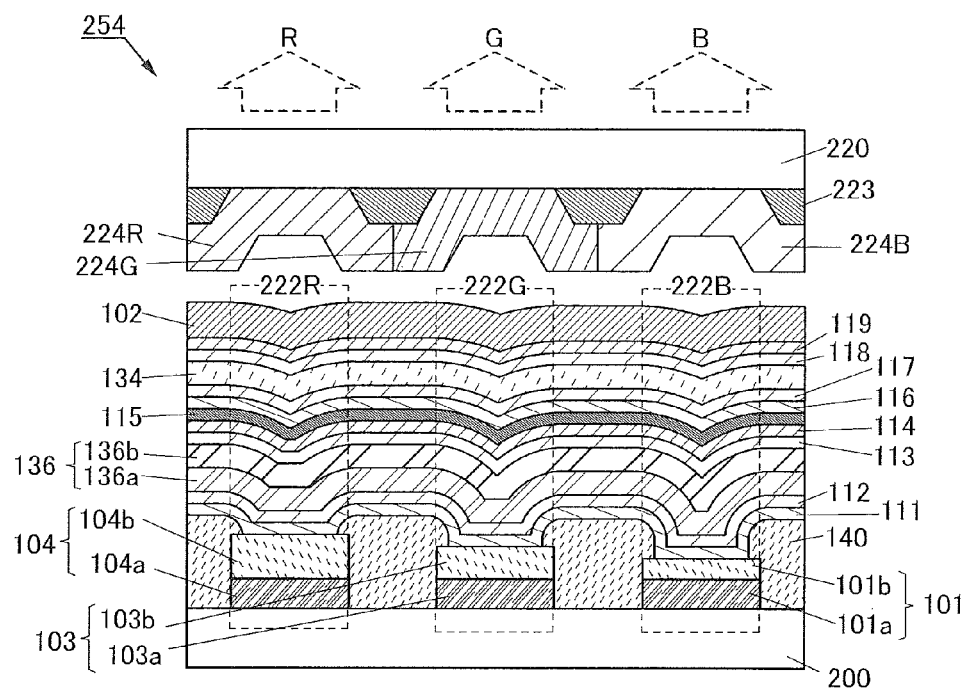
FIGS. 5A and 5B are schematic cross-sectional views each illustrating a light-emitting element of one embodiment of the present invention.
Figure 5B:
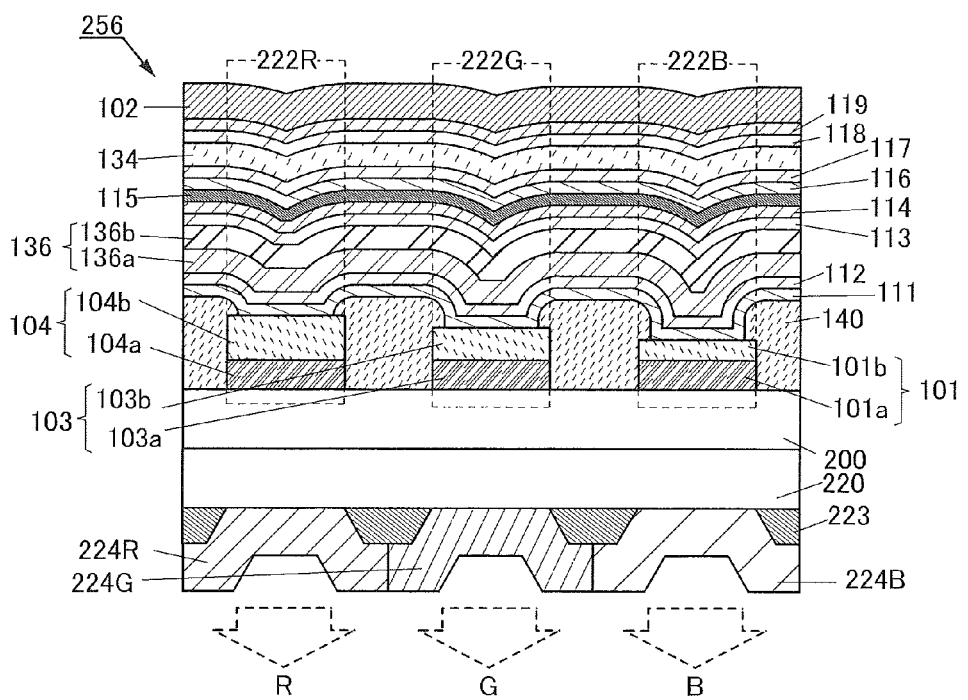

FIGS. 5A and 5B are cross-sectional views each illustrating a light-emitting element of one embodiment of the present invention. In FIGS. 5A and 5B, a portion having a function similar to that in FIG. 1A, FIG. 3, and FIGS. 4A and 4B is represented by the same hatch pattern as in FIG. 1A, FIG. 3, and FIGS. 4A and 4B and not especially denoted by a reference numeral in some cases. In addition, common reference numerals are used for portions having similar functions, and a detailed description of the portions is omitted in some cases.

FIGS. 5A and 5B each illustrate a structure example of a tandem light-emitting element in which a plurality of light-emitting layers are stacked between a pair of electrodes with the charge-generation layer 115 provided between the light-emitting layers. A light-emitting element 254 illustrated in FIG. 5A has a top-emission structure in which light is extracted in a direction opposite to the substrate 200, and a light-emitting element 256 illustrated in FIG. 5B has a bottom-emission structure in which light is extracted to the substrate 200 side. However, one embodiment of the present invention is not limited to these structures and may have a dual-emission structure in which light emitted from the light-emitting element is extracted in both top and bottom directions with respect to the substrate 200 over which the light-emitting element is formed.

The light-emitting elements 254 and 256 each include the electrode 101, the electrode 102, the electrode 103, and an electrode 104 over the substrate 200. The light-emitting layer 134, the charge-generation layer 115, and the light-emitting layer 136 are included between the electrode 101 and the electrode 102, between the electrode 102 and the electrode 103, and between the electrode 102 and the electrode 104. The hole-injection layer 111, the hole-transport layer 112, the electron-transport layer 113, the electron-injection layer 114, the hole-injection layer 116, the hole-transport layer 117, the electron-transport layer 118, and the electron-injection layer 119 are further included.

The electrode 101 includes a conductive layer 101a and a conductive layer 101b over and in contact with the conductive layer 101a. The electrode 103 includes a conductive layer 103a and a conductive layer 103b over and in contact with the conductive layer 103a. The electrode 104 includes a conductive layer 104a and a conductive layer 104b over and in contact with the conductive layer 104a.

In the light-emitting element 254 illustrated in FIG. 5A and the light-emitting element 256 illustrated in FIG. 5B, a partition wall 140 is provided between a region 222B sandwiched between the electrode 101 and the electrode 102, a region 222G sandwiched between the electrode 102 and the electrode 103, and a region 222R sandwiched between the electrode 102 and the electrode 104. The partition wall 140 has an insulating property. The partition wall 140 covers end portions of the electrodes 101, 103, and 104 and has openings overlapping with the electrodes. With the partition wall 140, the electrodes provided over the substrate 200 in the regions can be separated into island shapes like the electrodes 101, 103, and 104.

The light-emitting elements 254 and 256 each include a substrate 220 provided with an optical element 224B, an optical element 224G, and an optical element 224R in the direction in which light emitted from the region 222B, light emitted from the region 222G, and light emitted from the region 222R are extracted. The light emitted from each region is emitted outside the light-emitting element through each optical element. In other words, the light from the region 222B, the light from the region 222G, and the light from the region 222R are emitted through the optical element 224B, the optical element 224G, and the optical element 224R, respectively.

The optical elements 224B, 224G, and 224R each have a function of selectively transmitting light of a particular color out of incident light. For example, the light emitted from the region 222B through the optical element 224B is blue light, the light emitted from the region 222G through the optical element 224G is green light, and the light emitted from the region 222R through the optical element 224R is red light.

Note that in FIGS. 5A and 5B, blue light (B), green light (G), and red light (R) emitted from the regions through the optical elements are schematically illustrated by arrows of dashed lines.

A light-blocking layer 223 is provided between the optical elements. The light-blocking layer 223 has a function of blocking light emitted from the adjacent regions. Note that a structure without the light-blocking layer 223 may also be employed.

Furthermore, the light-emitting elements 254 and 256 each have a microcavity structure.

Light emitted from the light-emitting layers 134 and 136 resonates between a pair of electrodes (e.g., the electrode 101 and the electrode 102). In each of the light-emitting elements 254 and 256, the thicknesses of the conductive layers (the conductive layer 101b, the conductive layer 103b, and the conductive layer 104b) in each region are adjusted, so that light at a desired wavelength emitted from the light-emitting layers 134 and 136 can be intensified. Note that the thickness of at least one of the hole-injection layer 111 and the hole-transport layer 112 may differ between the regions to intensify light at a desired wavelength emitted from the light-emitting layers 134 and 136.

For example, in the case where the refractive index of the conductive material having a function of reflecting light in the electrodes 101 to 104 is lower than the refractive index of the light-emitting layer 134 or 136, the thickness of the conductive layer 101b of the electrode 101 is adjusted so that the optical distance between the reflective region of the electrode 101 and the reflective region of the electrode 102 is $m_B \lambda_B / 2$ ($m_B$ is a natural number and $\lambda_B$ is the wavelength of desired light in the region 222B). Similarly, the thickness of the conductive layer 103b of the electrode 103 is adjusted so that the optical distance between the electrode 103 and the electrode 102 is $m_G \lambda_G / 2$ ($m_G$ is a natural number and $\lambda_G$ is the wavelength of desired light in the region 222G). Furthermore, the thickness of the conductive layer 104b of the electrode 104 is adjusted so that the optical distance between the reflective region of the electrode 104 and the reflective region of the electrode 102 is $m_R \lambda_R / 2$ ($m_R$ is a natural number and $\lambda_R$ is the wavelength of desired light in the region 222R).

In the above manner, with the microcavity structure, in which the optical path length between the electrodes in the respective regions is adjusted, scattering and absorption of light in the vicinity of the electrodes can be suppressed, resulting in high light extraction efficiency. In the above structure, each of the conductive layers 101b, 103b, and 104b preferably has a function of transmitting light. The materials of the conductive layers 101b, 103b, and 104b may be the same or different. Each of the conductive layers 101b, 103b, and 104b may have a stacked structure of two or more layers.

Note that since the light-emitting element 254 illustrated in FIG. 5A has a top-emission structure, it is preferable that the conductive layer 101a, the conductive layer 103a, and the conductive layer 104a have a function of reflecting light. In addition, it is preferable that the electrode 102 have functions of transmitting light and reflecting light.

Since the light-emitting element 256 illustrated in FIG. 5B has a bottom-emission structure, it is preferable that the conductive layer 101a, the conductive layer 103a, and the conductive layer 104a have functions of transmitting light and reflecting light. In addition, it is preferable that the electrode 102 have a function of reflecting light.

In each of the light-emitting elements 254 and 256, the conductive layers 101a, 103a, and 104a may be formed with different materials or the same material. When the conductive layers 101a, 103a, and 104a are formed with the same material, manufacturing cost of the light-emitting elements 254 and 256 can be reduced. Note that each of the conductive layers 101a, 103a, and 104a may have a stacked-layer structure including two or more layers.

The light-emitting layers 134 and 136 can each have a stacked-layer structure of two layers, for example, the light-emitting layer 136a and the light-emitting layer 136b. Two kinds of light-emitting materials (the first material and the second material) having functions of emitting light of different colors are used for the two light-emitting layers, so that light of a plurality of emission colors can be obtained at the same time. It is particularly preferable to select light-emitting materials so that white light can be obtained by combining light emission from the light-emitting layers 134 and 136.

The light-emitting layer 134 or 136 may have a structure in which three or more layers are stacked or may include a layer having no light-emitting material.

One of the light-emitting layer 134 and the light-emitting layer 136 contains a guest material having a function of converting the triplet excitation energy into light emission. The emission spectrum of the guest material in a dichloromethane solution has a peak in a wavelength region ranging from 440 nm to 470 nm and has a full width at half maximum of greater than or equal to 20 nm and less than or equal to 80 nm. Therefore, light emitted from the region 222B in each of the light-emitting elements 254 and 256 can be light of significantly deep blue with a chromaticity y (the CIE 1931 chromaticity coordinates) greater than or equal to 0.01 and less than or equal to 0.06 at a high current efficiency greater than or equal to 3 cd/A, light of excellent blue with a chromaticity y greater than 0.06 and less than or equal to 0.08 at a high current efficiency greater than or equal to 8 cd/A, or light of favorable blue with a chromaticity y greater than 0.08 and less than or equal to 0.1 at a high current efficiency greater than or equal to 10 cd/A. Alternatively, in at least one of the light-emitting layers 134 and 136, the light intensity of the guest material in the dichloromethane solution at a wavelength of 530 nm is preferably greater than or equal to 0% and less than or equal to 50% of the maximum light intensity. Alternatively, the chromaticity y in the CIE 1931 chromaticity coordinates, which is calculated from the emission spectrum of the guest material in the dichloromethane solution, is preferably greater than or equal to 0.01 and less than or equal to 0.3.

<5. Components of Light-Emitting Element>

Components of the light-emitting elements illustrated in FIGS. 1A and 1B, FIGS. 2A and 2B, FIG. 3, FIGS. 4A and 4B, and FIGS. 5A and 5B are described in detail below.

<<Substrate>>

For the substrate over which the light-emitting element of one embodiment of the present invention can be formed and which can include an optical element, glass, quartz, plastic, or the like can be used, for example. Alternatively, a flexible substrate can be used. The flexible substrate means a substrate that can be bent, such as a plastic substrate made of polycarbonate or polyarylate, for example. Alternatively, a film, an inorganic vapor deposition film, or the like can be used. Another material may be used as long as the substrate functions as a support in a manufacturing process of the light-emitting elements or a display device. Another material having a function of protecting the light-emitting elements or the optical elements may be used.

Note that in this specification and the like, a light-emitting element or a transistor can be formed using any of a variety of substrates, for example. The type of a substrate is not limited to a certain type. Examples of the substrate include a semiconductor substrate (e.g., a single crystal substrate or a silicon substrate), an SOI substrate, a glass substrate, a quartz substrate, a plastic substrate, a metal substrate, a stainless steel substrate, a substrate including stainless steel foil, a tungsten substrate, a substrate including tungsten foil, a flexible substrate, an attachment film, paper including a fibrous material, a base material film, and the like. As an example of a glass substrate, a barium borosilicate glass substrate, an aluminoborosilicate glass substrate, a soda lime glass substrate, and the like can be given. Examples of the flexible substrate, the attachment film, the base film, and the like are substrates of plastics typified by polyethylene terephthalate (PET), polyethylene naphthalate (PEN), polyether sulfone (PES), and polytetrafluoroethylene (PTFE). Another example is a resin such as acrylic. Furthermore, polypropylene, polyester, polyvinyl fluoride, and polyvinyl chloride can be given as examples. Other examples are polyamide, polyimide, aramid, epoxy, an inorganic vapor deposition film, paper, and the like. Specifically, the use of semiconductor substrates, single crystal substrates, SOI substrates, or the like enables the manufacture of small-sized transistors with a small variation in characteristics, size, shape, or the like and with high current capability. A circuit using such transistors achieves lower power consumption of the circuit or higher integration of the circuit.

Alternatively, a flexible substrate may be used as the substrate such that the light-emitting element and the transistor is provided directly on the flexible substrate. Further alternatively, a separation layer may be provided between the substrate and the transistor or the substrate and the light-emitting element. The separation layer can be used when part or the whole of a display device formed over the separation layer is separated from the substrate and transferred onto another substrate. In such a case, the light-emitting element and the transistor can be transferred to a substrate having low heat resistance or a flexible substrate as well. For the above separation layer, a stack including inorganic films, which are a tungsten film and a silicon oxide film, or a structure in which a resin film of polyimide or the like is formed over a substrate can be used, for example.

In other words, after the light-emitting element and the transistor are formed using a substrate, the light-emitting element and the transistor may be transferred to another substrate. Example of the substrate to which the light-emitting element and the transistor are transferred are, in addition to the above substrate over which the light-emitting element and the transistor can be formed, a cellophane substrate, a stone substrate, a wood substrate, a cloth substrate (including a natural fiber (e.g., silk, cotton, or hemp), a synthetic fiber (e.g., nylon, polyurethane, or polyester), a regenerated fiber (e.g., acetate, cupra, rayon, or regenerated polyester), and the like), a leather substrate, a rubber substrate, and the like. When such a substrate is used, a transistor with excellent properties or a transistor with low power consumption can be formed, a display device with high durability can be formed, high heat resistance can be provided, or reduction in weight or thickness can be achieved.

<<Pair of Electrodes>>

The electrodes 101, 103, and 104 each function as an anode or a cathode of the light-emitting element. Note that the conductive layer 101a and the conductive layer 101b included in the electrode 101 are described below, and the structure and material of the conductive layer 101a and the conductive layer 101b can be applied to the conductive layer 103a and the conductive layer 103b included in the electrode 103 and the conductive layer 104a and the conductive layer 104b included in the electrode 104. In addition, the structure and material of the conductive layer 101b can be applied to the conductive layer 101c, the conductive layer 103c, and the conductive layer 104c.

The conductive layer 101a of the electrode 101 is preferably foil led using a conductive material having a function of reflecting light. Examples of the conductive material include aluminum (Al), an alloy containing Al, and the like. Examples of the alloy containing Al include an alloy containing Al and L (L represents one or more of titanium (Ti), neodymium (Nd), nickel (Ni), and lanthanum (La)), and the like. Aluminum has low resistance and high light reflectivity. Aluminum is included in earth's crust in large amount and is inexpensive; therefore, it is possible to reduce costs for manufacturing a light-emitting element with aluminum. Alternatively, Ag, an alloy of silver (Ag) and N (N represents one or more of yttrium (Y), Nd, Mg, Al, Ti, gallium (Ga), zinc (Zn), indium (In), tungsten (W), manganese (Mn), tin (Sn), iron (Fe), Ni, copper (Cu), palladium (Pd), iridium (Ir), or gold (Au)), or the like can be used. Examples of the alloy containing silver include an alloy containing silver, palladium, and copper, an alloy containing silver and copper, an alloy containing silver and magnesium, an alloy containing silver and nickel, an alloy containing silver and gold, and the like. Note that in the case where light is extracted through the electrode 101, a metal thin film having a thickness that allows transmission of light (greater than or equal to 5 nm and less than or equal to 30 nm) can be used as the conductive layer 101a.

The conductive layer 101b having a function of transmitting light can be formed using, for example, indium tin oxide (hereinafter, referred to as ITO), indium tin oxide containing silicon or silicon oxide (ITSO), indium oxide-zinc oxide (indium zinc oxide), indium oxide containing tungsten oxide and zinc oxide, or the like. In particular, in the case where the electrode 101 is used as an anode, the conductive layer 101b is preferably formed using a material having a high work function (higher than or equal to 4.0 eV). The conductive layer 101b can be formed by a sputtering method, an evaporation method, a printing method, a coating method, a molecular beam epitaxy (MBE) method, a chemical vapor deposition (CVD) method, a pulsed laser deposition method, an atomic layer deposition (ALD) method, or the like as appropriate.

The conductive layer 101b can have a function of adjusting the optical path length so that light at a desired wavelength emitted from each light-emitting layer resonates and is intensified.

In this specification and the like, a conductive layer having a function of transmitting light transmits visible light and has conductivity. Examples of the transparent conductive layer include, in addition to the above-described oxide conductor layer typified by an ITO, an oxide semiconductor layer and an organic conductor layer containing an organic substance. Examples of the organic conductive layer containing an organic substance include a layer containing a composite material in which an organic compound and an electron donor (donor) are mixed and a layer containing a composite material in which an organic compound and an electron acceptor (acceptor) are mixed. The resistivity of the transparent conductive layer is preferably lower than or equal to $1\times10^5$ Ω·cm, further preferably lower than or equal to $1\times10^4$ Ω·cm.

The electrode 102 functions as an anode or a cathode of each light-emitting element. Note that in the case where the electrode 101 has a function of reflecting light, the electrode 102 is preferably formed using a conductive material having a function of transmitting light. As the conductive material, a conductive material having a visible light transmittance higher than or equal to 40% and lower than or equal to 100%, preferably higher than or equal to 60% and lower than or equal to 100%, and a resistivity lower than or equal to $1\times10^{-2}$ Ω·cm can be used. The electrode 102 may be formed using a conductive material having functions of transmitting light and reflecting light. As the conductive material, a conductive material having a visible light reflectivity higher than or equal to 20% and lower than or equal to 80%, preferably higher than or equal to 40% and lower than or equal to 70%, and a resistivity lower than or equal to $1\times10^{-2}$ Ω·cm can be used. The electrode 102 can be formed using one or more kinds of conductive metals and alloys, conductive compounds, and the like. For example, ITO, ITSO, indium oxide-zinc oxide (indium zinc oxide), indium oxide-tin oxide containing titanium, indium titanium oxide, indium oxide containing tungsten oxide and zinc oxide, or the like can be used. A metal thin film having a thickness that allows transmission of light (preferably, approximately greater than or equal to 5 nm and less than or equal to 30 nm) can also be used. As the metal, for example, Ag, an alloy of Ag and Al, an alloy of Ag and Mg, an alloy of Ag and Au, an alloy of Ag and ytterbium (Yb), or the like can be used. Particularly when the electrode 102 functions as a cathode, a material containing at least one of Ag and Mg is preferably used. In addition, it is preferable to use a material having a low work function (3.8 eV or less). The examples include an element belonging to Group 1 or 2 of the periodic table (e.g., an alkali metal such as lithium or cesium, an alkaline earth metal such as calcium or strontium, or magnesium), an alloy containing any of these elements (e.g., Ag—Mg or Al—Li), a rare earth metal such as europium (Eu) or Yb, an alloy containing any of these rare earth metals, an alloy containing aluminum and silver, and the like. The electrode 102 can be formed by a sputtering method, an evaporation method, a printing method, a coating method, or the like.

<<Light-Emitting Layer>>

In each of the light-emitting layer 130, the light-emitting layer 134, and the light-emitting layer 136, the weight percentage of the host material is larger than that of the guest material, and the guest material is dispersed in the host material.

<<Guest Material>>

As the guest material in the light-emitting layer 130, the light-emitting layer 134, and the light-emitting layer 136, it is preferable to use a substance which has a function of converting the triplet excitation energy into light emission, and the emission spectrum of which in a dichloromethane solution has a maximum value (a peak) in a wavelength region ranging from 440 nm to 470 nm and has a full width at half maximum of greater than or equal to 20 nm and less than or equal to 80 nm. The light intensity of the substance in the dichloromethane solution at a wavelength of 530 nm is preferably greater than or equal to 0% and less than or equal to 50% of the maximum light intensity. The chromaticity y in the CIE 1931 chromaticity coordinates, which is calculated from the emission spectrum, is preferably greater than or equal to 0.01 and less than or equal to 0.3.

Examples of the guest material include tris{2-[4-(2-adamantyl)-5-methyl-4H-1,2,4-triazol-3-yl-κN2]phenyl-κC}iridium(III) (abbreviation: Ir(Mptz-Adm2)$_3$), and tris(1,3-dimethyl-5-phenyl-1H-1,2,4-triazolato)iridium(III) (abbreviation: Ir(Mptz1-Me)$_3$). Note that the guest material that can be used for the light-emitting element of one embodiment of the present invention is not limited to these.

The light-emitting layer 130, the light-emitting layer 134, or the light-emitting layer 136 may contain a light-emitting material having a function of emitting at least one of violet light, blue light, and blue green light or a light-emitting material having a function of emitting at least one of green light, yellow green light, yellow light, orange light, and red light. In addition, each of the light-emitting layers preferably contains an electron-transport material and/or a hole-transport material as a host material in addition to the guest material that is a light-emitting material.

As the light-emitting material, a light-emitting material having a function of converting the singlet excitation energy into light emission or a light-emitting material having a function of converting the triplet excitation energy into light emission can be used. Examples of the light-emitting materials are given below.

Examples of the light-emitting material that converts singlet excitation energy into light emission include substances that emit fluorescence. For example, any of the following substances having an anthracene skeleton, a tetracene skeleton, a chrysene skeleton, a phenanthrene skeleton, a pyrene skeleton, a perylene skeleton, a stilbene skeleton, an acridonoe skeleton, a coumarin skeleton, a phenoxazine skeleton, a phenothiazine skeleton, or the like can be used: 5,6-bis[4-(10-phenyl-9-anthryl)phenyl]-2,2'-bipyridine (abbreviation: PAP2BPy), 5,6-bis[4'-(10-phenyl-9-anthryl)biphenyl-4-yl]-2,2'-bipyridine (abbreviation: PAPP2BPy), N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), 4-(10-phenyl-9-anthryl)-4'-(9-phenyl-9H-carbazol-3-yl)triphenylamine (abbreviation: PCBAPA), 4-[4-(10-phenyl-9-anthryl)phenyl]-4'-(9-phenyl-9H-carbazol-3-yl)triphenylamine (abbreviation: PCBAPBA), perylene, 2,5,8,11-tetra(tert-butyl)perylene (abbreviation: TBP), N,N'-diphenyl-N,N'-bis[4-(9-phenyl-9H-fluoren-9-yl)phenyl]pyrene-1,6-diamine (abbreviation: 1,6FLPAPrn), N,N'-bis(3-methylphenyl)-N,N'-bis[3-(9-phenyl-9H-fluoren-9-yl)phenyl]-pyrene-1,6-diamine (abbreviation: 1,6mMemFLPAPrn), N,N'''-(2-tert-butylanthracene-9,10-diyldi-4,1-phenylene)bis[N,N',N'-triphenyl-1,4-phenylenediamine] (abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N',N'-triphenyl-1,4-phenylenediamine (abbreviation: 2DPAPPA), N,N,N',N',N'',N'',N''',N'''-octaphenyldibenzo[g,p]chrysene-2,7,10,15-tetraamine (abbreviation: DBC1), coumarin 30, N-(9,10-diphenyl-2-anthryl)-N,9-diphenyl-9H-carbazol-3-amine (abbreviation: 2PCAPA), N-(9,10-diphenyl-2-anthryl)-N,N',N'-triphenyl-1,4-phenylenediamine (abbreviation: 2DPAPA), N,N,9-triphenylanthracen-9-amine (abbreviation: DPhAPhA), coumarin 6, coumarin 545T, N,N'-diphenylquinacridone (abbreviation: DPQd), rubrene, 5,12-bis(1,1'-biphenyl-4-yl)-6,11-diphenyltetracene (abbreviation: BPT), 2-(2-{2-[4-(dimethylamino)phenyl]ethenyl}-6-methyl-4H-pyran-4-ylidene)propanedinitrile (abbreviation: DCM1), 2-{2-methyl-6-[2-(2,3,6,7-tetrahydro-1H,5H-benzo[ij]quinolizin-9-yl)ethenyl]-4H-pyran-4-ylidene}propanedinitrile (abbreviation: DCM2), N,N,N',N'-tetrakis(4-methylphenyl)tetracene-5,11-diamine (abbreviation: p-mPhTD), 7,14-diphenyl-N,N,N',N'-tetrakis(4-methylphenyl)acenaphtho[1,2-a]fluoranthene-3,10-diamine (abbreviation: p-mPhAFD), 2-{2-isopropyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTI), 2-{2-tert-butyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTB), 2-(2,6-bis{2-[4-(dimethylamino)phenyl]ethenyl}-4H-pyran-4-ylidene)propanedinitrile (abbreviation: BisDCM), 2-{2,6-bis[2-(8-methoxy-1,1,7,7-tetramethyl-2,3,6,7-tetrahydro-1H,5H-benzo[ij]quinolizin-9-yl)ethenyl]-4H-pyran-4-ylidene}propanedinitrile (abbreviation: BisDCJTM), and 5,10,15,20-tetraphenylbisbenzo[5,6]indeno[1,2,3-cd: 1',2',3'-lm]perylene.

Examples of the light-emitting material that converts triplet excitation energy into light emission include substances that emit phosphorescence.

Examples of the substance that has an emission peak in the blue or green wavelength range include organometallic iridium complexes having 4H-triazole skeletons, such as tris{2-[5-(2-methylphenyl)-4-(2,6-dimethylphenyl)-4H-1,2,4-triazol-3-yl-κN2]phenyl-κC}iridium(III) (abbreviation: Ir(mpptz-dmp)$_3$), tris(5-methyl-3,4-diphenyl-4H-1,2,4-triazolato)iridium(III) (abbreviation: Ir(Mptz)$_3$), tris[4-(3-biphenyl)-5-isopropyl-3-phenyl-4H-1,2,4-triazolato]iridium(III) (abbreviation: Ir(iPrptz-3b)$_3$), and tris[3-(5-biphenyl)-5-isopropyl-4-phenyl-4H-1,2,4-triazolato]iridium(III) (abbreviation: Ir(iPr5btz)$_3$); organometallic iridium complexes having 1H-triazole skeletons, such as tris[3-methyl-1-(2-methylphenyl)-5-phenyl-1H-1,2,4-triazolato]iridium(III) (abbreviation: Ir(Mptz1-mp)$_3$) and tris(1-methyl-5-phenyl-3-propyl-1H-1,2,4-triazolato)iridium(III) (abbreviation: Ir(Prptz1-Me)$_3$); organometallic iridium complexes having imidazole skeletons, such as fac-tris[1-(2,6-diisopropylphenyl)-2-phenyl-1H-imidazole]iridium(III) (abbreviation: Ir(iPrpmi)$_3$) and tris[3-(2,6-dimethylphenyl)-7-methylimidazo[1,2-f]phenanthridinato]iridium(III) (abbreviation: Ir(dmpimpt-Me)$_3$); and organometallic iridium complexes in which a phenylpyridine derivative having an electron-withdrawing group is a ligand, such as bis[2-(4',6'-difluorophenyl)pyridinato-N,C$^{2'}$]iridium(III) tetrakis(1-pyrazolyl)borate (abbreviation: FIr6), bis[2-(4',6'-difluorophenyl)pyridinato-N,C$^{2'}$]iridium(III) picolinate (abbreviation: FIrpic), bis{2-[3',5'-bis(trifluoromethyl)phenyl]pyridinato-N,C$^{2'}$}iridium(III)picolinate (abbreviation: Ir(CF$_3$ppy)$_2$(pic)), and bis[2-(4',6'-difluorophenyl)pyridinato-N,C$^{2'}$]iridium(III) acetylacetonate (abbreviation: FIr(acac)). Among the materials given above, the organometallic iridium complex having a 4H-triazole skeleton has high reliability and high emission efficiency and is thus especially preferable.

Examples of the substance that has an emission peak in the green or yellow wavelength range include organometallic iridium complexes having pyrimidine skeletons, such as tris(4-methyl-6-phenylpyrimidinato)iridium(III) (abbreviation: Ir(mppm)$_3$), tris(4-t-butyl-6-phenylpyrimidinato)

iridium(III) (abbreviation: Ir(tBuppm)₃), (acetylacetonato)bis(6-methyl-4-phenylpyrimidinato)iridium(III) (abbreviation: Ir(mppm)₂(acac)), (acetylacetonato)bis(6-tert-butyl-4-phenylpyrimidinato)iridium(III) (abbreviation: Ir(tBuppm)₂(acac)), (acetylacetonato)bis[4-(2-norbornyl)-6-phenylpyrimidinato]iridium(III) (abbreviation: Ir(nbppm)₂(acac)), (acetylacetonato)bis[5-methyl-6-(2-methylphenyl)-4-phenylpyrimidinato]iridium(III) (abbreviation: Ir(mpmppm)₂(acac)), (acetylacetonato)bis{4,6-dimethyl-2-[6-(2,6-dimethylphenyl)-4-pyrimidinyl-κN3]phenyl-κC}iridium(III) (abbreviation: Ir(dmppm-dmp)₂(acac)), (acetylacetonato)bis(4,6-diphenylpyrimidinato)iridium(III) (abbreviation: Ir(dppm)₂(acac)); organometallic iridium complexes having pyrazine skeletons, such as (acetylacetonato)bis(3,5-dimethyl-2-phenylpyrazinato)iridium(III) (abbreviation: Ir(mppr-Me)₂(acac)) and (acetylacetonato)bis(5-isopropyl-3-methyl-2-phenylpyrazinato)iridium(III) (abbreviation: Ir(mppr-iPr)₂(acac)); organometallic iridium complexes having pyridine skeletons, such as tris(2-phenylpyridinato-N,C²')iridium(III) (abbreviation: Ir(ppy)₃), bis(2-phenylpyridinato-N,C²')iridium(III) acetylacetonate (abbreviation: Ir(ppy)₂(acac)), bis(benzo[h]quinolinato)iridium(III) acetylacetonate (abbreviation: Ir(bzq)₂(acac)), tris(benzo[h]quinolinato)iridium(III) (abbreviation: Ir(bzq)₃), tris(2-phenylquinolinato-N,C²')iridium(III) (abbreviation: Ir(pq)₃), and bis(2-phenylquinolinato-N,C²')iridium(III) acetylacetonate (abbreviation: Ir(pq)₂(acac)); organometallic iridium complexes such as bis(2,4-diphenyl-1,3-oxazolato-N,C²')iridium(III)acetylacetonate (abbreviation: Ir(dpo)₂(acac)), bis{2[4'-(perfluorophenyl)phenyl]pyridinato-N,C²'}iridium(III)acetylacetonate (abbreviation: Ir(p-PF-ph)₂(acac)), and bis(2-phenylbenzothiazolato-N,C²')iridium(III)acetylacetonate (abbreviation: Ir(bt)₂(acac)); and a rare earth metal complex such as tris(acetylacetonato)(monophenanthroline)terbium(III) (abbreviation: Tb(acac)₃(Phen)). Among the materials given above, the organometallic iridium complex having a pyrimidine skeleton has distinctively high reliability and emission efficiency and is thus particularly preferable.

Examples of the substance that has an emission peak in the yellow or red wavelength range include organometallic iridium complexes having pyrimidine skeletons, such as (diisobutyrylmethanato)bis[4,6-bis(3-methylphenyl)pyrimidinato]iridium(III) (abbreviation: Ir(5mdppm)₂(dibm)), bis[4,6-bis(3-methylphenyl)pyrimidinato](dipivaloylmethanato)iridium(III) (abbreviation: Ir(5mdppm)₂(dpm)), and bis[4,6-di(naphthalen-1-yl)pyrimidinato](dipivaloylmethanato)iridium(III) (abbreviation: Ir(d1npm)₂(dpm)); organometallic iridium complexes having pyrazine skeletons, such as (acetylacetonato)bis(2,3,5-triphenylpyrazinato)iridium(III) (abbreviation: Ir(tppr)₂(acac)), bis(2,3,5-triphenylpyrazinato)(dipivaloylmethanato)iridium(III) (abbreviation: Ir(tppr)₂(dpm)), and (acetylacetonato)bis[2,3-bis(4-fluorophenyl)quinoxalinato]iridium(III) (abbreviation: Ir(Fdpq)₂(acac)); organometallic iridium complexes having pyridine skeletons, such as tris(1-phenylisoquinolinato-N,C²')iridium(III) (abbreviation: Ir(piq)₃) and bis(1-phenylisoquinolinato-N,C²')iridium(III)acetylacetonate (abbreviation: Ir(piq)₂(acac)); a platinum complex such as 2,3,7,8,12,13,17,18-octaethyl-21H,23H-porphyrin platinum(II) (abbreviation: PtOEP); and rare earth metal complexes such as tris(1,3-diphenyl-1,3-propanedionato)(monophenanthroline)europium (III) (abbreviation: Eu(DBM)₃(Phen)) and tris[1-(2-thenoyl)-3,3,3-trifluoroacetonato](monophenanthroline)europium (III) (abbreviation: Eu(TTA)₃(Phen)). Among the materials given above, the organometallic iridium complex having a pyrimidine skeleton has distinctively high reliability and emission efficiency and is thus particularly preferable. Further, the organometallic iridium complexes having pyrazine skeletons can provide red light emission with favorable chromaticity.

<<Host Material>>

Although there is no particular limitation on a material that can be used as a host material of the light-emitting layer, for example, any of the following substances can be used for the host material: metal complexes such as tris(8-quinolinolato)aluminum(III) (abbreviation: Alq), tris(4-methyl-8-quinolinolato)aluminum(III) (abbreviation: Almq₃), bis(10-hydroxybenzo[h]quinolinato)beryllium(II) (abbreviation: BeBq₂), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), and bis[2-(2-benzothiazolyl)phenolato]zinc(II) (abbreviation: ZnBTZ); heterocyclic compounds such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), 2,2',2''-(1,3,5-benzenetriyl)tris(1-phenyl-1H-benzimidazole) (abbreviation: TPBI), bathophenanthroline (abbreviation: Bphen), bathocuproine (abbreviation: BCP), and 9-[4-(5-phenyl-1,3,4-oxadiazol-2-yl)phenyl]-9H-carbazole (abbreviation: CO11); and aromatic amine compounds such as NPB, TPD, and BSPB. In addition, condensed polycyclic aromatic compounds such as anthracene derivatives, phenanthrene derivatives, pyrene derivatives, chrysene derivatives, and dibenzo[g,p]chrysene derivatives can be used. Specific examples of the condensed polycyclic aromatic compound include 9,10-diphenylanthracene (abbreviation: DPAnth), N,N-diphenyl-9-[4-(10-phenyl-9-anthryl)phenyl]-9H-carbazol-3-amine (abbreviation: CzA1PA), 4-(10-phenyl-9-anthryl)triphenylamine (abbreviation: DPhPA), YGAPA, PCAPA, N,9-diphenyl-N-{4-[4-(10-phenyl-9-anthryl)phenyl]phenyl}-9H-carbazol-3-amine (abbreviation: PCAPBA), 2PCAPA, 6,12-dimethoxy-5,11-diphenylchrysene, DBC1, 9-[4-(10-phenyl-9-anthracenyl)phenyl]-9H-Carbazole (abbreviation: CzPA), 3,6-diphenyl-9-[4-(10-phenyl-9-anthryl)phenyl]-9H-carbazole (abbreviation: DPCzPA), 9,10-bis(3,5-diphenylphenyl)anthracene (abbreviation: DPPA), 9,10-di(2-naphthyl)anthracene (abbreviation: DNA), 2-tert-butyl-9,10-di(2-naphthyl)anthracene (abbreviation: t-BuDNA), 9,9'-bianthryl (abbreviation: BANT), 9,9'-(stilbene-3,3'-diyl)diphenanthrene (abbreviation: DPNS), 9,9'-(stilbene-4,4'-diyl)diphenanthrene (abbreviation: DPNS2), 1,3,5-tri(1-pyrenyl)benzene (abbreviation: TPB3), and the like. One or more substances having a wider energy gap than the above-described light-emitting material is preferably selected from these substances and a variety of substances. Moreover, in the case where the light-emitting material emits phosphorescence, a substance having triplet excitation energy (energy difference between a ground state and a triplet excited state) which is higher than that of the light-emitting material is preferably selected as the host material.

In the case where a plurality of materials are used as the host material of the light-emitting layer, it is preferable to use a combination of two kinds of compounds which form an exciplex. In this case, a variety of carrier-transport materials can be used as appropriate. In order to form an exciplex efficiently, it is particularly preferable to combine a material which easily accepts electrons (a material having an electron-transport property) and a material which easily accepts holes (a material having a hole-transport property).

This is because in the case where the combination of a material having an electron-transport property and a material having a hole-transport property which form an exciplex is used as a host material, the carrier balance between holes and electrons in the light-emitting layer can be easily optimized by adjustment of the mixture ratio of the material having an electron-transport property and the material having a hole-transport property. The optimization of the carrier balance between holes and electrons in the light-emitting layer can prevent a region in which electrons and holes are recombined from existing on one side in the light-emitting layer. By preventing the region in which electrons and holes are recombined from existing on one side, the reliability of the light-emitting element can be improved.

As the material which easily accepts electrons (the material having an electron-transport property), a π-electron deficient heteroaromatic compound such as a nitrogen-containing heteroaromatic compound, a metal complex, or the like can be used. Specific examples include metal complexes such as bis(10-hydroxybenzo[h]quinolinato)beryllium(II) (abbreviation: $BeBq_2$), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), and bis[2-(2-benzothiazolyl)phenolato]zinc(II) (abbreviation: ZnBTZ); heterocyclic compounds having azole skeletons, such as 2-(4-biphenylyl)-5-(4-tert-butylphenyl)-1,3,4-oxadiazole (abbreviation: PBD), 3-(4-biphenylyl)-4-phenyl-5-(4-tert-butylphenyl)-1,2,4-triazole (abbreviation: TAZ), 1,3-bis[5-(p-tert-butylphenyl)-1,3,4-oxadiazol-2-yl]benzene (abbreviation: OXD-7), 9-[4-(5-phenyl-1,3,4-oxadiazol-2-yl)phenyl]-9H-carbazole (abbreviation: CO11), 2,2',2"-(1,3,5-benzenetriyl)tris(1-phenyl-1H-benzimidazole) (abbreviation: TPBI), and 2-[3-(dibenzothiophen-4-yl)phenyl]-1-phenyl-1H-benzimidazole (abbreviation: mDBTBIm-II); heterocyclic compounds having diazine skeletons, such as 2[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[3'-(9H-carbazol-9-yl)biphenyl-3-yl]dibenzo[f,h]quinoxaline (abbreviation: 2mCzBPDBq), 2-[4-(3,6-diphenyl-9H-carbazol-9-yl)phenyl]dibenzo[f,h]quinoxaline (abbreviation: 2CzPDBq-III), 7-[3-(dibenzothiophen-4-yl)phenyl]dibenzo[f,h]quinoxaline (abbreviation: 7mDBTPDBq-II), 6-[3-(dibenzothiophen-4-yl)phenyl]dibenzo[f,h]quinoxaline (abbreviation: 6mDBTPDBq-II), 4,6-bis[3-(phenanthren-9-yl)phenyl]pyrimidine (abbreviation: 4,6mPnP2Pm), 4,6-bis[3-(4-dibenzothienyl)phenyl]pyrimidine (abbreviation: 4,6mDBTP2Pm-II), and 4,6-bis[3-(9H-carbazol-9-yl)phenyl]pyrimidine (abbreviation: 4,6mCzP2Pm); a heterocyclic compound having a triazine skeleton, such as 2-{4-[3-(N-phenyl-9H-carbazol-3-yl)-9H-carbazol-9-yl]phenyl}-4,6-diphenyl-1,3,5-triazine (abbreviation: PCCzPTzn); and heterocyclic compounds having pyridine skeletons, such as 3,5-bis[3-(9H-carbazol-9-yl)phenyl]pyridine (abbreviation: 35DCzPPy) and 1,3,5-tri[3-(3-pyridyl)phenyl]benzene (abbreviation: TmPyPB). Among the above materials, heterocyclic compounds having diazine skeletons and triazine skeletons and heterocyclic compounds having pyridine skeletons have high reliability and are thus preferable. Heterocyclic compounds having diazine (pyrimidine or pyrazine) skeletons and triazine skeletons have a high electron-transport property and contribute to a reduction in drive voltage.

As the material which easily accepts holes (the material having a hole-transport property), a π-electron rich heteroaromatic compound (e.g., a carbazole derivative or an indole derivative), an aromatic amine compound, or the like can be favorably used. Specific examples include compounds having aromatic amine skeletons, such as 2-[N-(9-phenylcarbazol-3-yl)-N-phenylamino]spiro-9,9'-bifluorene (abbreviation: PCASF), 4,4',4"-tris[N-(1-naphthyl)-N-phenylamino]triphenylamine (abbreviation: 1'-TNATA), 2,7-bis[N-(4-diphenylaminophenyl)-N-phenylamino]-spiro-9,9'-bifluorene (abbreviation: DPA2SF), N,N'-bis(9-phenylcarbazol-3-yl)-N,N-diphenylbenzene-1,3-diamine (abbreviation: PCA2B), N-(9,9-dimethyl-2-diphenylamino-9H-fluoren-7-yl)diphenylamine (abbreviation: DPNF), N,N',N"-triphenyl-N,N',N"-tris(9-phenylcarbazol-3-yl)benzene-1,3,5-triamine (abbreviation: PCA3B), 2-[N-(9-phenylcarbazol-3-yl)-N-phenylamino]spiro-9,9'-bifluorene (abbreviation: PCASF), 2-[N-(4-diphenylaminophenyl)-N-phenylamino]spiro-9,9'-bifluorene (abbreviation: DPASF), N,N'-bis[4-(carbazol-9-yl)phenyl]-N,N'-diphenyl-9,9-dimethylfluorene-2,7-diamine (abbreviation: YGA2F), 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4,4'-bis[N-(4-diphenylaminophenyl)-N-phenylamino]biphenyl (abbreviation: DPAB), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), N-(9,9-dimethyl-9H-fluoren-2-yl)-N-{9,9-dimethyl-2-[N'-phenyl-N'-(9,9-dimethyl-9H-fluoren-2-yl)amino]-9H-fluoren-7-yl}phenylamine (abbreviation: DFLADFL), 3-[N-(9-phenylcarbazol-3-yl)-N-phenylamino]-9-phenylcarbazole (abbreviation: PCzPCA1), 3-[N-(4-diphenylaminophenyl)-N-phenylamino]-9-phenylcarbazole (abbreviation: PCzDPA1), 3,6-bis[N-(4-diphenylaminophenyl)-N-phenylamino]-9-phenylcarbazole (abbreviation: PCzDPA2), 4,4'-bis(N-{4-[N'-(3-methylphenyl)-N'-phenylamino]phenyl}-N-phenylamino)biphenyl (abbreviation: DNTPD), 3,6-bis[N-(4-diphenylaminophenyl)-N-(1-naphthyl)amino]-9-phenylcarbazole (abbreviation: PCzTPN2), and 3,6-bis[N-(9-phenylcarbazol-3-yl)-N-phenylamino]-9-phenylcarbazole (abbreviation: PCzPCA2), 4-phenyl-4'-(9-phenyl-9H-carbazol-3-yl)triphenylamine (abbreviation: PCBA1BP), 4,4'-diphenyl-4"-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4"-(9-phenyl-9H-carbazol-3-yl)triphenylamine (abbreviation: PCBNBB), 3-[N-(1-naphthyl)-N-(9-phenylcarbazol-3-yl)amino]-9-phenylcarbazole (abbreviation: PCzPCN1), 9,9-dimethyl-N-phenyl-N-[4-(9-phenyl-9H-carbazol-3-yl)phenyl]fluoren-2-amine (abbreviation: PCBAF), N-phenyl-N-[4-(9-phenyl-9H-carbazol-3-yl)phenyl]spiro-9,9'-bifluoren-2-amine (abbreviation: PCBASF), N-(4-biphenyl)-N-(9,9-dimethyl-9H-fluoren-2-yl)-9-phenyl-9H-carbazol-3-amine (abbreviation: PCBiF), and N-(1,1'-biphenyl-4-yl)-N-[4-(9-phenyl-9H-carbazol-3-yl)phenyl]-9,9-dimethyl-9H-fluoren-2-amine (abbreviation: PCBBiF); compounds having carbazole skeletons, such as 1,3-bis(N-carbazolyl)benzene (abbreviation: mCP), 4,4'-di(N-carbazolyl)biphenyl (abbreviation: CBP), 3,6-bis(3,5-diphenylphenyl)-9-phenylcarbazole (abbreviation: CzTP), and 9-phenyl-9H-3-(9-phenyl-9H-carbazol-3-yl)carbazole (abbreviation: PCCP); compounds having thiophene skeletons, such as 4,4',4"-(benzene-1,3,5-triyl)tri(dibenzothiophene) (abbreviation: DBT3P-II), 2,8-diphenyl-4-[4-(9-phenyl-9H-fluoren-9-yl)phenyl]dibenzothiophene (abbreviation: DBTFLP-III), and 4-[4-(9-phenyl-9H-fluoren-9-yl)phenyl]-6-phenyldibenzothiophene (abbreviation: DBTFLP-IV); and compounds having furan skeletons, such as 4,4',4''-(benzene-1,3,5-triyl)tri(dibenzofuran) (abbreviation: DBF3P-II) and 4-{3-[3-(9-phenyl-9H-fluoren-9-yl)phenyl]phenyl}dibenzofuran (abbreviation: mmDBFFLBi-II). Among the above-described materials, compounds having aromatic amine skeletons and compounds having carbazole skeletons are preferable because these compounds are highly reliable and have high hole-transport properties to contribute to a reduction in drive voltage.

Note that the combination of the materials which form an exciplex and is used as a host material is not limited to the above-described compounds, as long as they can transport carriers, the combination can form an exciplex, and light emission of the exciplex overlaps with an absorption band on the longest wavelength side in an absorption spectrum of a light-emitting material (an absorption corresponding to the transition of the light-emitting substance from the singlet ground state to the singlet excited state), and other materials may be used.

As the light-emitting material or host material of the light-emitting layer, a thermally activated delayed fluorescent (TADF) substance may be used. The thermally activated delayed fluorescent substance is a material having a small difference between the level of the triplet excitation energy and the level of the singlet excitation energy and a function of converting triplet excitation energy into singlet excitation energy by reverse intersystem crossing.

The thermally activated delayed fluorescent substance may be composed of one kind of material or a plurality of materials. For example, in the case where the thermally activated delayed fluorescent substance is composed of one kind of material, any of the following materials can be used, for example.

First, a fullerene, a derivative thereof, an acridine derivative such as proflavine, eosin, and the like can be given. Furthermore, a metal-containing porphyrin, such as a porphyrin containing magnesium (Mg), zinc (Zn), cadmium (Cd), tin (Sn), platinum (Pt), indium (In), or palladium (Pd), can be given. Examples of the metal-containing porphyrin include a protoporphyrin-tin fluoride complex (SnF$_2$(Proto IX)), a mesoporphyrin-tin fluoride complex (SnF$_2$(Meso IX)), a hematoporphyrin-tin fluoride complex (SnF$_2$(Hemato IX)), a coproporphyrin tetramethyl ester-tin fluoride complex (SnF$_2$(Copro III-4Me)), an octaethylporphyrin-tin fluoride complex (SnF$_2$(OEP)), an etioporphyrin-tin fluoride complex (SnF$_2$(Etio I)), and an octaethylporphyrin-platinum chloride complex (PtCl$_2$(OEP)), which are shown in the following structural formulae.

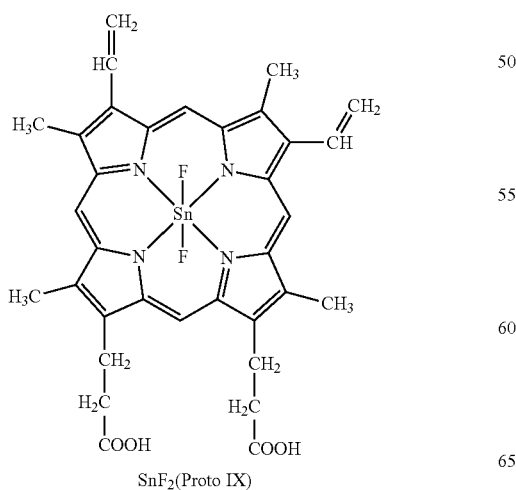

SnF$_2$(Proto IX)

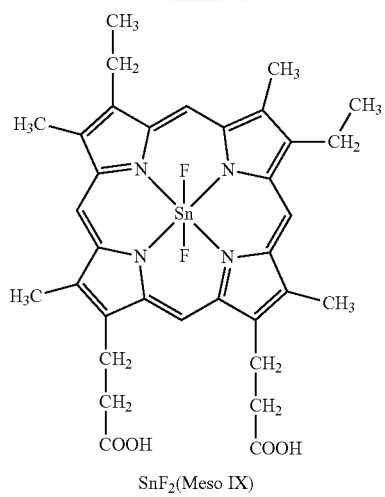

SnF$_2$(Meso IX)

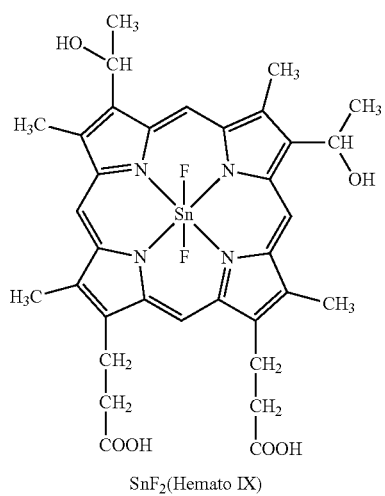

SnF$_2$(Hemato IX)

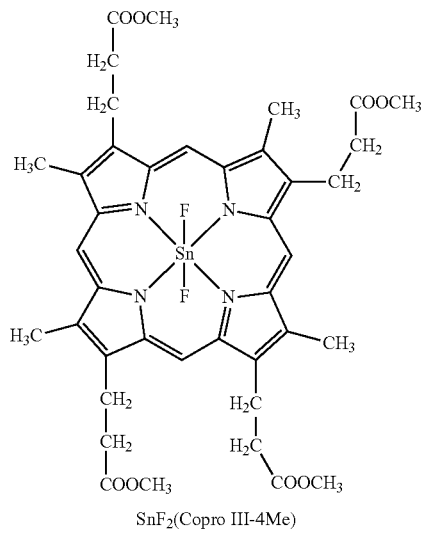

SnF$_2$(Copro III-4Me)

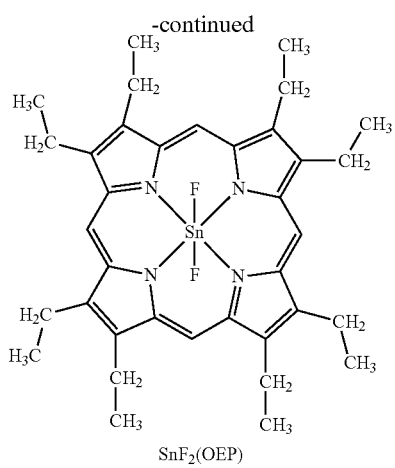

SnF₂(OEP)

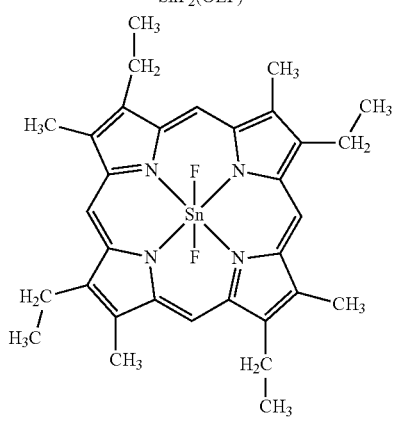

SnF₂(Etio I)

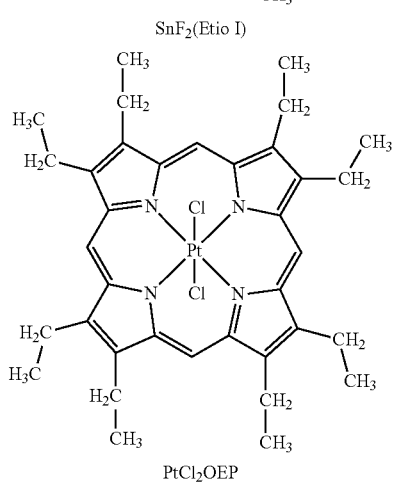

PtCl₂OEP

Alternatively, a heterocyclic compound having a π-electron rich heteroaromatic ring and a π-electron deficient heteroaromatic ring, such as 2-(biphenyl-4-yl)-4,6-bis(12-phenylindolo[2,3-a]carbazol-11-yl)-1,3,5-triazine (abbreviation: PIC-TRZ), 2-{4-[3-(N-phenyl-9H-carbazol-3-yl)-9H-carbazol-9-yl]phenyl}-4,6-diphenyl-1,3,5-triazine (abbreviation: PCCzPTzn), 2-[4-(10H-phenoxazin-10-yl)phenyl]-4,6-diphenyl-1,3,5-triazine (abbreviation: PXZ-TRZ), 3-[4-(5-phenyl-5,10-dihydrophenazine-10-yl)phenyl]-4,5-diphenyl-1,2,4-triazole (abbreviation: PPZ-3TPT), 3-(9,9-dimethyl-9H-acridin-10-yl)-9H-xanthen-9-one (abbreviation: ACRXTN), bis[4-(9,9-dimethyl-9,10-dihydroacridine)phenyl]sulfone (abbreviation: DMAC-DPS), or 10-phenyl-10H,10'H-spiro[acridin-9,9'-anthracen]-10'-one (abbreviation: ACRSA) shown in the following structural formulae, can be used as the thermally activated delayed fluorescent substance composed of one kind of material. The heterocyclic compound is preferably used because of the π-electron rich heteroaromatic ring and the π-electron deficient heteroaromatic ring, for which the electron-transport property and the hole-transport property are high. Note that a substance in which the π-electron rich heteroaromatic ring is directly bonded to the π-electron deficient heteroaromatic ring is particularly preferably used because the donor property of the π-electron rich heteroaromatic ring and the acceptor property of the π-electron deficient heteroaromatic ring are both increased and the difference between the level of the singlet excitation energy and the level of the triplet excitation energy becomes small.

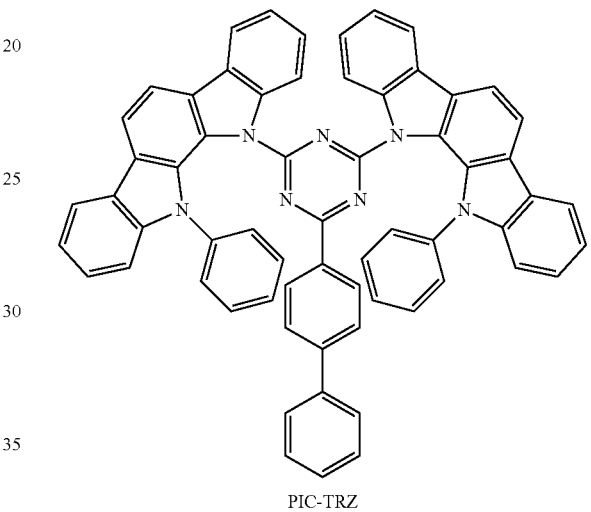

PIC-TRZ

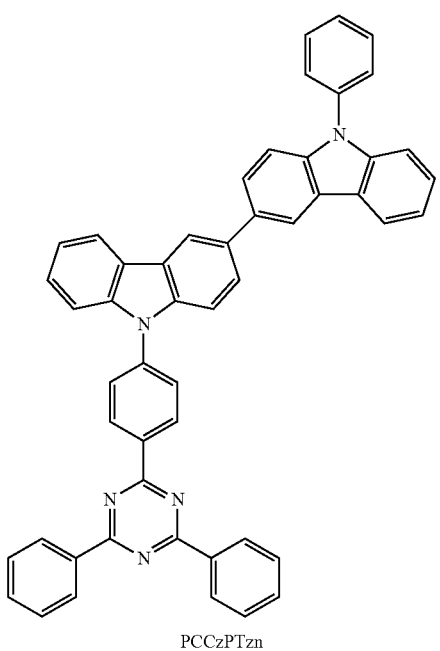

PCCzPTzn

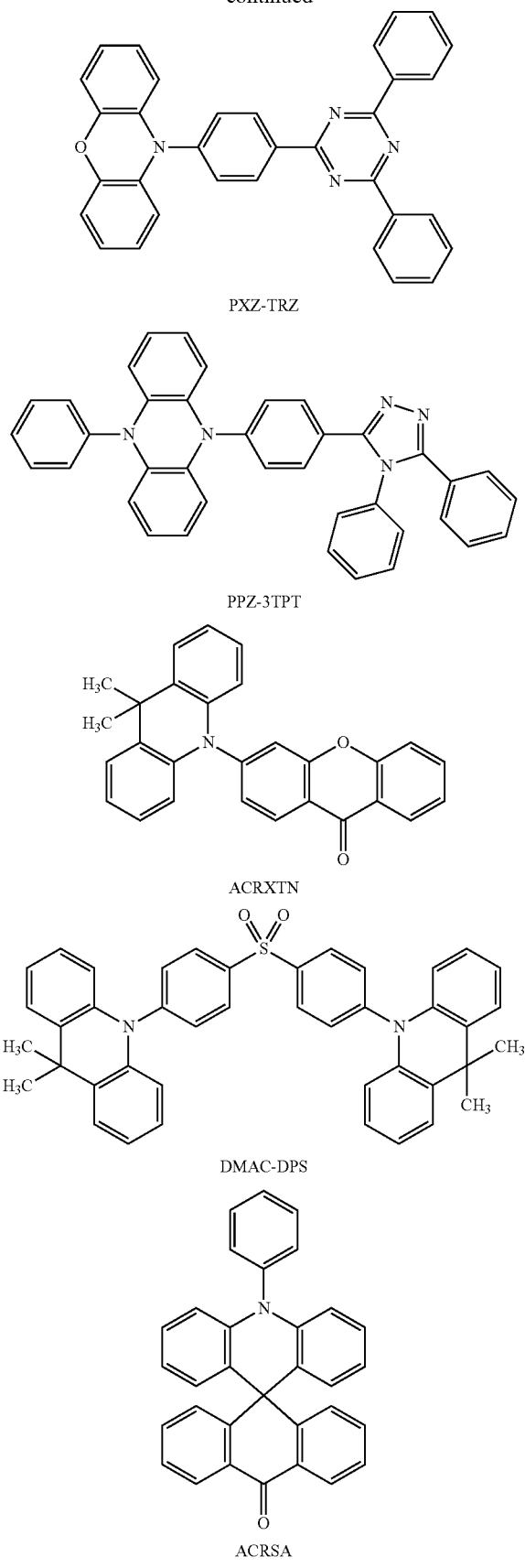

PXZ-TRZ

PPZ-3TPT

ACRXTN

DMAC-DPS

ACRSA

In the case where the thermally activated delayed fluorescent substance is used as the host material, it is preferable to use a combination of two kinds of compounds which form an exciplex. In this case, it is particularly preferable to use the above-described combination of a compound which easily accepts electrons and a compound which easily accepts holes, which forms an exciplex.

<<Hole-Injection Layer>>

The hole-injection layers 111 and 116 each inject holes from the anode to the EL layer and contain a substance having a high hole-injection property. For example, a transition metal oxide such as molybdenum oxide, vanadium oxide, ruthenium oxide, tungsten oxide, or manganese oxide can be used. Alternatively, the hole-injection layer can be formed using a phthalocyanine-based compound such as phthalocyanine (abbreviation: H₂Pc) or copper phthalocyanine (abbreviation: CuPc), an aromatic amine compound such as 4,4'-bis[N-(4-diphenylaminophenyl)-N-phenylamino]biphenyl (abbreviation: DPAB) or N,N'-bis{4-[bis(3-methylphenyl)amino]phenyl}-N,N'-diphenyl-(1,1'-biphenyl)-4,4'-diamine (abbreviation: DNTPD), a high molecule such as poly(3,4-ethylenedioxythiophene)/poly(styrenesulfonic acid) (abbreviation: PEDOT/PSS), or the like.

Alternatively, for the hole-injection layer, a composite material containing a hole-transport material and an acceptor material can be used. When the hole-injection layer contains a hole-transport material and an acceptor material, electrons are extracted from the hole-transport material by the acceptor material to generate holes and the holes are injected to the light-emitting layer through the hole-transport layer.

Examples of the hole-transport material used for the hole-injection layers 111 and 116 include aromatic amine compounds such as 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), 4,4',4"-tris(carbazol-9-yl)triphenylamine (abbreviation: TCTA), 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), and 4,4'-bis[N-(spiro-9,9'-bifluoren-2-yl)-N-phenylamino]biphenyl (abbreviation: BSPB); 3-[N-(9-phenylcarbazol-3-yl)-N-phenylamino]-9-phenylcarbazole (abbreviation: PCzPCA1); 3,6-bis[N-(9-phenylcarbazol-3-yl)-N-phenylamino]-9-phenylcarbazole (abbreviation: PCzPCA2); 3-[N-(1-naphthyl)-N-(9-phenylcarbazol-3-yl)amino]-9-phenylcarbazole (abbreviation: PCzPCN1); and the like. Alternatively, any of the following carbazole derivatives can be used: 4,4'-di(N-carbazolyl)biphenyl (abbreviation: CBP), 1,3,5-tris[4-(N-carbazolyl)phenyl]benzene (abbreviation: TCPB), and 9-[4-(10-phenyl-9-anthracenyl)phenyl]-9H-Carbazole (abbreviation: CzPA). The substances described here are mainly substances having a hole mobility of $1\times10^{-6}$ cm²/Vs or higher. However, besides the above materials, others may be used as long as the material has a higher hole transport property than an electron transport property.

Further alternatively, a high molecular compound such as poly(N-vinylcarbazole) (abbreviation: PVK), poly(4-vinyltriphenylamine) (abbreviation: PVTPA), poly[N-(4-{N'-(4-[(4-diphenylamino)phenyl]phenyl-N-phenylamino}phenyl)methacrylamide](abbreviation: PTPDMA), or poly[N,N'-bis(4-butylphenyl)-N,N'-bis(phenyl)benzidine] (abbreviation: Poly-TPD) can be used.

Other examples of the acceptor material used for the hole-injection layers 111 and 116 include compounds having an electron-withdrawing group (a halogen group or a cyano group), such as 7,7,8,8-tetracyano-2,3,5,6-tetrafluoroquinodimethane (abbreviation: F$_4$-TCNQ), chloranil, and 2,3,6,7,10,11-hexacyano-1,4,5,8,9,12-hexaazatriphenylene (abbreviation: HAT-CN). In addition, transition metal oxides can be given. Moreover, oxides of metals belonging to Groups 4 to 8 of the periodic table can be given. Specifically, it is preferable to use vanadium oxide, niobium oxide, tantalum oxide, chromium oxide, molybdenum oxide, tungsten oxide, manganese oxide, and rhenium oxide because of their high electron accepting properties. Among these, molybdenum oxide is particularly preferable because it is stable in the air and is easily treated because of its low hygroscopic property. The hole-injection layers 111 and 116 may also be formed using the above-described acceptor material alone or using the above-described acceptor material and another material in combination.

<<Hole-Transport Layer>>

The hole-transport layers 112 and 117 each contain a hole-transport material and can be formed using any of the materials given as examples of the materials of the hole-injection layers 111 and 116. In order that the hole-transport layer 112 has a function of transporting holes injected to the hole-injection layer 111 to the light-emitting layer 130, the highest occupied molecular orbital (HOMO) level of the hole-transport layer 112 is preferably equal or close to the HOMO level of the hole-injection layer 111.

Examples of the material having a hole-transport property include compounds having aromatic amine skeletons, such as 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), 4-phenyl-4'-(9-phenyl-9H-carbazol-3-yl)triphenylamine (abbreviation: PCBA1BP), 4,4'-diphenyl-4''-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4''-(9-phenyl-9H-carbazol-3-yl)triphenylamine (abbreviation: PCBNBB), 9,9-dimethyl-N-phenyl-N-[4-(9-phenyl-9H-carbazol-3-yl)phenyl]fluoren-2-amine (abbreviation: PCBAF), and N-phenyl-N-[4-(9-phenyl-9H-carbazol-3-yl)phenyl]spiro-9,9'-bifluoren-2-amine (abbreviation: PCBASF); compounds having carbazole skeletons, such as 1,3-bis(N-carbazolyl)benzene (abbreviation: mCP), 4,4'-di(N-carbazolyl)biphenyl (abbreviation: CBP), 3,6-bis(3,5-diphenylphenyl)-9-phenylcarbazole (abbreviation: CzTP), and 3,3'-bis(9-phenyl-9H-carbazole) (abbreviation: PCCP); compounds having thiophene skeletons, such as 4,4',4''-(benzene-1,3,5-triyl)tri(dibenzothiophene) (abbreviation: DBT3P-II), 2,8-diphenyl-4-[4-(9-phenyl-9H-fluoren-9-yl)phenyl]dibenzothiophene (abbreviation: DBTFLP-III), and 4-[4-(9-phenyl-9H-fluoren-9-yl)phenyl]-6-phenyldibenzothiophene (abbreviation: DBTFLP-IV); and compounds having furan skeletons, such as 4,4',4''-(benzene-1,3,5-triyl)tri(dibenzofuran) (abbreviation: DBF3P-II) and 4-{3-[3-(9-phenyl-9H-fluoren-9-yl)phenyl]phenyl}dibenzofuran (abbreviation: mmDBFFLBi-II). Among the above materials, a compound having an aromatic amine skeleton and a compound having a carbazole skeleton are preferable because these compounds are highly reliable and have high hole-transport properties to contribute to a reduction in drive voltage. Hole-transport materials can be selected from a variety of substances as well as from the hole-transport materials given above.

Furthermore, examples of the substance having a high hole-transport property include compounds having aromatic amine skeletons, such as 3-[4-(1-naphthyl)-phenyl]-9-phenyl-9H-carbazole (abbreviation: PCPN), 3-[4-(9-phenanthryl)-phenyl]-9-phenyl-9H-carbazole (abbreviation: PCPPn), 4-phenyl-4'-(9-phenyl-9H-carbazol-3-yl)triphenylamine (abbreviation: PCBA1BP), 4,4'-di(1-naphthyl)-4''-(9-phenyl-9H-carbazol-3-yl)triphenylamine (abbreviation: PCBNBB), 4-phenyldiphenyl-(9-phenyl-9H-carbazol-3-yl)amine (abbreviation: PCA1BP), 3,3'-bis(9-phenyl-9H-carbazole) (abbreviation: PCCP), N-[4-(9H-carbazol-9-yl)phenyl]-N-(4-phenyl)phenylaniline (abbreviation: YGA1BP), 1,3,5-tri(dibenzothiophen-4-yl)-benzene (abbreviation: DBT3P-II), 4,4',4''-(benzene-1,3,5-triyl)tri(dibenzofuran) (abbreviation: DBF3P-II), 4-phenyl-4'-(9-phenylfluoren-9-yl)triphenylamine (abbreviation: BPAFLP), 4-[3-(triphenylen-2-yl)phenyl]dibenzothiophene (abbreviation: mDBTPTp-II), 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), 4,4',4''-tris(carbazol-9-yl)triphenylamine (abbreviation: TCTA), 4,4',4''-tris(N,N-diphenylamino)triphenylamine (abbreviation: TDATA), 4,4',4''-tris[N-(3-methylphenyl)-N-phenylamino]triphenylamine (abbreviation: MTDATA), and 4,4'-bis[N-(spiro-9,9'-bifluoren-2-yl)-N-phenylamino]biphenyl (abbreviation: BSPB); 3-[N-(9-phenylcarbazol-3-yl)-N-phenylamino]-9-phenylcarbazole (abbreviation: PCzPCA1; 3,6-bis[N-(9-phenylcarbazol-3-yl)-N-phenylamino]-9-phenylcarbazole (abbreviation: PCzPCA2); 3-[N-(1-naphthyl)-N-(9-phenylcarbazol-3-yl)amino]-9-phenylcarbazole (abbreviation: PCzPCN1); and the like. Other examples include carbazole compounds such as 4,4'-di(N-carbazolyl)biphenyl (abbreviation: CBP) and 1,3,5-tris[4-(N-carbazolyl)phenyl]benzene (abbreviation: TCPB); amine compounds; dibenzothiophene compounds; dibenzofuran compounds; fluorene compounds; triphenylene compounds; phenanthrene compounds; and the like.

Note that any of these compounds that can be used for the hole-transport layer can also be used for the hole-injection layer.

<<Electron-Transport Layer>>

The electron-transport layers 113 and 118 each contain a substance having an electron-transport property. Examples of the substance having a high-electron transport property used for the electron-transport layers 113 and 118 include metal complexes having a quinoline ligand, a benzoquinoline ligand, an oxazole ligand, and a thiazole ligand; an oxadiazole derivative; a triazole derivative; a phenanthroline derivative; a pyridine derivative; and a bipyridine derivative. Specific examples include metal complexes such as Alq, Almq$_3$, BeBq$_2$, BAlq, ZnPBO, and ZnBTZ. Other examples include heteroaromatic compounds such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: Bphen), bathocuproine (abbreviation: BCP), 4,4'-bis(5-methylbenzoxazol-2-yl)stilbene (abbreviation: BzOs). Further alternatively, a high molecular compound such as poly(2,5-pyridinediyl) (abbreviation: PPy), poly[(9,9-dihexylfluorene-2,7-diyl)-co-(pyridine-3,5-diyl)] (abbreviation: PF-Py), or poly[(9,9-dioctylfluorene-2,7-diyl)-co-(2,2'-bipyridine-6,6'-diyl)] (abbreviation: PF-BPy) can be used. The substances described here are mainly substances having an electron mobility of $1 \times 10^{-6}$ cm$^2$/Vs or higher.

Note that other substances may also be used for the electron-transport layers 113 and 118 as long as their electron-transport properties are higher than their hole-transport properties.

The electron-transport layers 113 and 118 are each not limited to a single layer, and may be a stack of two or more layers each containing any of the above-described substances.

<<Electron-Injection Layer>>

The electron-injection layers 114 and 119 each contain a substance having a high electron-injection property. For the electron-injection layer 114, an alkali metal, an alkaline earth metal, or a compound thereof, such as lithium fluoride, cesium fluoride, calcium fluoride, or lithium oxide, can be used. Alternatively, a rare earth metal compound like erbium fluoride can be used. Electride may also be used for the electron-injection layers 114 and 119. Examples of the electride include a substance in which electrons are added at a high concentration to calcium oxide-aluminum oxide. The electron-injection layers 114 and 119 can be formed using the substance that can be used for the electron-transport layers 113 and 118.

Alternatively, the electron-injection layers 114 and 119 may be formed using a composite material in which an organic compound and an electron donor (donor) are mixed. The composite material is superior in an electron-injection property and an electron-transport property, since electrons are generated in the organic compound by the electron donor. The organic compound here is preferably a material excellent in transporting the generated electrons; specifically, for example, the substances for forming the electron-transport layers 113 and 118 (e.g., a metal complex or a heteroaromatic compound) can be used. As the electron donor, a substance showing an electron-donating property with respect to the organic compound may be used. Specifically, an alkali metal, an alkaline earth metal, and a rare earth metal are preferable, and lithium, cesium, magnesium, calcium, erbium, ytterbium, and the like can be given. Further, an alkali metal oxide or an alkaline earth metal oxide is preferable, and for example, lithium oxide, calcium oxide, barium oxide, and the like can be given. Alternatively, Lewis base such as magnesium oxide can also be used. An organic compound such as tetrathiafulvalene (abbreviation: TTF) can also be used.

<<Charge-Generation Layer>>

The charge-generation layer 115 has a function of injecting electrons to one of the light-emitting layers (the light-emitting layer 134 or 136) and injecting holes to the other light-emitting layer (the light-emitting layer 134 or 136), when a voltage is applied between the pair of electrodes (the electrodes 101 and 102).

For example, in the tandem light-emitting element 152 illustrated in FIG. 3, when a voltage is applied such that the potential of the electrode 101 is higher than that of the electrode 102, the charge-generation layer 115 injects electrons to the light-emitting layer 134 and injects holes to the light-emitting layer 136.

Note that in terms of light extraction efficiency, the charge-generation layer 115 preferably transmits visible light (specifically, the charge-generation layer 115 has a visible light transmittance higher than or equal to 40%). The charge-generation layer 115 functions even if it has lower conductivity than the pair of electrodes (the electrodes 101 and 102).

The charge-generation layer 115 may have either a structure in which an electron acceptor (acceptor) is added to a hole-transport material or a structure in which an electron donor (donor) is added to an electron-transport material. Alternatively, both of these structures may be stacked.

Note that forming the charge-generation layer 115 by using any of the above materials can suppress an increase in drive voltage caused by the stack of the light-emitting layers.

The above-described light-emitting layer, hole-injection layer, hole-transport layer, electron-transport layer, electron-injection layer, and charge-generation layer can each be formed by any of the following methods: an evaporation method (including a vacuum evaporation method), an ink-jet method, a coating method, gravure printing, and the like. Besides the above-mentioned materials, an inorganic compound such as a quantum dot or a high molecular compound (e.g., an oligomer, a dendrimer, or a polymer) may be used for the above-described light-emitting layer, hole-injection layer, hole-transport layer, electron-transport layer, electron-injection layer, and charge-generation layer.

The quantum dot may be a colloidal quantum dot, an alloyed quantum dot, a core-shell quantum dot, or a core quantum dot, for example. For the quantum dot, elements belonging to Groups 2 and 16, elements belonging to Groups 13 and 15, elements belonging to Groups 13 and 17, elements belonging to Groups 11 and 17, or elements belonging to Groups 14 and 15 may be used. Alternatively, for the quantum dot, an element such as cadmium (Cd), selenium (Se), zinc (Zn), sulfur (S), phosphorus (P), indium (In), tellurium (Te), lead (Pb), gallium (Ga), arsenic (As), or aluminum (Al) may be used.

<<Optical Element>>

The optical elements 224R, 224G, and 224B each selectively transmit light of a particular color out of incident light. For example, a coloring layer (also referred to as color filter), a band pass filter, a multilayer filter, or the like can be used, for example. Alternatively, color conversion elements can be used as the optical elements. A color conversion element is an optical element that converts incident light into light having a longer wavelength than the incident light. As the color conversion elements, quantum-dot elements are favorably used. The usage of the quantum-dot can increase color reproducibility of the display device.

A plurality of optical elements may also be stacked over each of the optical elements 224R, 224G, and 224B. As another optical element, a circularly polarizing plate, an anti-reflective film, or the like can be provided, for example. A circularly polarizing plate provided on the side where light emitted from the light-emitting element of the display device is extracted can prevent a phenomenon in which light entering from the outside of the display device is reflected inside the display device and returned to the outside. An anti-reflective film can weaken external light reflected by a surface of the display device. Accordingly, light emitted from the display device can be observed clearly.

<<Light-Blocking Layer>>

The light-blocking layer 223 has a function of reducing the reflection of external light. The light-blocking layer 223 has a function of preventing mixture of light emitted from an adjacent light-emitting element. As the light-blocking layer 223, a metal, a resin containing black pigment, carbon black, a metal oxide, a composite oxide containing a solid solution of a plurality of metal oxides, or the like can be used.

<<Partition Wall>>

The partition wall 140 has an insulating property and is formed using an inorganic or organic material. Examples of the inorganic material include silicon oxide, silicon oxynitride, silicon nitride oxide, silicon nitride, aluminum oxide, and aluminum nitride. Examples of the organic material include photosensitive resin materials such as an acrylic resin and a polyimide resin.

<6. Fabrication Method of Light-Emitting Element>

Next, a method for fabricating a light-emitting element of one embodiment of the present invention is described below with reference to FIGS. 6A to 6C and FIGS. 7A to 7C. Here, a method for fabricating the light-emitting element 254 illustrated in FIG. 5A is described.

FIGS. 6A to 6C and FIGS. 7A to 7C are cross-sectional views illustrating a method for fabricating the light-emitting element of one embodiment of the present invention.

The method for manufacturing the light-emitting element 254 described below includes first to seventh steps.

<<First Step>>

Figure 6A:
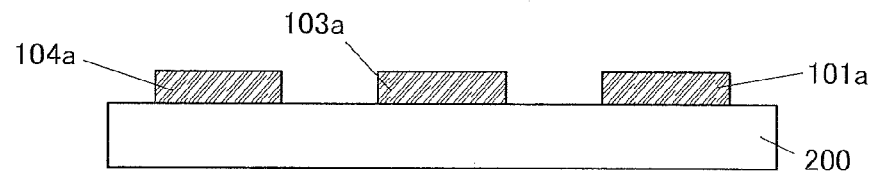
FIGS. 6A to 6C are schematic cross-sectional views illustrating a method for fabricating a light-emitting element of one embodiment of the present invention.

In the first step, the electrodes (specifically the conductive layer 101a of the electrode 101, the conductive layer 103a of the electrode 103, and the conductive layer 104a of the electrode 104) of the light-emitting elements are formed over the substrate 200 (see FIG. 6A).

In this embodiment, a conductive layer having a function of reflecting light is formed over the substrate 200 and processed into a desired shape; whereby the conductive layers 101a, 103a, and 104a are formed. As the conductive layer having a function of reflecting light, an alloy film of silver, palladium, and copper (also referred to as an Ag—Pd—Cu film and APC) is used. The conductive layers 101a, 103a, and 104a are preferably formed through a step of processing the same conductive layer, because the manufacturing cost can be reduced.

Note that a transistor may be formed over the substrate 200 before the first step. The transistor may be electrically connected to the conductive layers 101a, 103a, and 104a.

<<Second Step>>

Figure 6B:
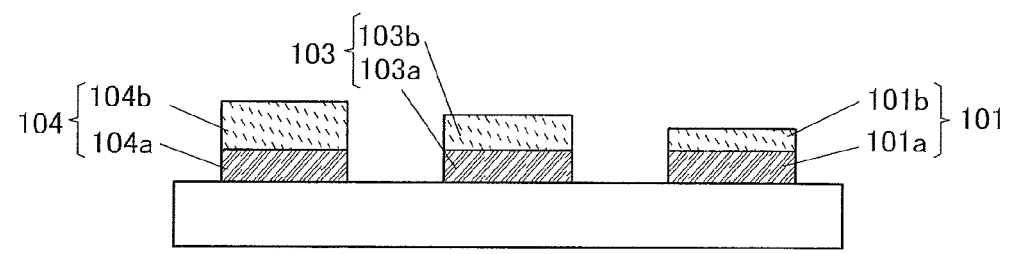

In the second step, the transparent conductive layer 101b having a function of transmitting light is formed over the conductive layer 101a of the electrode 101, the transparent conductive layer 103b having a function of transmitting light is formed over the conductive layer 103a of the electrode 103, and the transparent conductive layer 104b having a function of transmitting light is formed over the conductive layer 104a of the electrode 104 (see FIG. 6B).

In this embodiment, the conductive layers 101b, 103b, and 104b each having a function of transmitting light are formed over the conductive layers 101a, 103a, and 104a each having a function of reflecting light, respectively, whereby the electrode 101, the electrode 103, and the electrode 104 are formed. As the conductive layers 101b, 103b, and 104b, ITSO films are used.

The conductive layers 101b, 103b, and 104b having a function of transmitting light may be formed through a plurality of steps. When the conductive layers 101b, 103b, and 104b having a function of transmitting light are formed through a plurality of steps, they can be formed to have thicknesses which enable microcavity structures appropriate in the respective regions.

<<Third Step>>

Figure 6C:
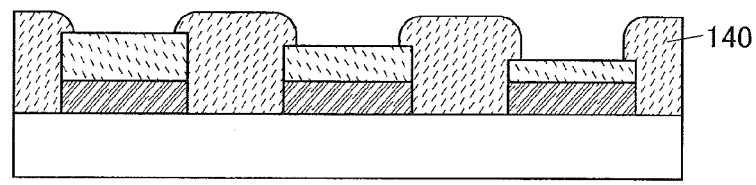

In the third step, the partition wall 140 that covers end portions of the electrodes of the light-emitting element is formed (see FIG. 6C).

The partition wall 140 includes an opening overlapping with the electrode. The conductive film exposed by the opening functions as the anode of the light-emitting element. As the partition wall 140, a polyimide-based resin is used in this embodiment.

In the first to third steps, since there is no possibility of damaging the EL layer (a layer containing an organic compound), a variety of film formation methods and micromachining technologies can be employed. In this embodiment, a reflective conductive layer is formed by a sputtering method, a pattern is formed over the conductive layer by a lithography method, and then the conductive layer is processed into an island shape by a dry etching method or a wet etching method to form the conductive layer 101a of the electrode 101, the conductive layer 103a of the electrode 103, and the conductive layer 104a of the electrode 104. Then, a transparent conductive film is formed by a sputtering method, a pattern is formed over the transparent conductive film by a lithography method, and then the transparent conductive film is processed into island shapes by a wet etching method to form the electrodes 101, 103, and 104.

<<Fourth Step>>

Figure 7A:
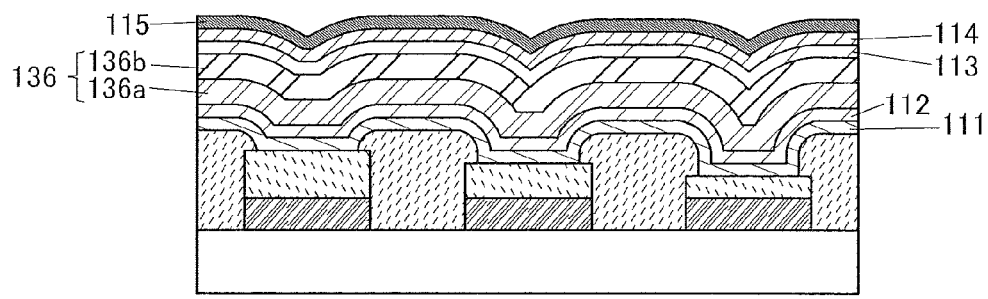
FIGS. 7A to 7C are schematic cross-sectional views illustrating a method for fabricating a light-emitting element of one embodiment of the present invention.

In the fourth step, the hole-injection layer 111, the hole-transport layer 112, the light-emitting layer 136, the electron-transport layer 113, the electron-injection layer 114, and the charge-generation layer 115 are formed (see FIG. 7A).

The hole-injection layer 111 can be formed by co-evaporating a hole-transport material and a material containing an acceptor material. The hole-transport layer 112 can be formed by evaporating a hole-transport material.

The light-emitting layer 136 can be formed by evaporating the second guest material that emits light of at least one of green, yellow green, yellow, orange, and red. As the second guest material, a fluorescent or phosphorescent material can be used. The phosphorescent material may be evaporated alone or the phosphorescent material mixed with another material may be evaporated. The phosphorescent material may be used as a guest material, and the guest material may be dispersed into a host material having higher excitation energy than the guest material. The light-emitting layer 136 preferably has a two-layer structure of the light-emitting layer 136a and the light-emitting layer 136b. In that case, the light-emitting layers 136a and 136b each preferably contain a light-emitting material that emits light of a different color.

The electron-transport layer 113 can be formed by evaporating a material having an electron-transport property. The electron-injection layer 114 can be formed by evaporating a material having an electron-injection property.

The charge-generation layer 115 can be formed by evaporating a material obtained by adding an electron acceptor (acceptor) to a hole-transport material or a material obtained by adding an electron donor (donor) to an electron-transport material.

<<Fifth Step>>

Figure 7B:
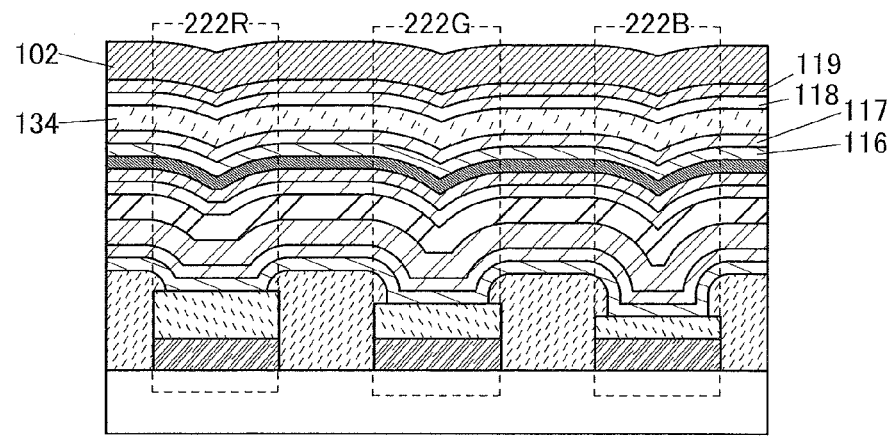

In the fifth step, the hole-injection layer 116, the hole-transport layer 117, the light-emitting layer 134, the electron-transport layer 118, the electron-injection layer 119, and the electrode 102 are formed (see FIG. 7B).

The hole-injection layer 116 can be formed by using a material and a method which are similar to those of the hole-injection layer 111. The hole-transport layer 117 can be formed by using a material and a method which are similar to those of the hole-transport layer 112.

The light-emitting layer 134 can be formed by evaporating the first guest material that emits blue light. As the first guest material, a phosphorescent organic compound can be used. The phosphorescent organic compound may be evaporated alone or the phosphorescent material mixed with another material may be evaporated. The phosphorescent organic compound may be used as a guest material, and the guest material may be dispersed into a host material having higher excitation energy than the guest material.

As the first guest material in the light-emitting layer 134, it is preferable to use a substance the emission spectrum of which in a dichloromethane solution has a maximum value (a peak) in a wavelength region ranging from 440 nm to 470 nm and has a full width at half maximum of greater than or equal to 20 nm and less than or equal to 80 nm. Alternatively, the light intensity of the substance in the dichloromethane solution at a wavelength of 530 nm is preferably greater than or equal to 0% and less than or equal to 50% of the maximum light intensity. Alternatively, the chromaticity y in the CIE 1931 chromaticity coordinates, which is calculated from the emission spectrum, is preferably greater than or equal to 0.01 and less than or equal to 0.3.

The electron-transport layer 118 can be formed by evaporating a material having an electron-transport property. The electron-injection layer 119 can be formed by evaporating a material having an electron-injection property.

The electrode 102 can be formed by stacking a reflective conductive film and a light-transmitting conductive film. The electrode 102 may have a single-layer structure or a stacked-layer structure.

Through the above-described steps, the light-emitting element including the region 222B, the region 222G, and the region 222R over the electrode 101, the electrode 103, and the electrode 104, respectively, are formed over the substrate 200.

<<Sixth Step>>

Figure 7C:
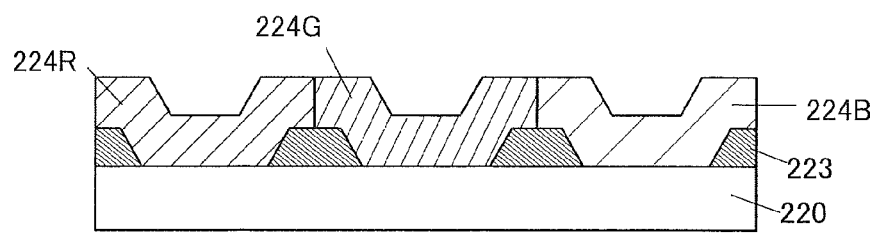

In the sixth step, the light-blocking layer 223, the optical element 224B, the optical element 224G, and the optical element 224R are formed over the substrate 220 (see FIG. 7C).

As the light-blocking layer 223, a resin film containing black pigment is formed in a desired region. Then, the optical element 224B, the optical element 224G, and the optical element 224R are formed over the substrate 220 and the light-blocking layer 223. As the optical element 224B, a resin film containing blue pigment is formed in a desired region. As the optical element 224G, a resin film containing green pigment is formed in a desired region. As the optical element 224R, a resin film containing red pigment is formed in a desired region.

<<Seventh Step>>

In the seventh step, the light-emitting element formed over the substrate 200 is attached to the light-blocking layer 223, the optical element 224B, the optical element 224G, and the optical element 224R formed over the substrate 220, and sealed with a sealant (not illustrated).

Through the above-described steps, the light-emitting element 254 illustrated in FIG. 5A can be formed.

In Embodiment 1, one embodiment of the present invention is described. Other embodiments of the present invention are described in Embodiments 2 to 8. Note that one embodiment of the present invention is not limited to the embodiments. For example, one embodiment of the present invention shows, but is not limited to, an example in which a guest material has a function of converting the triplet excitation energy into light emission. Depending on circumstances or conditions, for example, the guest material in one embodiment of the present invention does not necessarily have a function of converting the triplet excitation energy into light emission. Furthermore, one embodiment of the present invention shows, but is not limited to, an example in which the emission spectrum of a guest material in a dichloromethane solution has a peak in a wavelength region ranging from 440 nm to 470 nm and a full width at half maximum of greater than or equal to 20 nm and less than or equal to 80 nm. Depending on circumstances or conditions, for example, the emission spectrum of the guest material in the dichloromethane solution does not necessarily have a peak in a wavelength region ranging from 440 nm to 470 nm in one embodiment of the present invention. Depending on circumstances or conditions, the emission spectrum of the guest material in the dichloromethane solution does not necessarily have a full width at half maximum of greater than or equal to 20 nm and less than or equal to 80 nm in one embodiment of the present invention. Alternatively, the light intensity of the guest material in the dichloromethane solution at a wavelength of 530 nm is not necessarily greater than or equal to 0% and less than or equal to 50% of the maximum light intensity. Alternatively, the chromaticity y in the CIE 1931 chromaticity coordinates, which is calculated from the emission spectrum of the guest material in the dichloromethane solution, may be greater than 0.3. Alternatively, these emission spectra may be measured using a solution other than the dichloromethane solution. For example, one embodiment of the present invention shows, but is not limited to, an example of a light-emitting element that emits light with a chromaticity y (the CIE 1931 chromaticity coordinates) greater than or equal 0.01 and less than or equal to 0.06 at a current efficiency greater than or equal to 3 cd/A, an example of a light-emitting element that emits light with a chromaticity y greater than 0.06 and less than or equal to 0.08 at a current efficiency greater than or equal to 8 cd/A, or an example of a light-emitting element that emits light with a chromaticity y greater than 0.08 and less than or equal to 0.1 at a current efficiency greater than or equal to 10 cd/A. Depending on circumstances or conditions, for example, the light-emitting element of one embodiment of the present invention does not necessarily emit light with a chromaticity y greater than or equal 0.01 and less than or equal to 0.06 at a current efficiency greater than or equal to 3 cd/A, light with a chromaticity y greater than 0.06 and less than or equal to 0.08 at a current efficiency greater than or equal to 8 cd/A, or light with a chromaticity y greater than 0.08 and less than or equal to 0.1 at a current efficiency greater than or equal to 10 cd/A. One embodiment of the present invention shows, but is not limited to, an example of a light-emitting element that includes an electrode having a function of reflecting light and an electrode having a function of reflecting light and a function of transmitting light. Depending on circumstances or conditions, for example, the light-emitting element of one embodiment of the present invention does not necessarily include the electrode having a function of reflecting light. In addition, depending on circumstances or conditions, the light-emitting element of one embodiment of the present invention does not necessarily include the electrode having a function of reflecting light and a function of transmitting light.

This embodiment can be combined as appropriate with any of the other embodiments.

Embodiment 2

In this embodiment, a light emission mechanism in a light-emitting element of one embodiment of the present invention or a light-emitting element that can be used in a display device of one embodiment of the present invention is described with reference to FIGS. 8A and 8B.

<Structure Example of Light-Emitting Element>

Figure 8A:
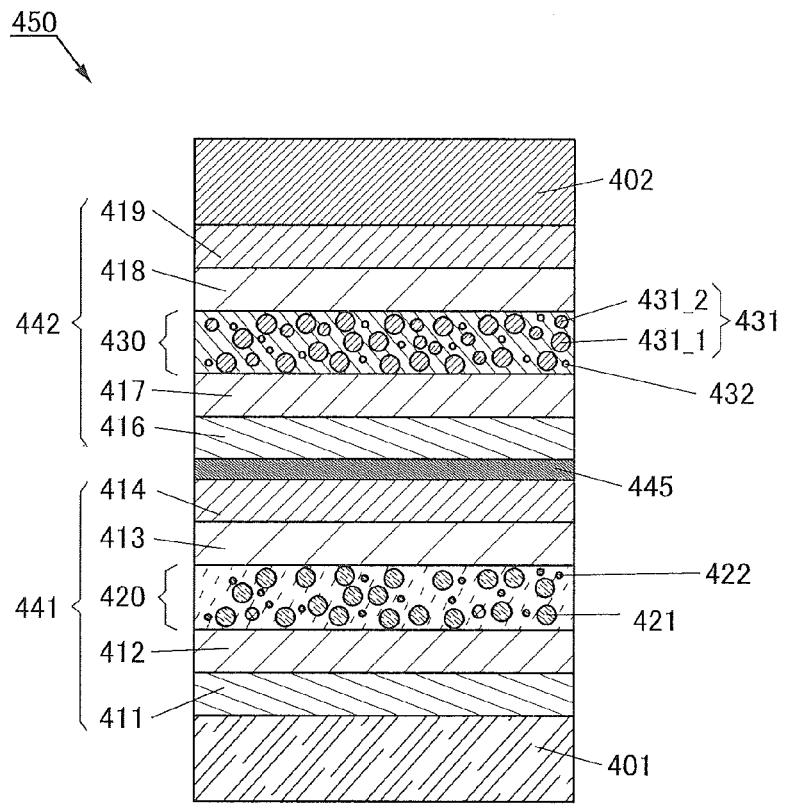
FIG. 8A is a schematic cross-sectionals view of a light-emitting element of one embodiment of the present invention and FIG. 8B is a schematic diagram illustrating the correlation of energy levels.

FIG. 8A is a schematic cross-sectional view of a light-emitting element 450.

The light-emitting element 450 illustrated in FIG. 8A includes a plurality of light-emitting units (in FIG. 8A, a light-emitting unit 441 and a light-emitting unit 442)

between a pair of electrodes (an electrode 401 and an electrode 402). One light-emitting unit has the same structure as the EL layer 100 illustrated in FIG. 1A. That is, the light-emitting element 150 in FIG. 1A includes one light-emitting unit, while the light-emitting element 450 includes the plurality of light-emitting units. Note that the electrode 401 functions as an anode and the electrode 402 functions as a cathode in the following description of the light-emitting element 450; however, the functions may be interchanged in the light-emitting element 450.

In the light-emitting element 450 illustrated in FIG. 8A, the light-emitting unit 441 and the light-emitting unit 442 are stacked, and a charge-generation layer 445 is provided between the light-emitting unit 441 and the light-emitting unit 442. Note that the light-emitting unit 441 and the light-emitting unit 442 may have the same structure or different structures. For example, it is preferable that the EL layer 100 illustrated in FIG. 1A be used in the light-emitting unit 441 and that a light-emitting layer containing a phosphorescent material as a light-emitting material be used in the light-emitting unit 442.

That is, the light-emitting element 450 includes a light-emitting layer 420 and a light-emitting layer 430. The light-emitting unit 441 includes a hole-injection layer 411, a hole-transport layer 412, an electron-transport layer 413, and an electron-injection layer 414 in addition to the light-emitting layer 420. The light-emitting unit 442 includes a hole-injection layer 416, a hole-transport layer 417, an electron-transport layer 418, and an electron-injection layer 419 in addition to the light-emitting layer 430.

The charge-generation layer 445 contains a composite material of an organic compound and an acceptor material. For the composite material, the composite material that can be used for the hole-injection layer 111 described in Embodiment 1 may be used. As the organic compound, a variety of compounds such as an aromatic amine compound, a carbazole compound, an aromatic hydrocarbon, and a high molecular compound (such as an oligomer, a dendrimer, or a polymer) can be used. An organic compound having a hole mobility of $1 \times 10^{-6}$ cm$^2$/Vs or higher is preferably used. Note that any other substance may be used as long as the substance has a property of transporting more holes than electrons. Since the composite material of an organic compound and an acceptor material has excellent carrier-injection and carrier-transport properties, low-voltage driving or low-current driving can be realized. Note that when a surface of a light-emitting unit on the anode side is in contact with the charge-generation layer, the charge-generation layer can also serve as a hole-injection layer or a hole-transport layer of the light-emitting unit; thus, a hole-injection layer or a hole-transport layer does not need to be included in the light-emitting unit.

The charge-generation layer 445 may have a stacked-layer structure of a layer containing the composite material of an organic compound and an acceptor material and a layer containing another material. For example, the charge-generation layer 445 may be formed using a combination of a layer containing the composite material of an organic compound and an acceptor material with a layer containing one compound selected from among electron-donating substances and a compound having a high electron-transport property. Furthermore, the charge-generation layer 445 may be formed using a combination of a layer containing the composite material of an organic compound and an acceptor material with a layer including a transparent conductive film.

The charge-generation layer 445 provided between the light-emitting unit 441 and the light-emitting unit 442 may have any structure as long as electrons can be injected to the light-emitting unit on one side and holes can be injected into the light-emitting unit on the other side when a voltage is applied between the electrode 401 and the electrode 402. For example, in FIG. 8A, the charge-generation layer 445 injects electrons into the light-emitting unit 441 and holes into the light-emitting unit 442 when a voltage is applied such that the potential of the electrode 401 is higher than that of the electrode 402.

The light-emitting element having two light-emitting units is described with reference to FIG. 8A; however, a similar structure can be applied to a light-emitting element in which three or more light-emitting units are stacked. With a plurality of light-emitting units partitioned by the charge-generation layer between a pair of electrodes as in the light-emitting element 450, it is possible to provide a light-emitting element which can emit light with high luminance with the current density kept low and has a long lifetime. A light-emitting element with low power consumption can be provided.

When the structure of the EL layer 100 illustrated in FIG. 1A is applied to at least one of the plurality of units, a light-emitting element with high emission efficiency can be provided.

The light-emitting layer 420 contains a host material 421 and a guest material 422. The light-emitting layer 430 contains a host material 431 and a guest material 432. The host material 431 contains an organic compound 431_1 and an organic compound 431_2.

In this embodiment, the light-emitting layer 420 has a structure similar to that of the light-emitting layer 130 in FIGS. 1A and 1B. That is, the host material 421 and the guest material 422 in the light-emitting layer 420 correspond to the host material 131 and the guest material 132 in the light-emitting layer 130, respectively. In the following description, the guest material 432 contained in the light-emitting layer 430 is a phosphorescent material. Note that the electrode 401, the electrode 402, the hole-injection layers 411 and 416, the hole-transport layers 412 and 417, the electron-transport layers 413 and 418, and the electron-injection layers 414 and 419 correspond to the electrode 101, the electrode 102, the hole-injection layer 111, the hole-transport layer 112, the electron-transport layer 118, and the electron-injection layer 119 in Embodiment 1, respectively. Therefore, detailed description thereof is omitted in this embodiment.

<Emission Mechanism of Light-Emitting Layer 420>

An emission mechanism of the light-emitting layer 420 is similar to that of the light-emitting layer 130 in FIGS. 1A and 1B. Note that an emission mechanism of the light-emitting layer 420 may be similar to that of the light-emitting layer 430.

<Emission Mechanism of Light-Emitting Layer 430>

Next, an emission mechanism of the light-emitting layer 430 is described below.

The organic compound 431_1 and the organic compound 431_2 which are contained in the light-emitting layer 430 form an exciplex. The organic compound 431_1 serves as a host material and the organic compound 431_2 serves as an assist material in the description here.

Although it is acceptable as long as the combination of the organic compound 431_1 and the organic compound 431_2 in the light-emitting layer 430 can form an exciplex, it is preferred that one organic compound be a material having a hole-transport property and the other organic compound be a material having an electron-transport property.

Figure 8B:
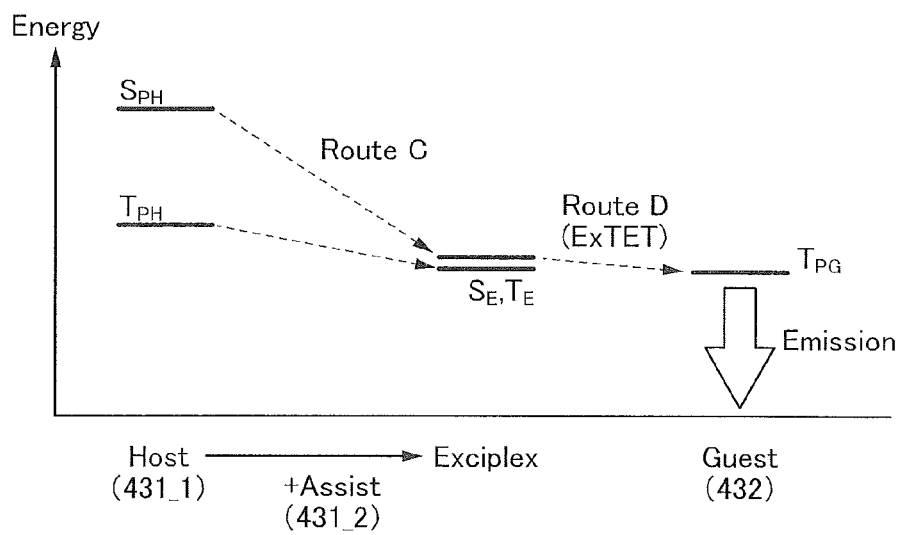

FIG. 8B illustrates the correlation of energy levels of the organic compound 431_1, the organic compound 431_2, and the guest material 432 in the light-emitting layer 430. The following explains what terms and signs in FIG. 8B represent:

Host: the organic compound 431_1 (a host material);
Assist: the organic compound 431_2 (an assist material);
Guest: the guest material 432 (a phosphorescent material);
$S_{PH}$: the level of the lowest singlet excited state of the organic compound 431_1 (a host material);
$T_{PH}$: the level of the lowest triplet excited state of the organic compound 431_1 (a host material);
$T_{PG}$: the level of the lowest triplet excited state of the guest material 432 (a phosphorescent material);
$S_E$: the level of the lowest singlet excited state of the exciplex; and
$T_E$: the level of the lowest triplet excited state of the exciplex.

The level ($S_E$) of the lowest singlet excited state of the exciplex, which is formed by the organic compound 431_1 and the organic compound 431_2, and the level ($T_E$) of the lowest triplet excited state of the exciplex are close to each other (see Route C in FIG. 8B).

Both energies of $S_E$ and $T_E$ of the exciplex are then transferred to the level ($T_{PG}$) of the lowest triplet excited state of the guest material 432 (the phosphorescent material); thus, light emission is obtained (see Route D in FIG. 8B).

The above-described processes through Route C and Route D may be referred to as exciplex-triplet energy transfer (ExTET) in this specification and the like.

One of the organic compounds 431_1 and 431_2 receives a hole and the other receives an electron, whereby an exciplex is formed. Alternatively, when one compound is brought into an excited state, the one interacts with the other compound to form the exciplex. Therefore, most excitons in the light-emitting layer 430 exist as exciplexes. The band gap of the exciplex is narrower than that of each of the organic compounds 431_1 and 431_2; therefore, the driving voltage of the light-emitting element can be lowered when the exciplex is formed.

When the light-emitting layer 430 has the above structure, light emission from the guest material 432 (the phosphorescent material) of the light-emitting layer 430 can be efficiently obtained.

Note that it does not matter whether light emitted from the light-emitting layer 420 has an emission peak on the shorter or longer wavelength side than light emitted from the light-emitting layer 430.

Furthermore, the light-emitting layer 420 and the light-emitting layer 430 may be made to emit light with different emission wavelengths, so that the light-emitting element can be a multicolor light-emitting element. In that case, the emission spectrum is formed by combining light having different emission peaks, and thus has at least two peaks.

The above structure is also suitable for obtaining white light emission. When the light-emitting layer 420 and the light-emitting layer 430 emit light of complementary colors, white light emission can be obtained.

In addition, white light emission with a high color rendering property that is formed of three primary colors or four or more colors can be obtained by using a plurality of light-emitting materials emitting light with different wavelengths for one of the light-emitting layers 420 and 430 or both. In that case, one of the light-emitting layers 420 and 430 or both may be divided into layers and each of the divided layers may contain a different light-emitting material from the others.

Next, materials that can be used for the light-emitting layers 420 and 430 will be described.

<Material that can be Used for Light-Emitting Layer 420>

A material that can be used for the light-emitting layer described in Embodiment 1 may be used as a material that can be used for the light-emitting layer 420.

<Material that can be Used for Light-Emitting Layer 430>

In the light-emitting layer 430, the organic compound 431_1 (the host material) is present in the highest proportion in weight ratio, and the guest material 432 (the phosphorescent material) is dispersed in the organic compound 431_1 (the host material).

Examples of the organic compound 431_1 (the host material) include a zinc- or aluminum-based metal complex, an oxadiazole derivative, a triazole derivative, a benzimidazole derivative, a quinoxaline derivative, a dibenzoquinoxaline derivative, a dibenzothiophene derivative, a dibenzofuran derivative, a pyrimidine derivative, a triazine derivative, a pyridine derivative, a bipyridine derivative, a phenanthroline derivative, and the like. Other examples are an aromatic amine, a carbazole derivative, and the like.

As the guest material 432 (the phosphorescent material), an iridium-, rhodium-, or platinum-based organometallic complex or a metal complex can be used; in particular, an organoiridium complex such as an iridium-based ortho-metalated complex is preferable. As an ortho-metalated ligand, a 4H-triazole ligand, a 1H-triazole ligand, an imidazole ligand, a pyridine ligand, a pyrimidine ligand, a pyrazine ligand, an isoquinoline ligand, and the like can be given. As the metal complex, a platinum complex having a porphyrin ligand and the like can be given.

As the organic compound 431_2 (the assist material), a substance which can form an exciplex together with the organic compound 431_1 is used. In that case, it is preferable that the organic compound 431_1, the organic compound 431_2, and the guest material 432 (the phosphorescent material) be selected such that the emission peak of the exciplex overlaps with an adsorption band, specifically an adsorption band on the longest wavelength side, of a triplet metal to ligand charge transfer (MLCT) transition of the guest material 432 (the phosphorescent material). This makes it possible to provide a light-emitting element with drastically improved emission efficiency. Note that in the case where a thermally activated delayed fluorescence material is used instead of the phosphorescent material, it is preferable that the adsorption band on the longest wavelength side be a singlet absorption band.

As to a combination of host materials for efficiently forming an exciplex, it is preferable that the highest occupied molecular orbital (also referred to as HOMO) level of one of the organic compound 431_1 and the organic compound 431_2 be higher than the HOMO level of the other of the organic compounds, and the lowest unoccupied molecular orbital (also referred to as LUMO) level of the one of the organic compounds be higher than the LUMO level of the other of the organic compounds. For example, when one of the organic compounds has a hole-transport property and the other of the organic compounds has an electron-transport property, it is preferable that the HOMO level of the one of the organic compounds be higher than the HOMO level of the other of the organic compounds and the LUMO level of the one of the organic compounds be higher than the LUMO level of the other of the organic compounds. Specifically, a difference in HOMO level between the organic compounds is preferably greater than or equal to 0.05 eV, more preferably greater than or equal to 0.1 eV, and still more preferably greater than or equal to 0.2 eV. A difference in LUMO level between the organic compounds is preferably greater than or equal to 0.05 eV, more preferably greater than or equal to 0.1 eV, and still more preferably greater than or equal to 0.2 eV.

As the light-emitting material included in the light-emitting layer 430, any material can be used as long as the material can convert triplet excitation energy into light emission. As an example of the material that can convert triplet excitation energy into light emission, a thermally activated delayed fluorescence material can be given in addition to the phosphorescent material. Therefore, the term "phosphorescent material" in the description can be replaced with the term "thermally activated delayed fluorescence material". Note that the thermally activated delayed fluorescence material is a material that can up-convert a triplet excited state into a singlet excited state (i.e., reverse intersystem crossing is possible) using a little thermal energy and efficiently exhibits light emission (fluorescence) from the singlet excited state. Thermally activated delayed fluorescence is efficiently obtained under the condition where the difference between the triplet excitation energy level and the singlet excitation energy level is more than 0 eV and less than or equal to 0.2 eV, preferably more than 0 eV and less than or equal to 0.1 eV.

The material that emits thermally activated delayed fluorescence may be a material that can form a singlet excited state by itself from a triplet excited state by reverse intersystem crossing or may be a combination of two kinds of materials which form an exciplex.

There is no limitation on the emission colors of the light-emitting material included in the light-emitting layer 420 and the light-emitting material included in the light-emitting layer 430, and they may be the same or different. Light emitted from the light-emitting materials is mixed and extracted out of the element; therefore, for example, in the case where their emission colors are complementary colors, the light-emitting element can emit white light.

Note that the light-emitting layers 420 and 430 can be formed by an evaporation method (including a vacuum evaporation method), an inkjet method, a coating method, gravure printing, or the like.

Note that the structure described above in this embodiment can be combined with any of the structures described in the other embodiments as appropriate.

Embodiment 3

In this embodiment, a display device of one embodiment of the present invention will be described below with reference to FIGS. 9A and 9B, FIGS. 10A and 10B, FIG. 11, FIGS. 12A and 12B, and FIGS. 13A and 13B.

<Structure Example 1 of Display Device>

Figure 9A:
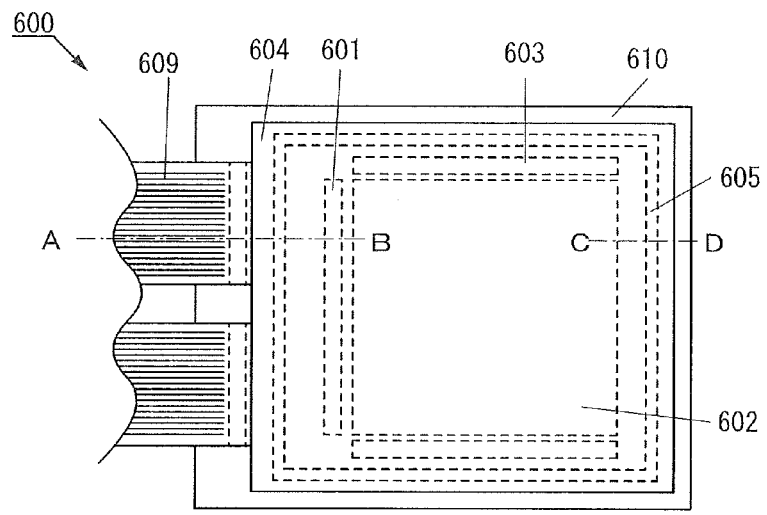
FIGS. 9A and 9B are a top view and a schematic cross-sectional view illustrating a display device of one embodiment of the present invention.
Figure 9B:
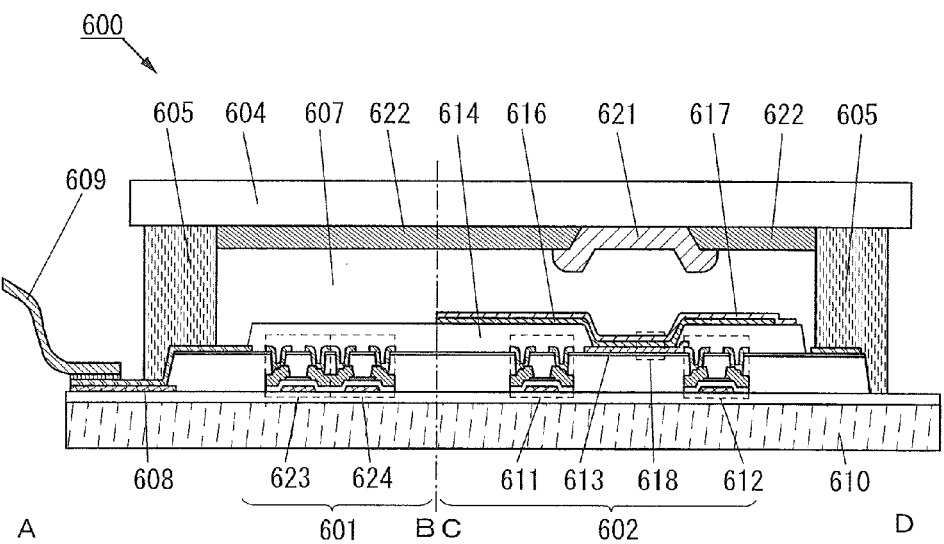

FIG. 9A is a top view illustrating a display device 600 and FIG. 9B is a cross-sectional view taken along the dashed-dotted line A-B and the dashed-dotted line C-D in FIG. 9A. The display device 600 includes driver circuit portions (a signal line driver circuit portion 601 and a scan line driver circuit portion 603) and a pixel portion 602. Note that the signal line driver circuit portion 601, the scan line driver circuit portion 603, and the pixel portion 602 have a function of controlling light emission of a light-emitting element.

The display device 600 also includes an element substrate 610, a sealing substrate 604, a sealant 605, a region 607 surrounded by the sealant 605, a lead wiring 608, and an FPC 609.

Note that the lead wiring 608 is a wiring for transmitting signals to be input to the signal line driver circuit portion 601 and the scan line driver circuit portion 603 and for receiving a video signal, a clock signal, a start signal, a reset signal, and the like from the FPC 609 serving as an external input terminal. Although only the FPC 609 is illustrated here, the FPC 609 may be provided with a printed wiring board (PWB).

As the signal line driver circuit portion 601, a CMOS circuit in which an n-channel transistor 623 and a p-channel transistor 624 are combined is formed. As the signal line driver circuit portion 601 or the scan line driver circuit portion 603, various types of circuits such as a CMOS circuit, a PMOS circuit, or an NMOS circuit can be used. Although a driver in which a driver circuit portion is formed and a pixel are formed over the same surface of a substrate in the display device of this embodiment, the driver circuit portion is not necessarily formed over the substrate and can be formed outside the substrate.

The pixel portion 602 includes a switching transistor 611, a current control transistor 612, and a lower electrode 613 electrically connected to a drain of the current control transistor 612. Note that a partition wall 614 is formed to cover end portions of the lower electrode 613. As the partition wall 614, for example, a positive type photosensitive acrylic resin film can be used.

In order to obtain favorable coverage by a film which is formed over the partition wall 614, the partition wall 614 is formed to have a curved surface with curvature at its upper or lower end portion. For example, in the case of using a positive photosensitive acrylic as a material of the partition wall 614, it is preferable that only the upper end portion of the partition wall 614 have a curved surface with curvature (the radius of the curvature being 0.2 μm to 3 μm). As the partition wall 614, either a negative photosensitive resin or a positive photosensitive resin can be used.

Note that there is no particular limitation on a structure of each of the transistors (the transistors 611, 612, 623, and 624). For example, a staggered transistor can be used. In addition, there is no particular limitation on the polarity of these transistors. For these transistors, n-channel and p-channel transistors may be used, or either n-channel transistors or p-channel transistors may be used, for example. Furthermore, there is no particular limitation on the crystallinity of a semiconductor film used for these transistors. For example, an amorphous semiconductor film or a crystalline semiconductor film may be used. Examples of a semiconductor material include Group 14 semiconductors (e.g., a semiconductor including silicon), compound semiconductors (including oxide semiconductors), organic semiconductors, and the like. For example, it is preferable to use an oxide semiconductor that has an energy gap of 2 eV or more, preferably 2.5 eV or more and further preferably 3 eV or more, for the transistors, so that the off-state current of the transistors can be reduced. Examples of the oxide semiconductor include an In—Ga oxide and an In-M-Zn oxide (M is aluminum (Al), gallium (Ga), yttrium (Y), zirconium (Zr), lanthanum (La), cerium (Ce), tin (Sn), hafnium (Hf), or neodymium (Nd)).

An EL layer 616 and an upper electrode 617 are formed over the lower electrode 613. Here, the lower electrode 613 functions as an anode and the upper electrode 617 functions as a cathode.

In addition, the EL layer 616 is formed by various methods such as an evaporation method with an evaporation mask, an ink jet method, or a spin coating method. As another material included in the EL layer 616, a low molecular compound or a high molecular compound (including an oligomer or a dendrimer) may be used.

Note that a light-emitting element 618 is formed with the lower electrode 613, the EL layer 616, and the upper electrode 617. The light-emitting element 618 has the structure described in Embodiment 1. In the case where the pixel portion includes a plurality of light-emitting elements, the pixel portion may include both the light-emitting element described in Embodiment 1 and a light-emitting element having a different structure.

When the sealing substrate 604 and the element substrate 610 are attached to each other with the sealant 605, the light-emitting element 618 is provided in the region 607 surrounded by the element substrate 610, the sealing substrate 604, and the sealant 605. The region 607 is filled with a filler. In some cases, the region 607 is filled with an inert gas (nitrogen, argon, or the like) or filled with an ultraviolet curable resin or a thermosetting resin which can be used for the sealant 605. For example, a polyvinyl chloride (PVC)-based resin, an acrylic-based resin, a polyimide-based resin, an epoxy-based resin, a silicone-based resin, a polyvinyl butyral (PVB)-based resin, or an ethylene vinyl acetate (EVA)-based resin can be used. It is preferable that the sealing substrate be provided with a recessed portion and the desiccant be provided in the recessed portion, in which case deterioration due to influence of moisture can be inhibited.

An optical element 621 is provided below the sealing substrate 604 to overlap with the light-emitting element 618. A light-blocking layer 622 is provided below the sealing substrate 604. The structures of the optical element 621 and the light-blocking layer 622 can be the same as those of the optical element and the light-blocking layer in Embodiment 1, respectively.

An epoxy-based resin or glass frit is preferably used for the sealant 605. It is preferable that such a material do not transmit moisture or oxygen as much as possible. As the sealing substrate 604, a glass substrate, a quartz substrate, or a plastic substrate formed of fiber reinforced plastic (FRP), poly(vinyl fluoride) (PVF), polyester, acrylic, or the like can be used.

In the above-described manner, the display device including the light-emitting element and the optical element which are described in Embodiment 1 can be obtained.

<Structure Example 2 of Display Device>

Figure 11:
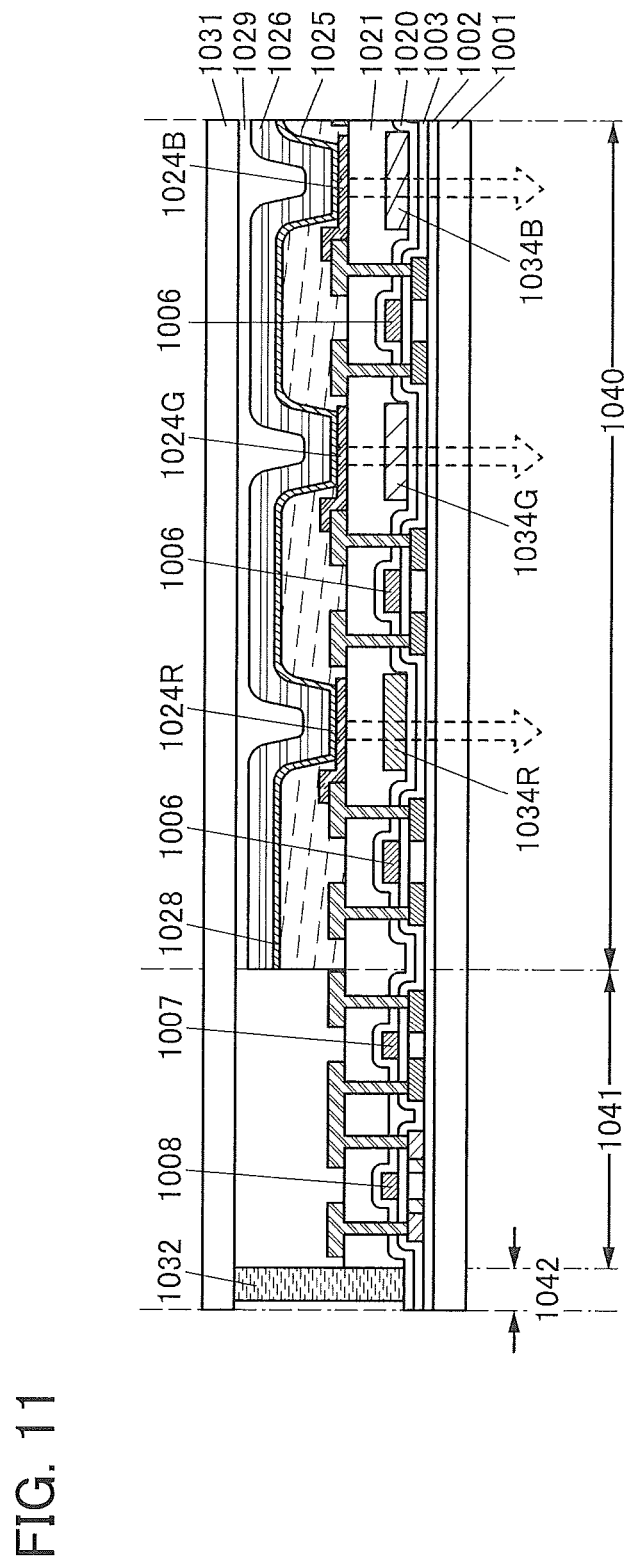
FIG. 11 is a schematic cross-sectional view illustrating a display device of one embodiment of the present invention.

Next, another example of the display device is described with reference to FIGS. 10A and 10B and FIG. 11. Note that FIGS. 10A and 10B and FIG. 11 are each a cross-sectional view of a display device of one embodiment of the present invention.

In FIG. 10A, a substrate 1001, a base insulating film 1002, a gate insulating film 1003, gate electrodes 1006, 1007, and 1008, a first interlayer insulating film 1020, a second interlayer insulating film 1021, a peripheral portion 1042, a pixel portion 1040, a driver circuit portion 1041, lower electrodes 1024R, 1024G, and 1024B of light-emitting elements, a partition wall 1025, an EL layer 1028, an upper electrode 1026 of the light-emitting elements, a sealing layer 1029, a sealing substrate 1031, a sealant 1032, and the like are illustrated.

In FIG. 10A, examples of the optical elements, coloring layers (a red coloring layer 1034R, a green coloring layer 1034G, and a blue coloring layer 1034B) are provided on a transparent base material 1033. Further, a light-blocking layer 1035 may be provided. The transparent base material 1033 provided with the coloring layers and the light-blocking layer is positioned and fixed to the substrate 1001. Note that the coloring layers and the light-blocking layer are covered with an overcoat layer 1036. In the structure in FIG. 10A, red light, green light, and blue light transmit the coloring layers, and thus an image can be displayed with the use of pixels of three colors.

FIG. 10B illustrates an example in which, as examples of the optical elements, the coloring layers (the red coloring layer 1034R, the green coloring layer 1034G, and the blue coloring layer 1034B) are provided between the gate insulating film 1003 and the first interlayer insulating film 1020. As in this structure, the coloring layers may be provided between the substrate 1001 and the sealing substrate 1031.

FIG. 11 illustrates an example in which, as examples of the optical elements, the coloring layers (the red coloring layer 1034R, the green coloring layer 1034G, and the blue coloring layer 1034B) are provided between the first interlayer insulating film 1020 and the second interlayer insulating film 1021. As in this structure, the coloring layers may be provided between the substrate 1001 and the sealing substrate 1031.

The above-described display device has a structure in which light is extracted from the substrate 1001 side where the transistors are formed (a bottom-emission structure), but may have a structure in which light is extracted from the sealing substrate 1031 side (a top-emission structure).

<Structure Example 3 of Display Device>

FIGS. 12A and 12B and FIGS. 13A and 13B are each an example of a cross-sectional view of a display device having a top emission structure. Note that FIGS. 12A and 12B and FIGS. 13A and 13B are each a cross-sectional view illustrating the display device of one embodiment of the present invention, and the driver circuit portion 1041, the peripheral portion 1042, and the like, which are illustrated in FIGS. 10A and 10B and FIG. 11, are not illustrated therein.

In this case, as the substrate 1001, a substrate that does not transmit light can be used. The process up to the step of forming a connection electrode which connects the transistor and the anode of the light-emitting element is performed in a manner similar to that of the display device having a bottom-emission structure. Then, a third interlayer insulating film 1037 is formed to cover an electrode 1022. This insulating film may have a planarization function. The third interlayer insulating film 1037 can be formed by using a material similar to that of the second interlayer insulating film, or can be formed by using any other known materials.

Figure 12A:
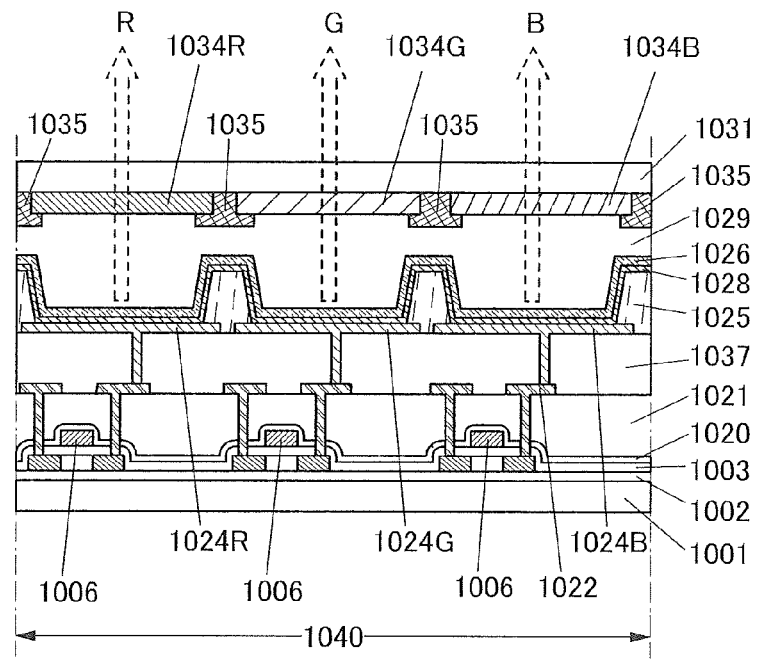
FIGS. 12A and 12B are schematic cross-sectional views each illustrating a display device of one embodiment of the present invention.
Figure 12B:
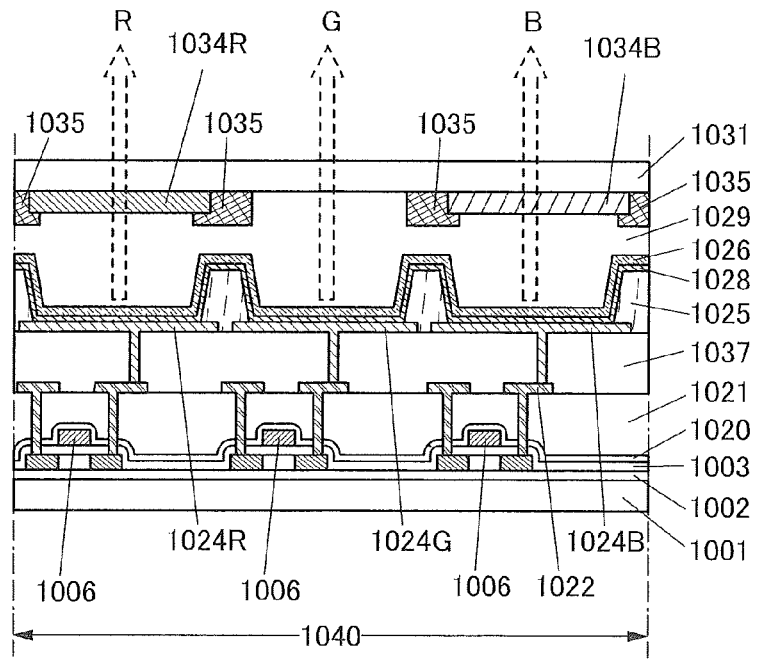

The lower electrodes 1024R, 1024G, and 1024B of the light-emitting elements each function as an anode here, but may function as a cathode. Further, in the case of a display device having a top-emission structure as illustrated in FIGS. 12A and 12B, the lower electrodes 10248, 1024G, and 1024B preferably have a function of reflecting light. The upper electrode 1026 is provided over the EL layer 1028. It is preferable that the upper electrode 1026 have a function of reflecting light and a function of transmitting light and that a microcavity structure be used between the upper electrode 1026 and the lower electrodes 1024R, 1024G, and 1024B, in which case the intensity of light having a specific wavelength is increased.

In the case of a top-emission structure as illustrated in FIG. 12A, sealing can be performed with the sealing substrate 1031 on which the coloring layers (the red coloring layer 1034R, the green coloring layer 1034G, and the blue coloring layer 1034B) are provided. The sealing substrate 1031 may be provided with the light-blocking layer 1035 which is positioned between pixels. Note that a light-transmitting substrate is favorably used as the sealing substrate 1031.

FIG. 12A illustrates the structure provided with the light-emitting elements and the coloring layers for the light-emitting elements as an example; however, the structure is not limited thereto. For example, as shown in FIG. 12B, a structure including the red coloring layer 1034R and the blue coloring layer 1034B but not including a green coloring layer may be employed to achieve full color display with the three colors of red, green, and blue. The structure as illustrated in FIG. 12A where the light-emitting elements are provided with the coloring layers is effective to suppress reflection of external light. In contrast, the structure as illustrated in FIG. 12B where the light-emitting elements are provided with the red coloring layer and the blue coloring layer and without the green coloring layer is effective to reduce power consumption because of small energy loss of light emitted from the green light-emitting element.

<Structure Example 4 of Display Device>

Figure 13A:
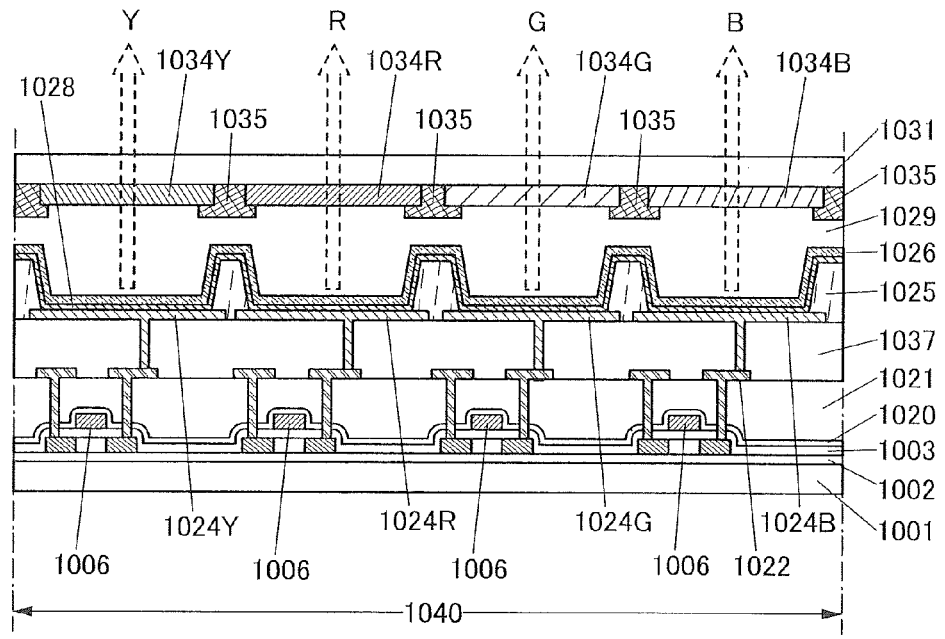
FIGS. 13A and 13B are schematic cross-sectional views each illustrating a display device of one embodiment of the present invention.
Figure 13B:
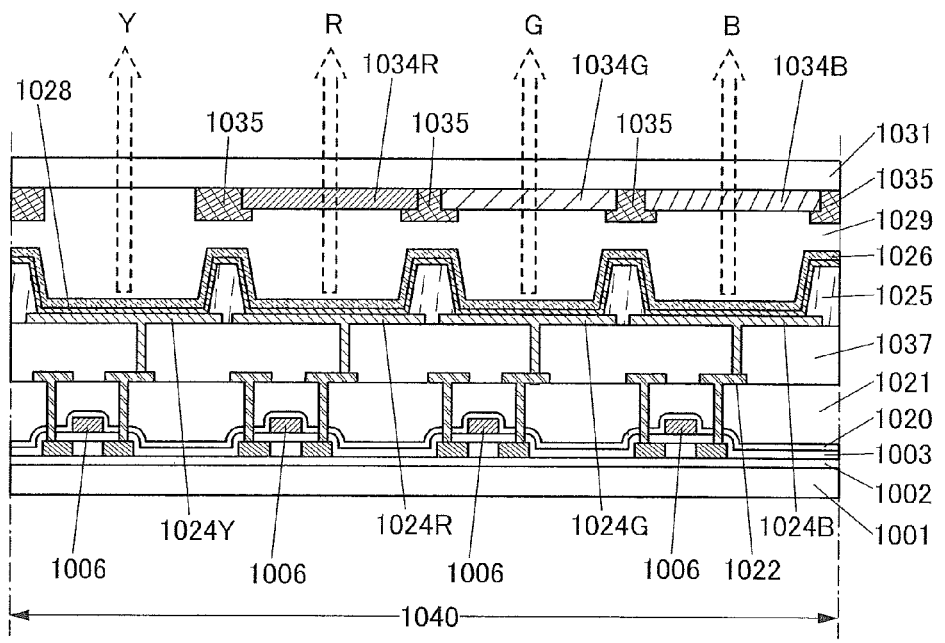

Although a display device including sub-pixels of three colors (red, green, and blue) is described above as an example, the number of colors of sub-pixels may be four (red, green, blue, and yellow, or red, green, blue, and white). FIGS. 13A and 13B illustrate structures of display devices each including the lower electrodes 1024R, 1024G, 1024B, and 1024Y. A light-emitting element including the lower electrode 1024Y preferably has a microcavity structure between the lower electrode and the upper electrode 1026 as in the display device illustrated in FIG. 12A. In the display device illustrated in FIG. 13A, sealing can be performed with the sealing substrate 1031 on which the coloring layers (the red coloring layer 1034R, the green coloring layer 1034G, the blue coloring layer 1034B, and the yellow coloring layer 1034Y) are provided.

Light emitted through the microcavity and the yellow coloring layer 1034Y has an emission spectrum in a yellow region. Since yellow is a color with a high luminosity factor, a light-emitting element emitting yellow light has high emission efficiency. Therefore, the display device of FIG. 13A can reduce power consumption.

FIG. 13A illustrates the structure provided with the light-emitting elements and the coloring layers for the light-emitting elements as an example; however, the structure is not limited thereto. For example, as shown in FIG. 13B, a structure including the red coloring layer 1034R, the green coloring layer 1034G, and the blue coloring layer 1034B but not including a yellow coloring layer may be employed to achieve full color display with the four colors of red, green, blue, and yellow. The structure as illustrated in FIG. 13A where the light-emitting elements are provided with the coloring layers is effective to suppress reflection of external light. In contrast, the structure as illustrated in FIG. 13B where the light-emitting elements are provided with the red coloring layer, the green coloring layer, and the blue coloring layer and without the yellow coloring layer is effective to reduce power consumption because of small energy loss of light emitted from the green light-emitting element.

The structure described in this embodiment can be combined with any of the structures in this embodiment and the other embodiments.

Embodiment 4

In this embodiment, a display device including a light-emitting element of one embodiment of the present invention will be described with reference to FIGS. 14A and 14B, FIGS. 15A and 15B, and FIGS. 16A and 16B.

Figure 14A:
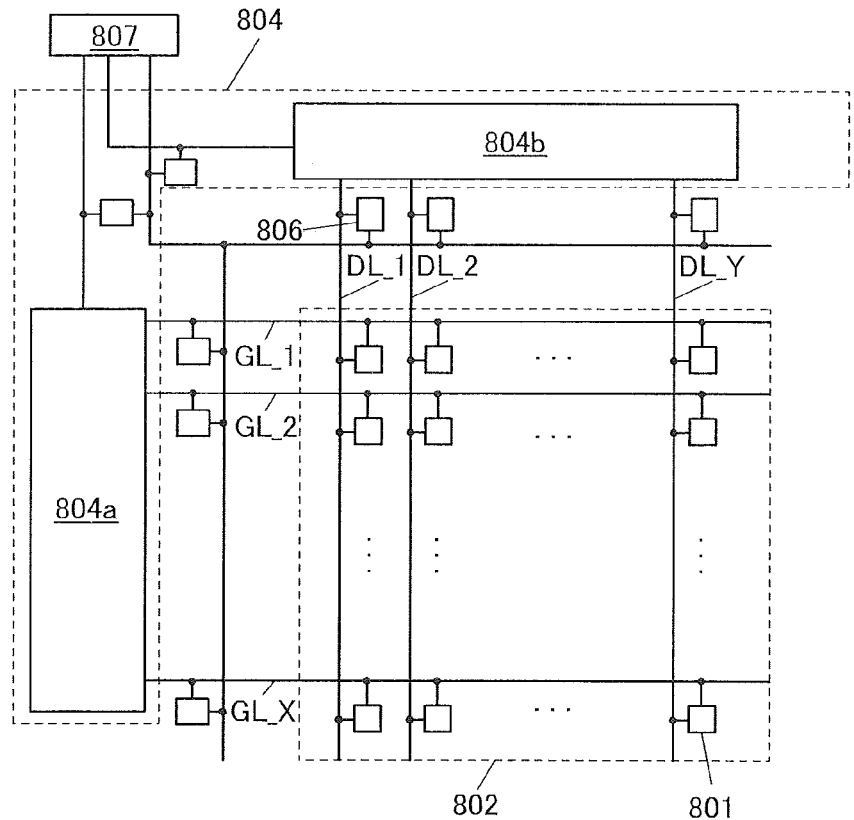
FIGS. 14A and 14B are a block diagram and a circuit diagram illustrating a display device of one embodiment of the present invention.
Figure 14B:
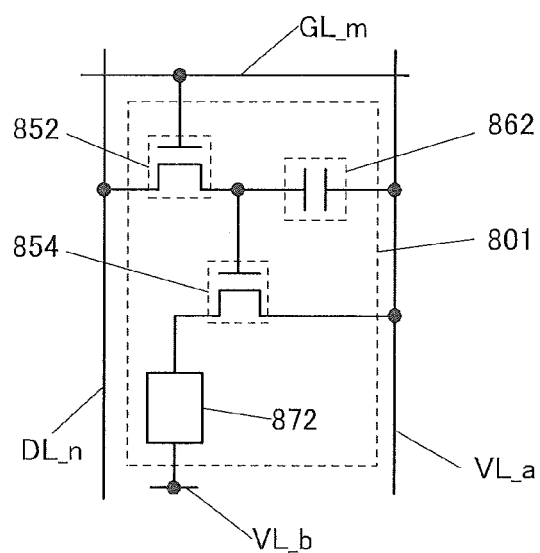

FIG. 14A is a block diagram illustrating the display device of one embodiment of the present invention, and FIG. 14B is a circuit diagram illustrating a pixel circuit of the display device of one embodiment of the present invention.

<Description of Display Device>

The display device illustrated in FIG. 14A includes a region including pixels of display elements (the region is hereinafter referred to as a pixel portion 802), a circuit portion provided outside the pixel portion 802 and including circuits for driving the pixels (the portion is hereinafter referred to as a driver circuit portion 804), circuits having a function of protecting elements (the circuits are hereinafter referred to as protection circuits 806), and a terminal portion 807. Note that the protection circuits 806 are not necessarily provided.

A part or the whole of the driver circuit portion 804 is preferably formed over a substrate over which the pixel portion 802 is formed, in which case the number of components and the number of terminals can be reduced. When a part or the whole of the driver circuit portion 804 is not formed over the substrate over which the pixel portion 802 is formed, the part or the whole of the driver circuit portion 804 can be mounted by COG or tape automated bonding (TAB).

The pixel portion 802 includes a plurality of circuits for driving display elements arranged in X rows (X is a natural number of 2 or more) and Y columns (Y is a natural number of 2 or more) (such circuits are hereinafter referred to as pixel circuits 801). The driver circuit portion 804 includes driver circuits such as a circuit for supplying a signal (scan signal) to select a pixel (the circuit is hereinafter referred to as a scan line driver circuit 804a) and a circuit for supplying a signal (data signal) to drive a display element in a pixel (the circuit is hereinafter referred to as a signal line driver circuit 804b).

The scan line driver circuit 804a includes a shift register or the like. Through the terminal portion 807, the scan line driver circuit 804a receives a signal for driving the shift register and outputs a signal. For example, the scan line driver circuit 804a receives a start pulse signal, a clock signal, or the like and outputs a pulse signal. The scan line driver circuit 804a has a function of controlling the potentials of wirings supplied with scan signals (such wirings are hereinafter referred to as scan lines GL_1 to GL_X). Note that a plurality of scan line driver circuits 804a may be provided to control the scan lines GL_1 to GL_X separately. Alternatively, the scan line driver circuit 804a has a function of supplying an initialization signal. Without being limited thereto, the scan line driver circuit 804a can supply another signal.

The signal line driver circuit 804b includes a shift register or the like. The signal line driver circuit 804b receives a signal (video signal) from which a data signal is derived, as well as a signal for driving the shift register, through the terminal portion 807. The signal line driver circuit 804b has a function of generating a data signal to be written to the pixel circuit 801 which is based on the video signal. In addition, the signal line driver circuit 804b has a function of controlling output of a data signal in response to a pulse signal produced by input of a start pulse signal, a clock signal, or the like. Furthermore, the signal line driver circuit 804b has a function of controlling the potentials of wirings supplied with data signals (such wirings are hereinafter referred to as data lines DL_1 to DL_Y). Alternatively, the signal line driver circuit 804b has a function of supplying an initialization signal. Without being limited thereto, the signal line driver circuit 804b can supply another signal.

The signal line driver circuit 804b includes a plurality of analog switches or the like, for example. The signal line driver circuit 804b can output, as the data signals, signals obtained by time-dividing the video signal by sequentially turning on the plurality of analog switches. The signal line driver circuit 804b may include a shift register or the like.

A pulse signal and a data signal are input to each of the plurality of pixel circuits 801 through one of the plurality of scan lines GL supplied with scan signals and one of the plurality of data lines DL supplied with data signals, respectively. Writing and holding of the data signal to and in each of the plurality of pixel circuits 801 are controlled by the scan line driver circuit 804a. For example, to the pixel circuit 801 in the m-th row and the n-th column (m is a natural number of less than or equal to X, and n is a natural number of less than or equal to Y), a pulse signal is input from the scan line driver circuit 804a through the scan line GL_m, and a data signal is input from the signal line driver circuit 804b through the data line DL_n in accordance with the potential of the scan line GL₁m.

The protection circuit 806 shown in FIG. 14A is connected to, for example, the scan line GL between the scan line driver circuit 804a and the pixel circuit 801. Alternatively, the protection circuit 806 is connected to the data line DL between the signal line driver circuit 804b and the pixel circuit 801. Alternatively, the protection circuit 806 can be connected to a wiring between the scan line driver circuit 804a and the terminal portion 807. Alternatively, the protection circuit 806 can be connected to a wiring between the signal line driver circuit 804b and the terminal portion 807. Note that the terminal portion 807 means a portion having terminals for inputting power, control signals, and video signals to the display device from external circuits.

The protection circuit 806 is a circuit that electrically connects a wiring connected to the protection circuit to another wiring when a potential out of a certain range is applied to the wiring connected to the protection circuit.

As illustrated in FIG. 14A, the protection circuits 806 are provided for the pixel portion 802 and the driver circuit portion 804, so that the resistance of the display device to overcurrent generated by electrostatic discharge (ESD) or the like can be improved. Note that the configuration of the protection circuits 806 is not limited to that, and for example, a configuration in which the protection circuits 806 are connected to the scan line driver circuit 804a or a configuration in which the protection circuits 806 are connected to the signal line driver circuit 804b may be employed. Alternatively, the protection circuits 806 may be configured to be connected to the terminal portion 807.

In FIG. 14A, an example in which the driver circuit portion 804 includes the scan line driver circuit 804a and the signal line driver circuit 804b is shown; however, the structure is not limited thereto. For example, only the scan line driver circuit 804a may be formed and a separately prepared substrate where a signal line driver circuit is formed (e.g., a driver circuit substrate formed with a single crystal semiconductor film or a polycrystalline semiconductor film) may be mounted.

<Structural Example of Pixel Circuit>
Each of the plurality of pixel circuits 801 in FIG. 14A can have a structure illustrated in FIG. 14B, for example.

The pixel circuit 801 illustrated in FIG. 14B includes transistors 852 and 854, a capacitor 862, and a light-emitting element 872.

One of a source electrode and a drain electrode of the transistor 852 is electrically connected to a wiring to which a data signal is supplied (a data line DL_n). A gate electrode of the transistor 852 is electrically connected to a wiring to which a gate signal is supplied (a scan line GL_m).

The transistor 852 has a function of controlling whether to write a data signal.

One of a pair of electrodes of the capacitor 862 is electrically connected to a wiring to which a potential is supplied (hereinafter referred to as a potential supply line VL_a), and the other is electrically connected to the other of the source electrode and the drain electrode of the transistor 852.

The capacitor 862 functions as a storage capacitor for storing written data.

One of a source electrode and a drain electrode of the transistor 854 is electrically connected to the potential supply line VL_a. Furthermore, a gate electrode of the transistor 854 is electrically connected to the other of the source electrode and the drain electrode of the transistor 852.

One of an anode and a cathode of the light-emitting element 872 is electrically connected to a potential supply line VL_b, and the other is electrically connected to the other of the source electrode and the drain electrode of the transistor 854.

As the light-emitting element 872, any of the light-emitting elements described in Embodiment 1 can be used.

Note that a high power supply potential VDD is supplied to one of the potential supply line VL_a and the potential supply line VL_b, and a low power supply potential VSS is supplied to the other.

In the display device including the pixel circuits 801 in FIG. 14B, the pixel circuits 801 are sequentially selected row by row by the scan line driver circuit 804a in FIG. 14A, for example, whereby the transistors 852 are turned on and a data signal is written.

When the transistors 852 are turned off, the pixel circuits 801 in which the data has been written are brought into a holding state. Furthermore, the amount of current flowing between the source electrode and the drain electrode of the transistor 854 is controlled in accordance with the potential of the written data signal. The light-emitting element 872 emits light with a luminance corresponding to the amount of flowing current. This operation is sequentially performed row by row; thus, an image is displayed.

Alternatively, the pixel circuit can have a function of compensating variation in threshold voltages or the like of a transistor. FIGS. 15A and 15B and FIGS. 16A and 16B illustrate examples of the pixel circuit.

Figure 15A:
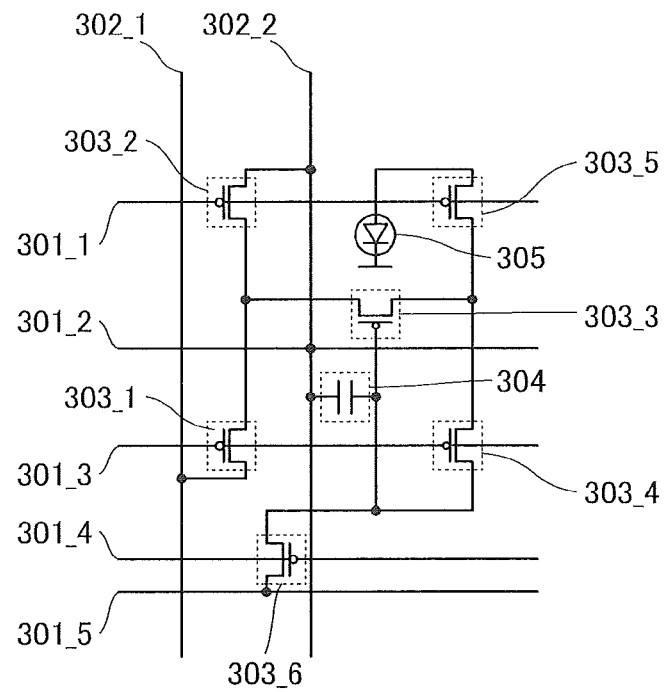
FIGS. 15A and 15B are circuit diagrams each illustrating a pixel circuit of a display device of one embodiment of the present invention.

The pixel circuit illustrated in FIG. 15A includes six transistors (transistors 303_1 to 303_6), a capacitor 304, and a light-emitting element 305. The pixel circuit illustrated in FIG. 15A is electrically connected to wirings 301_1 to 301_5 and wirings 302_1 and 302_2. Note that as the transistors 303_1 to 303_6, for example, p-channel transistors can be used.

Figure 15B:
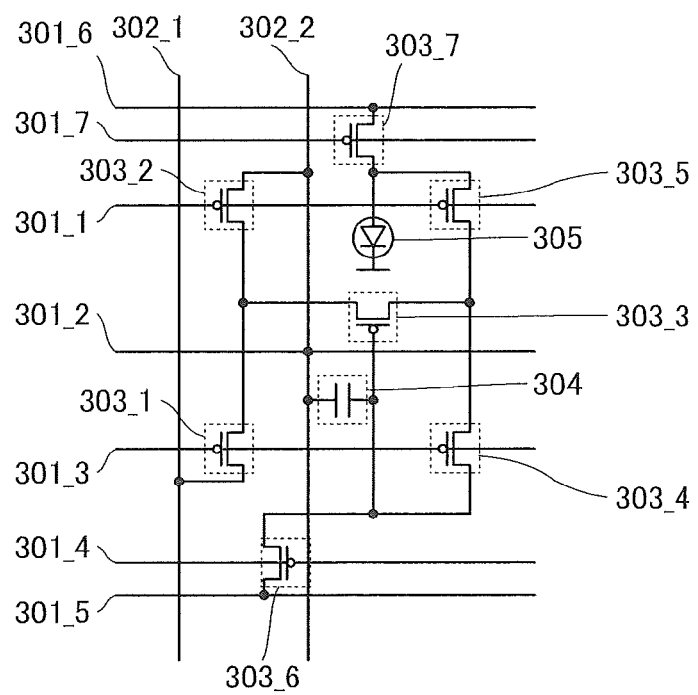

The pixel circuit shown in FIG. 15B has a configuration in which a transistor 303_7 is added to the pixel circuit shown in FIG. 15A. The pixel circuit illustrated in FIG. 15B is electrically connected to wirings 301_6 and 301_7. The wirings 301_5 and 301_6 may be electrically connected to each other. Note that as the transistor 303_7, for example, a p-channel transistor can be used.

Figure 16A:
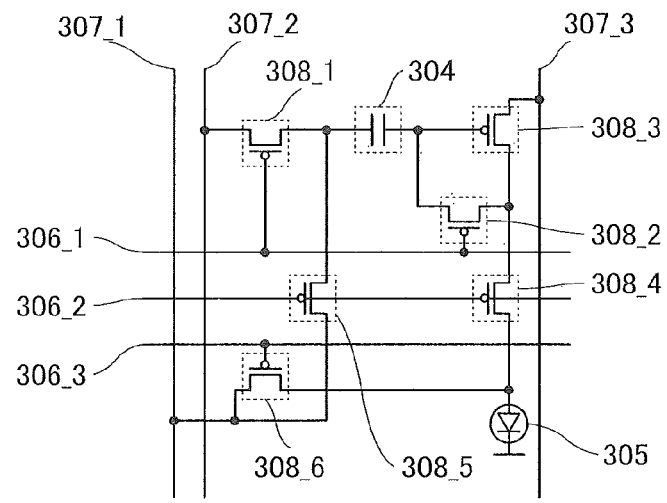
FIGS. 16A and 16B are circuit diagrams each illustrating a pixel circuit of a display device of one embodiment of the present invention.

The pixel circuit shown in FIG. 16A includes six transistors (transistors 308_1 to 308_6), the capacitor 304, and the light-emitting element 305. The pixel circuit illustrated in FIG. 16A is electrically connected to wirings 306_1 to 306_3 and wirings 307_1 to 307_3. The wirings 306_1 and 306_3 may be electrically connected to each other. Note that as the transistors 308_1 to 308_6, for example, p-channel transistors can be used.

Figure 16B:
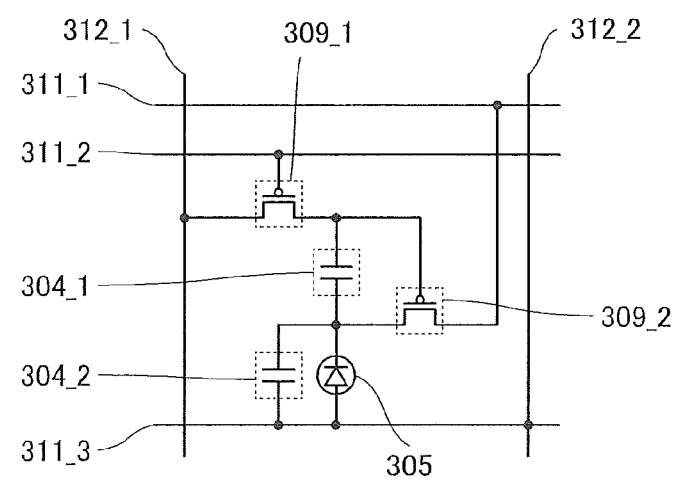

The pixel circuit illustrated in FIG. 16B includes two transistors (transistors 309_1 and 309_2), two capacitors (capacitors 304_1 and 304_2), and the light-emitting element 305. The pixel circuit illustrated in FIG. 16B is electrically connected to wirings 311_1 to 311_3 and wirings 312_1 and 312_2. With the configuration of the pixel circuit illustrated in FIG. 16B, the pixel circuit illustrated in FIG. 16B can be driven by a voltage inputting current driving method (also referred to as CVCC). Note that as the transistors 309_1 and 309_2, for example, p-channel transistors can be used.

A light-emitting element of one embodiment of the present invention can be used for an active matrix method in which an active element is included in a pixel of a display device or a passive matrix method in which an active element is not included in a pixel of a display device.

In the active matrix method, as an active element (a non-linear element), not only a transistor but also a variety of active elements (non-linear elements) can be used. For example, a metal insulator metal (MIM), a thin film diode (TFD), or the like can also be used. Since these elements can be formed with a smaller number of manufacturing steps, manufacturing cost can be reduced or yield can be improved. Alternatively, since the size of these elements is small, the aperture ratio can be improved, so that power consumption can be reduced or higher luminance can be achieved.

As a method other than the active matrix method, the passive matrix method in which an active element (a non-linear element) is not used can also be used. Since an active element (a non-linear element) is not used, the number of manufacturing steps is small, so that manufacturing cost can be reduced or yield can be improved. Alternatively, since an active element (a non-linear element) is not used, the aperture ratio can be improved, so that power consumption can be reduced or higher luminance can be achieved, for example.

The structure described in this embodiment can be combined with any of the structures described in the other embodiments as appropriate.

Embodiment 5

In this embodiment, a display device including a light-emitting element of one embodiment of the present invention and an electronic device in which the display device is provided with an input device will be described with reference to FIGS. 17A and 17B, FIGS. 18A to 18C, FIGS. 19A and 19B, FIGS. 20A and 20B, and FIG. 21.

<Description 1 of Touch Panel>

In this embodiment, a touch panel 2000 including a display device and an input device will be described as an example of an electronic device. In addition, an example in which a touch sensor is used as an input device will be described.

Figure 17A:
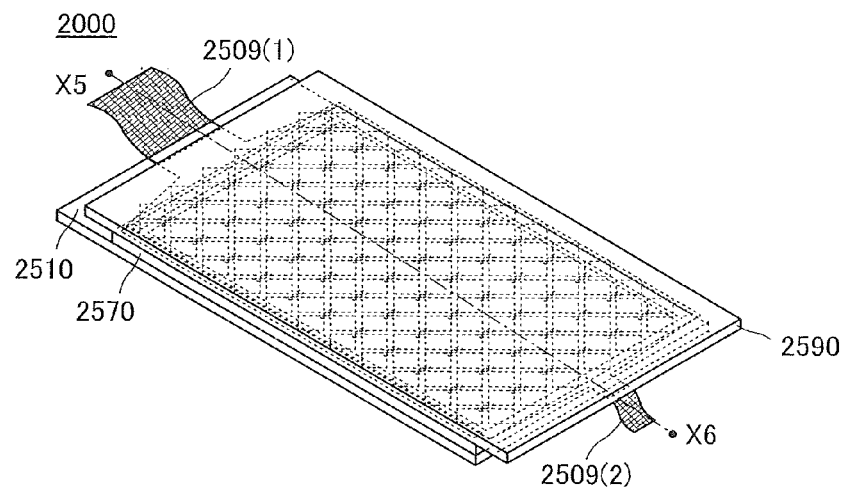
FIGS. 17A and 17B are perspective views illustrating an example of a touch panel of one embodiment of the present invention.
Figure 17B:
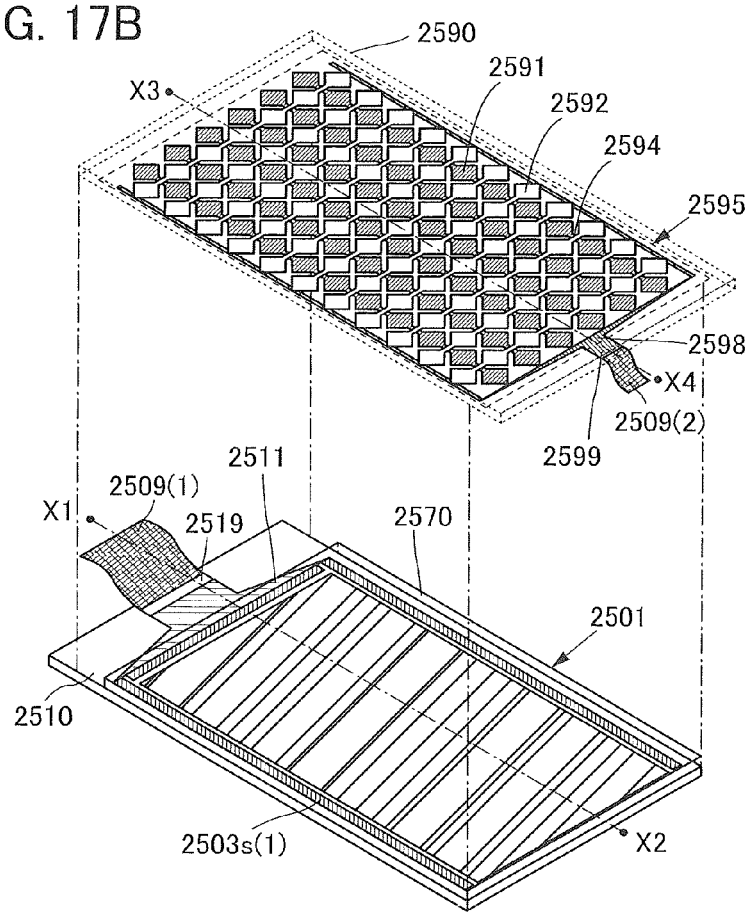

FIGS. 17A and 17B are perspective views of the touch panel 2000. Note that FIGS. 17A and 17B illustrate only main components of the touch panel 2000 for simplicity.

The touch panel 2000 includes a display device 2501 and a touch sensor 2595 (see FIG. 17B). The touch panel 2000 also includes a substrate 2510, a substrate 2570, and a substrate 2590. The substrate 2510, the substrate 2570, and the substrate 2590 each have flexibility. Note that one or all of the substrates 2510, 2570, and 2590 may be inflexible.

The display device 2501 includes a plurality of pixels over the substrate 2510 and a plurality of wirings 2511 through which signals are supplied to the pixels. The plurality of wirings 2511 are led to a peripheral portion of the substrate 2510, and parts of the plurality of wirings 2511 form a terminal 2519. The terminal 2519 is electrically connected to an FPC 2509(1). The plurality of wirings 2511 can supply signals from a signal line driver circuit 2503s(1) to the plurality of pixels.

The substrate 2590 includes the touch sensor 2595 and a plurality of wirings 2598 electrically connected to the touch sensor 2595. The plurality of wirings 2598 are led to a peripheral portion of the substrate 2590, and parts of the plurality of wirings 2598 form a terminal. The terminal is electrically connected to an FPC 2509(2). Note that in FIG. 17B, electrodes, wirings, and the like of the touch sensor 2595 provided on the back side of the substrate 2590 (the side facing the substrate 2510) are indicated by solid lines for clarity.

As the touch sensor 2595, a capacitive touch sensor can be used. Examples of the capacitive touch sensor are a surface capacitive touch sensor and a projected capacitive touch sensor.

Examples of the projected capacitive touch sensor are a self capacitive touch sensor and a mutual capacitive touch sensor, which differ mainly in the driving method. The use of a mutual capacitive type is preferable because multiple points can be sensed simultaneously.

Note that the touch sensor 2595 illustrated in FIG. 17B is an example of using a projected capacitive touch sensor.

Note that a variety of sensors that can sense proximity or touch of a sensing target such as a finger can be used as the touch sensor 2595.

The projected capacitive touch sensor 2595 includes electrodes 2591 and electrodes 2592. The electrodes 2591 are electrically connected to any of the plurality of wirings 2598, and the electrodes 2592 are electrically connected to any of the other wirings 2598.

The electrodes 2592 each have a shape of a plurality of quadrangles arranged in one direction with one corner of a quadrangle connected to one corner of another quadrangle as illustrated in FIGS. 17A and 17B.

The electrodes 2591 each have a quadrangular shape and are arranged in a direction intersecting with the direction in which the electrodes 2592 extend.

A wiring 2594 electrically connects two electrodes 2591 between which the electrode 2592 is positioned. The intersecting area of the electrode 2592 and the wiring 2594 is preferably as small as possible. Such a structure allows a reduction in the area of a region where the electrodes are not provided, reducing variation in transmittance. As a result, variation in luminance of light passing through the touch sensor 2595 can be reduced.

Note that the shapes of the electrodes 2591 and the electrodes 2592 are not limited thereto and can be any of a variety of shapes. For example, a structure may be employed in which the plurality of electrodes 2591 are arranged so that gaps between the electrodes 2591 are reduced as much as possible, and the electrodes 2592 are spaced apart from the electrodes 2591 with an insulating layer interposed therebetween to have regions not overlapping with the electrodes 2591. In this case, it is preferable to provide, between two adjacent electrodes 2592, a dummy electrode electrically insulated from these electrodes because the area of regions having different transmittances can be reduced.

<Description of Display Device>

Figure 18A:
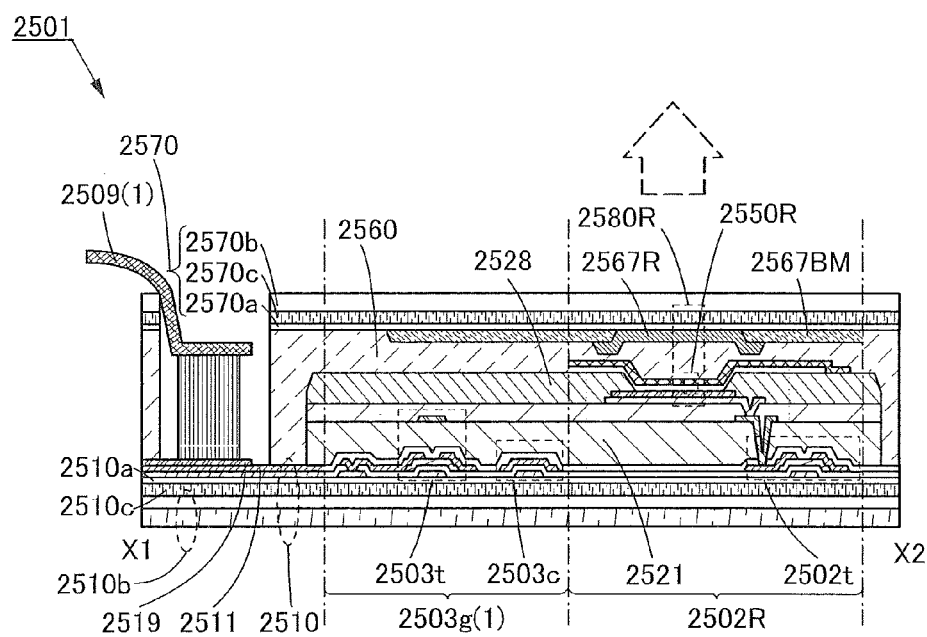
FIGS. 18A to 18C are schematic cross-sectional views illustrating examples of a display device and a touch sensor of one embodiment of the present invention.

Next, the display device 2501 will be described in detail with reference to FIG. 18A. FIG. 18A corresponds to a cross-sectional view taken along dashed-dotted line X1-X2 in FIG. 17B.

The display device 2501 includes a plurality of pixels arranged in a matrix. Each of the pixels includes a display element and a pixel circuit for driving the display element.

In the following description, an example of using a light-emitting element that emits white light as a display element will be described; however, the display element is not limited to such an element. For example, light-emitting elements that emit light of different colors may be included so that the light of different colors can be emitted from adjacent pixels.

For the substrate 2510 and the substrate 2570, for example, a flexible material with a vapor permeability of lower than or equal to $1\times10^{-5}$ g·m$^{-2}$·day$^{-1}$, preferably lower than or equal to $1\times10^{-6}$ g·m$^{-2}$·day$^{-1}$ can be favorably used. Alternatively, materials whose thermal expansion coefficients are substantially equal to each other are preferably used for the substrate 2510 and the substrate 2570. For example, the coefficients of linear expansion of the materials are preferably lower than or equal to $1\times10^{-3}$/K, further preferably lower than or equal to $5\times10^{-5}$/K, and still further preferably lower than or equal to $1\times10^{-5}$/K.

Note that the substrate 2510 is a stacked body including an insulating layer 2510*a* for preventing impurity diffusion into the light-emitting element, a flexible substrate 2510*b*, and an adhesive layer 2510*c* for attaching the insulating layer 2510*a* and the flexible substrate 2510*b* to each other. The substrate 2570 is a stacked body including an insulating layer 2570*a* for preventing impurity diffusion into the light-emitting element, a flexible substrate 2570*b*, and an adhesive layer 2570*c* for attaching the insulating layer 2570*a* and the flexible substrate 2570*b* to each other.

For the adhesive layer 2510*c* and the adhesive layer 2570*c*, for example, polyester, polyolefin, polyamide (e.g., nylon, aramid), polyimide, polycarbonate, or acrylic, urethane, or epoxy can be used. Alternatively, a material that includes a resin having a siloxane bond can be used.

A sealing layer 2560 is provided between the substrate 2510 and the substrate 2570. The sealing layer 2560 preferably has a refractive index higher than that of air. In the case where light is extracted to the sealing layer 2560 side as illustrated in FIG. 18A, the sealing layer 2560 can also serve as an optical adhesive layer.

A sealant may be formed in the peripheral portion of the sealing layer 2560. With the use of the sealant, a light-emitting element 2550R can be provided in a region surrounded by the substrate 2510, the substrate 2570, the sealing layer 2560, and the sealant. Note that an inert gas (such as nitrogen or argon) may be used instead of the sealing layer 2560. A drying agent may be provided in the inert gas so as to adsorb moisture or the like. An ultraviolet curable resin or a heat curable resin may be used. An epoxy-based resin or a glass frit is preferably used as the sealant. As a material used for the sealant, a material which is impermeable to moisture or oxygen is preferably used.

The display device 2501 includes a pixel 2502R. The pixel 2502R includes a light-emitting module 2580R.

The pixel 2502R includes the light-emitting element 2550R and a transistor 2502*t* that can supply electric power to the light-emitting element 2550R. Note that the transistor 2502*t* functions as part of the pixel circuit. The light-emitting module 2580R includes the light-emitting element 2550R and a coloring layer 2567R.

The light-emitting element 2550R includes a lower electrode, an upper electrode, and an EL layer between the lower electrode and the upper electrode. As the light-emitting element 2550R, any of the light-emitting elements described in Embodiment 1 can be used.

A microcavity structure may be employed between the lower electrode and the upper electrode so as to increase the intensity of light having a specific wavelength.

In the case where the sealing layer 2560 is provided on the light extraction side, the sealing layer 2560 is in contact with the light-emitting element 2550R and the coloring layer 2567R.

The coloring layer 2567R is positioned in a region overlapping with the light-emitting element 2550R. Accordingly, part of light emitted from the light-emitting element 2550R passes through the coloring layer 2567R and is emitted to the outside of the light-emitting module 2580R as indicated by an arrow in FIG. 18A.

The display device 2501 includes a light-blocking layer 2567BM on the light extraction side. The light-blocking layer 2567BM is provided so as to surround the coloring layer 2567R.

The coloring layer 2567R is a coloring layer having a function of transmitting light in a particular wavelength region. For example, a color filter for transmitting light in a red wavelength region, a color filter for transmitting light in a green wavelength region, a color filter for transmitting light in a blue wavelength region, a color filter for transmitting light in a yellow wavelength region, or the like can be used. Each color filter can be formed with any of various materials by a printing method, an inkjet method, an etching method using a photolithography technique, or the like.

An insulating layer 2521 is provided in the display device 2501. The insulating layer 2521 covers the transistor 2502*t*. Note that the insulating layer 2521 has a function of covering unevenness caused by the pixel circuit. The insulating layer 2521 may have a function of suppressing impurity diffusion. This can prevent the reliability of the transistor 2502*t* or the like from being lowered by impurity diffusion.

The light-emitting element 2550R is formed over the insulating layer 2521. A partition 2528 is provided so as to overlap with an end portion of the lower electrode of the light-emitting element 2550R. Note that a spacer for controlling the distance between the substrate 2510 and the substrate 2570 may be formed over the partition 2528.

A scan line driver circuit 2503*g*(1) includes a transistor 2503*t* and a capacitor 2503*c*. Note that the driver circuit can be formed in the same process and over the same substrate as those of the pixel circuits.

The wirings 2511 through which signals can be supplied are provided over the substrate 2510. The terminal 2519 is provided over the wirings 2511. The FPC 2509(1) is electrically connected to the terminal 2519. The FPC 2509(1) has a function of supplying a video signal, a clock signal, a start signal, a reset signal, or the like. Note that the FPC 2509(1) may be provided with a PWB.

Figure 18B:
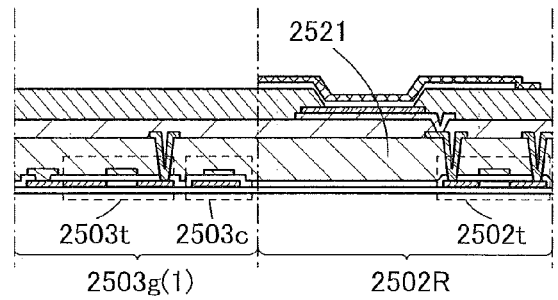

In the display device 2501, transistors with any of a variety of structures can be used. FIG. 18A illustrates an example of using bottom-gate transistors; however, the present invention is not limited to this example, and top-gate transistors may be used in the display device 2501 as illustrated in FIG. 18B.

In addition, there is no particular limitation on the polarity of the transistor 2502*t* and the transistor 2503*t*. For these transistors, n-channel and p-channel transistors may be used, or either n-channel transistors or p-channel transistors may be used, for example. Furthermore, there is no particular limitation on the crystallinity of a semiconductor film used for the transistors 2502*t* and 2503*t*. For example, an amorphous semiconductor film or a crystalline semiconductor film may be used. Examples of semiconductor materials include Group 14 semiconductors (e.g., a semiconductor including silicon), compound semiconductors (including oxide semiconductors), organic semiconductors, and the like. An oxide semiconductor that has an energy gap of 2 eV or more, preferably 2.5 eV or more, further preferably 3 eV or more is preferably used for one of the transistors 2502*t* and 2503*t* or both, so that the off-state current of the transistors can be reduced. Examples of the oxide semiconductors include an In—Ga oxide, an In-M-Zn oxide (M represents Al, Ga, Y, Zr, La, Ce, Sn, Hf, or Nd), and the like.

<Description of Touch Sensor>

Figure 18C:
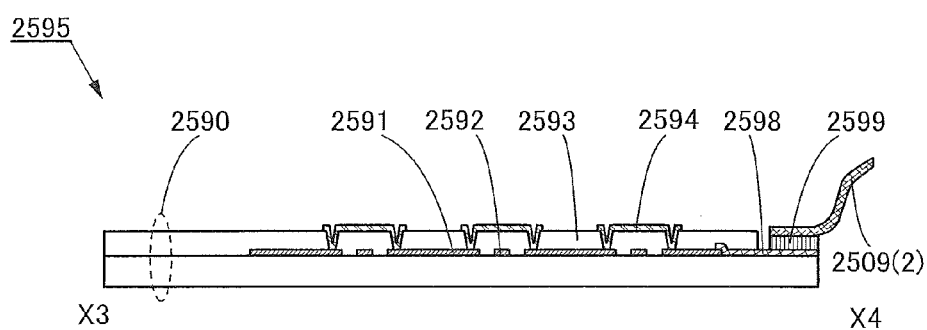

Next, the touch sensor 2595 will be described in detail with reference to FIG. 18C. FIG. 18C corresponds to a cross-sectional view taken along dashed-dotted line X3-X4 in FIG. 17B.

The touch sensor 2595 includes the electrodes 2591 and the electrodes 2592 provided in a staggered arrangement on the substrate 2590, an insulating layer 2593 covering the electrodes 2591 and the electrodes 2592, and the wiring 2594 that electrically connects the adjacent electrodes 2591 to each other.

The electrodes 2591 and the electrodes 2592 are formed using a light-transmitting conductive material. As a light-transmitting conductive material, a conductive oxide such as indium oxide, indium tin oxide, indium zinc oxide, zinc oxide, or zinc oxide to which gallium is added can be used. Note that a film including graphene may be used as well. The film including graphene can be formed, for example, by reducing a film containing graphene oxide. As a reducing method, a method with application of heat or the like can be employed.

The electrodes 2591 and the electrodes 2592 may be formed by, for example, depositing a light-transmitting conductive material on the substrate 2590 by a sputtering method and then removing an unnecessary portion by any of various pattern forming techniques such as photolithography.

Examples of a material for the insulating layer 2593 are a resin such as an acrylic resin or an epoxy resin, a resin having a siloxane bond, and an inorganic insulating material such as silicon oxide, silicon oxynitride, or aluminum oxide.

Openings reaching the electrodes 2591 are formed in the insulating layer 2593, and the wiring 2594 electrically connects the adjacent electrodes 2591. A light-transmitting conductive material can be favorably used as the wiring 2594 because the aperture ratio of the touch panel can be increased. Moreover, a material with higher conductivity than the conductivities of the electrodes 2591 and 2592 can be favorably used for the wiring 2594 because electric resistance can be reduced.

One electrode 2592 extends in one direction, and a plurality of electrodes 2592 are provided in the form of stripes. The wiring 2594 intersects with the electrode 2592.

Adjacent electrodes 2591 are provided with one electrode 2592 provided therebetween. The wiring 2594 electrically connects the adjacent electrodes 2591.

Note that the plurality of electrodes 2591 are not necessarily arranged in the direction orthogonal to one electrode 2592 and may be arranged to intersect with one electrode 2592 at an angle of more than 0 degrees and less than 90 degrees.

The wiring 2598 is electrically connected to any of the electrodes 2591 and 2592. Part of the wiring 2598 functions as a terminal. For the wiring 2598, a metal material such as aluminum, gold, platinum, silver, nickel, titanium, tungsten, chromium, molybdenum, iron, cobalt, copper, or palladium or an alloy material containing any of these metal materials can be used.

Note that an insulating layer that covers the insulating layer 2593 and the wiring 2594 may be provided to protect the touch sensor 2595.

A connection layer 2599 electrically connects the wiring 2598 to the FPC 2509(2).

As the connection layer 2599, any of various anisotropic conductive films (ACF), anisotropic conductive pastes (ACP), or the like can be used.

<Description 2 of Touch Panel>

Figure 19A:
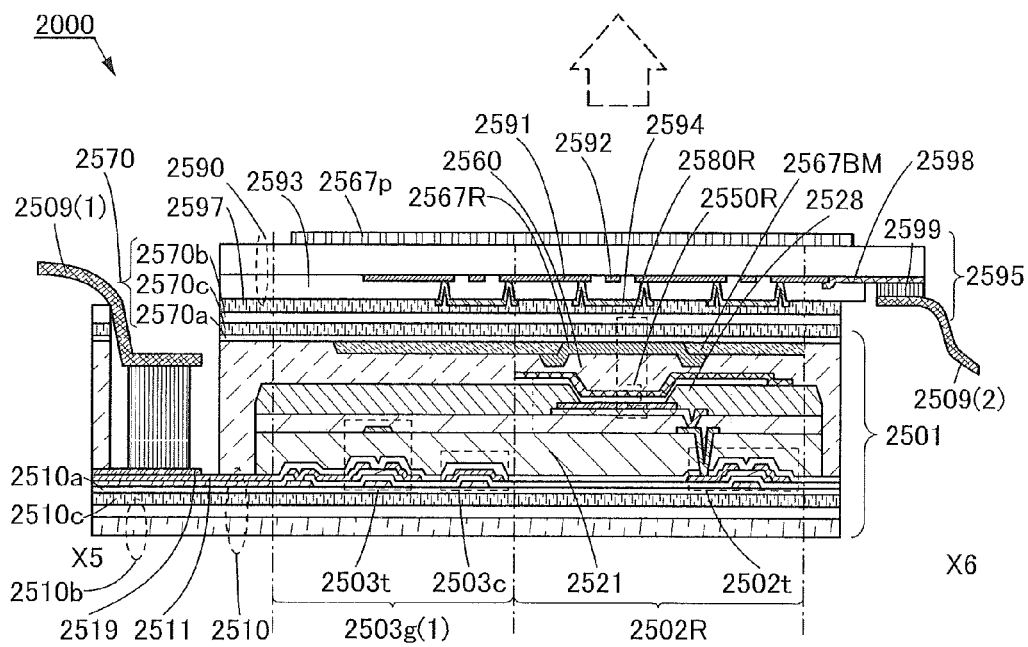
FIGS. 19A and 19B are schematic cross-sectional views each illustrating an example of a touch panel of one embodiment of the present invention.

Next, the touch panel 2000 will be described in detail with reference to FIG. 19A. FIG. 19A corresponds to a cross-sectional view taken along dashed-dotted line X5-X6 in FIG. 17A.

In the touch panel 2000 illustrated in FIG. 19A, the display device 2501 described with reference to FIG. 18A and the touch sensor 2595 described with reference to FIG. 18C are attached to each other.

The touch panel 2000 illustrated in FIG. 19A includes an adhesive layer 2597 and an anti-reflective layer 2567*p* in addition to the components described with reference to FIGS. 18A and 18C.

The adhesive layer 2597 is provided in contact with the wiring 2594. Note that the adhesive layer 2597 attaches the substrate 2590 to the substrate 2570 so that the touch sensor 2595 overlaps with the display device 2501. The adhesive layer 2597 preferably has a light-transmitting property. A heat curable resin or an ultraviolet curable resin can be used for the adhesive layer 2597. For example, an acrylic resin, a urethane-based resin, an epoxy-based resin, or a siloxane-based resin can be used.

The anti-reflective layer 2567*p* is positioned in a region overlapping with pixels. As the anti-reflective layer 2567*p*, a circularly polarizing plate can be used, for example.

Next, a touch panel having a structure different from that illustrated in FIG. 19A will be described with reference to FIG. 19B.

Figure 19B:
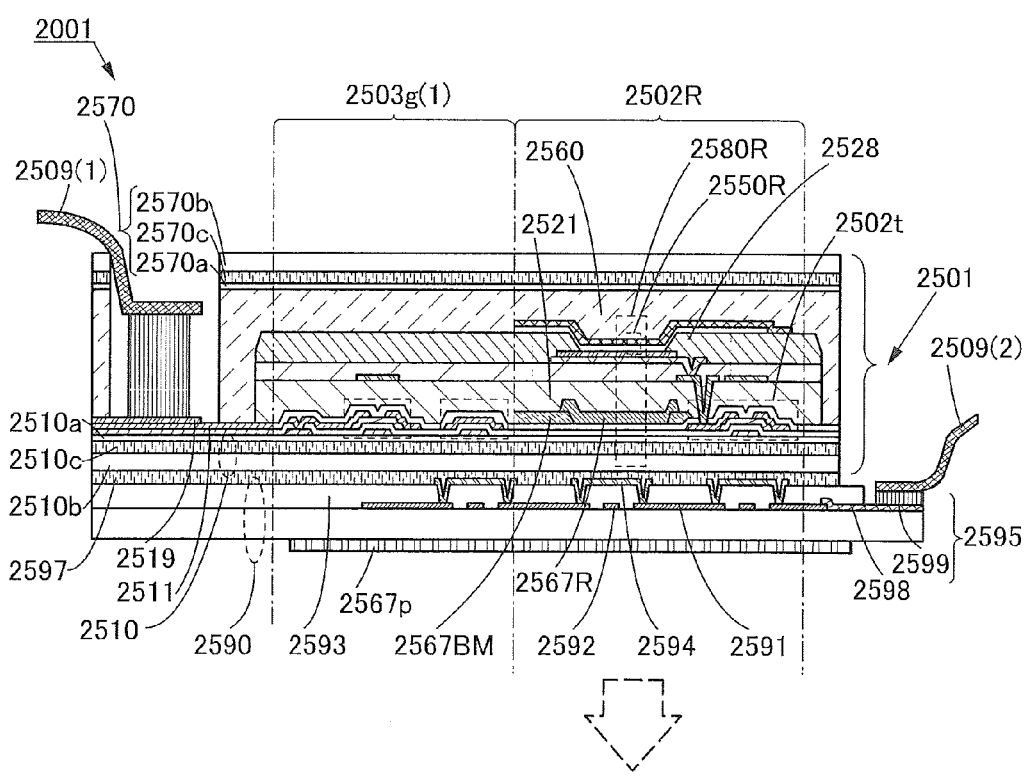

FIG. 19B is a cross-sectional view of a touch panel 2001. The touch panel 2001 illustrated in FIG. 19B differs from the touch panel 2000 illustrated in FIG. 19A in the position of the touch sensor 2595 relative to the display device 2501. Different parts are described in detail below, and the above description of the touch panel 2000 is referred to for the other similar parts.

The coloring layer 2567R is positioned in a region overlapping with the light-emitting element 2550R. The light-emitting element 2550R illustrated in FIG. 19B emits light to the side where the transistor 2502*t* is provided. Accordingly, part of light emitted from the light-emitting element 2550R passes through the coloring layer 2567R and is emitted to the outside of the light-emitting module 2580R as indicated by an arrow in FIG. 19B.

The touch sensor 2595 is provided on the substrate 2510 side of the display device 2501.

The adhesive layer 2597 is provided between the substrate 2510 and the substrate 2590 and attaches the touch sensor 2595 to the display device 2501.

As illustrated in FIG. 19A or 19B, light may be emitted from the light-emitting element to one of upper and lower sides, or both, of the substrate.

<Description of Method for Driving Touch Panel>

Next, an example of a method for driving a touch panel will be described with reference to FIGS. 20A and 20B.

Figure 20A:
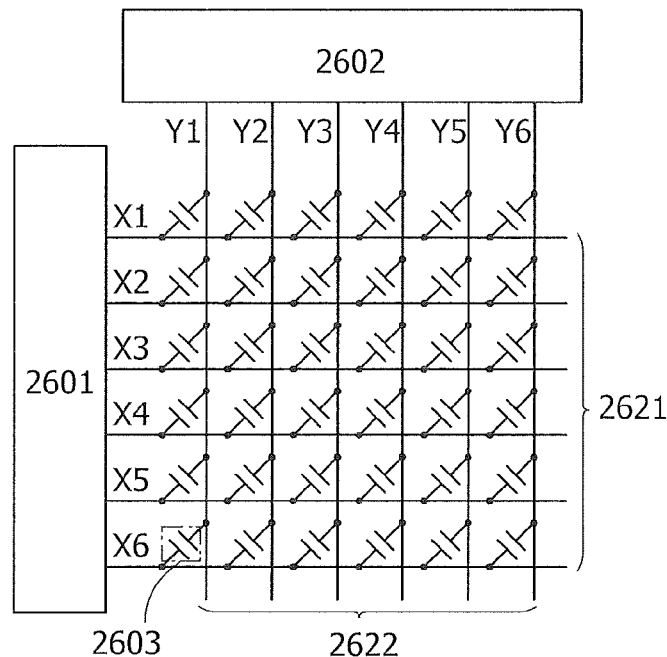
FIGS. 20A and 20B are a block diagram and a timing chart of a touch sensor of one embodiment of the present invention.

FIG. 20A is a block diagram illustrating the structure of a mutual capacitive touch sensor. FIG. 20A illustrates a pulse voltage output circuit 2601 and a current sensing circuit 2602. Note that in FIG. 20A, six wirings X1 to X6 represent the electrodes 2621 to which a pulse voltage is applied, and six wirings Y1 to Y6 represent the electrodes 2622 that detect changes in current. FIG. 20A also illustrates capacitors 2603 that are each formed in a region where the electrodes 2621 and 2622 overlap with each other. Note that functional replacement between the electrodes 2621 and 2622 is possible.

The pulse voltage output circuit 2601 is a circuit for sequentially applying a pulse voltage to the wirings X1 to X6. By application of a pulse voltage to the wirings X1 to X6, an electric field is generated between the electrodes 2621 and 2622 of the capacitor 2603. When the electric field between the electrodes is shielded, for example, a change occurs in the capacitor 2603 (mutual capacitance). The approach or contact of a sensing target can be sensed by utilizing this change.

The current sensing circuit 2602 is a circuit for detecting changes in current flowing through the wirings Y1 to Y6 that are caused by the change in mutual capacitance in the capacitor 2603. No change in current value is detected in the wirings Y1 to Y6 when there is no approach or contact of a sensing target, whereas a decrease in current value is detected when mutual capacitance is decreased owing to the approach or contact of a sensing target. Note that an integrator circuit or the like is used for sensing of current values.

Figure 20B:
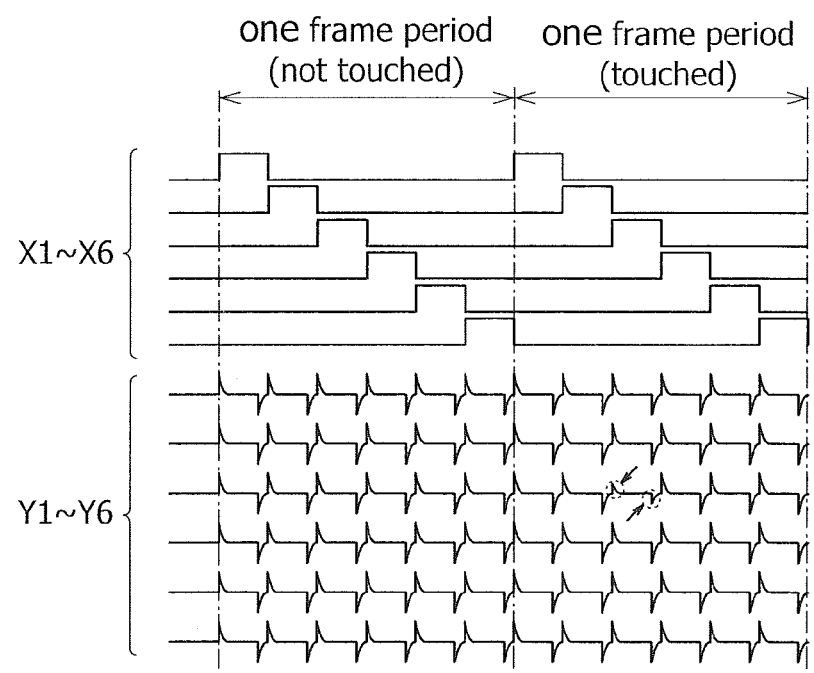

FIG. 20B is a timing chart showing input and output waveforms in the mutual capacitive touch sensor illustrated in FIG. 20A. In FIG. 20B, sensing of a sensing target is performed in all the rows and columns in one frame period. FIG. 20B shows a period when a sensing target is not sensed (not touched) and a period when a sensing target is sensed (touched). Sensed current values of the wirings Y1 to Y6 are shown as the waveforms of voltage values.

A pulse voltage is sequentially applied to the wirings X1 to X6, and the waveforms of the wirings Y1 to Y6 change in accordance with the pulse voltage. When there is no approach or contact of a sensing target, the waveforms of the wirings Y1 to Y6 change in accordance with changes in the voltages of the wirings X1 to X6. The current value is decreased at the point of approach or contact of a sensing target and accordingly the waveform of the voltage value changes.

By detecting a change in mutual capacitance in this manner, the approach or contact of a sensing target can be sensed.

<Description of Sensor Circuit>

Figure 21:
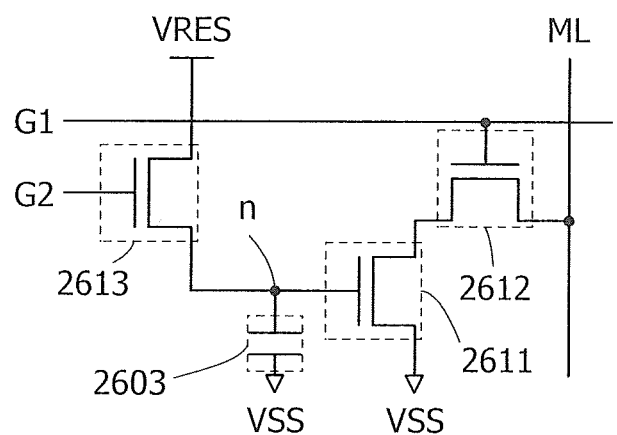
FIG. 21 is a circuit diagram of a touch sensor of one embodiment of the present invention.

Although FIG. 20A illustrates a passive matrix type touch sensor in which only the capacitor 2603 is provided at the intersection of wirings as a touch sensor, an active matrix type touch sensor including a transistor and a capacitor may be used. FIG. 21 illustrates an example of a sensor circuit included in an active matrix type touch sensor.

The sensor circuit in FIG. 21 includes the capacitor 2603 and transistors 2611, 2612, and 2613.

A signal G2 is input to a gate of the transistor 2613. A voltage VRES is applied to one of a source and a drain of the transistor 2613, and one electrode of the capacitor 2603 and a gate of the transistor 2611 are electrically connected to the other of the source and the drain of the transistor 2613. One of a source and a drain of the transistor 2611 is electrically connected to one of a source and a drain of the transistor 2612, and a voltage VSS is applied to the other of the source and the drain of the transistor 2611. A signal G1 is input to a gate of the transistor 2612, and a wiring ML is electrically connected to the other of the source and the drain of the transistor 2612. The voltage VSS is applied to the other electrode of the capacitor 2603.

Next, the operation of the sensor circuit in FIG. 21 will be described. First, a potential for turning on the transistor 2613 is supplied as the signal G2, and a potential with respect to the voltage VRES is thus applied to the node n connected to the gate of the transistor 2611. Then, a potential for turning off the transistor 2613 is applied as the signal G2, whereby the potential of the node n is maintained.

Then, mutual capacitance of the capacitor 2603 changes owing to the approach or contact of a sensing target such as a finger, and accordingly the potential of the node n is changed from VRES.

In reading operation, a potential for turning on the transistor 2612 is supplied as the signal G1. A current flowing through the transistor 2611, that is, a current flowing through the wiring ML is changed in accordance with the potential of the node n. By sensing this current, the approach or contact of a sensing target can be sensed.

In each of the transistors 2611, 2612, and 2613, an oxide semiconductor layer is preferably used as a semiconductor layer in which a channel region is formed. In particular, such a transistor is preferably used as the transistor 2613 so that the potential of the node n can be held for a long time and the frequency of operation of resupplying VRES to the node n (refresh operation) can be reduced.

The structure described in this embodiment can be combined with any of the structures described in the other embodiments as appropriate.

Embodiment 6

In this embodiment, a display module and electronic devices including a light-emitting element of one embodiment of the present invention will be described with reference to FIG. 22 and FIGS. 23A to 23G.

<Description of Display Module>

Figure 22:
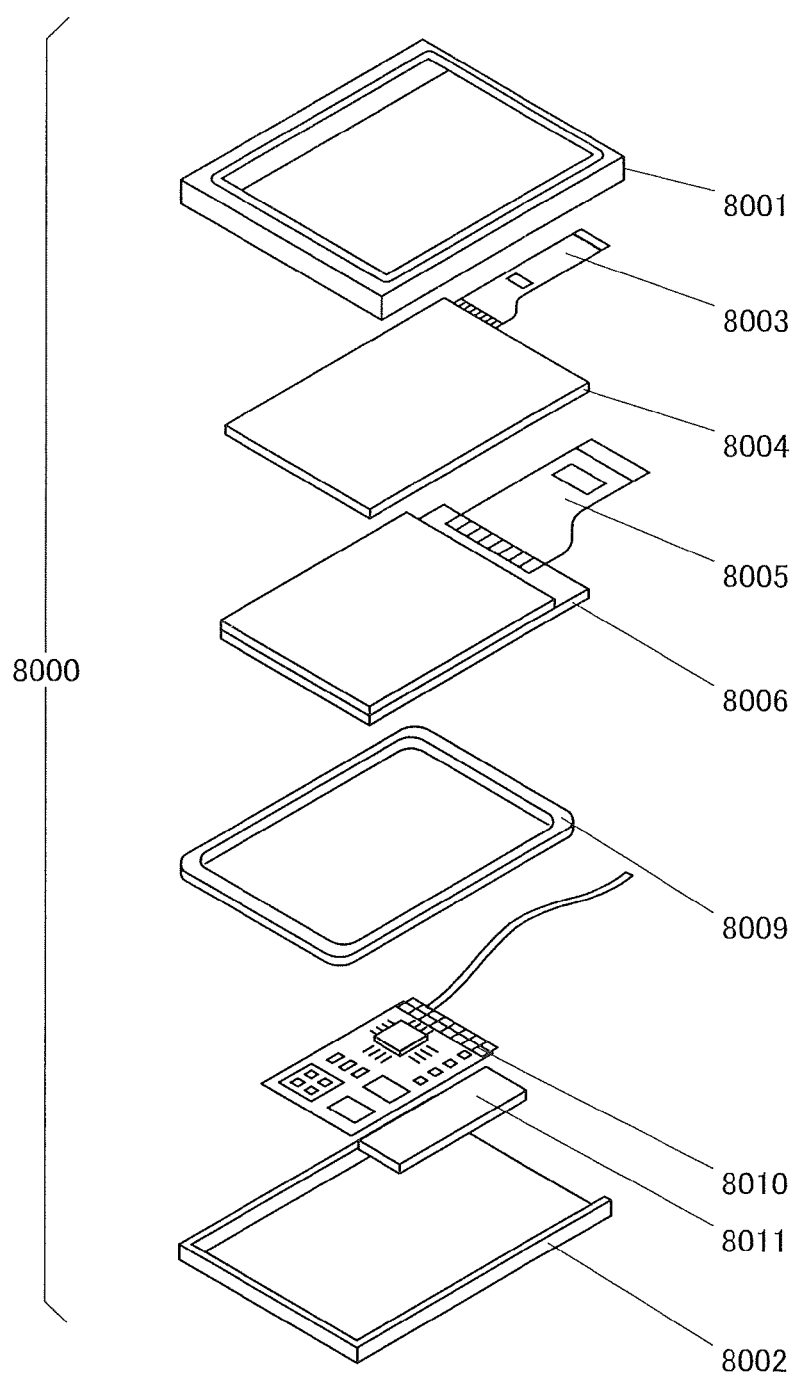
FIG. 22 is a perspective view of a display module of one embodiment of the present invention.

In a display module 8000 in FIG. 22, a touch sensor 8004 connected to an FPC 8003, a display device 8006 connected to an FPC 8005, a frame 8009, a printed board 8010, and a battery 8011 are provided between an upper cover 8001 and a lower cover 8002.

The light-emitting element of one embodiment of the present invention can be used for the display device 8006, for example.

The shapes and sizes of the upper cover 8001 and the lower cover 8002 can be changed as appropriate in accordance with the sizes of the touch sensor 8004 and the display device 8006.

The touch sensor 8004 can be a resistive touch sensor or a capacitive touch sensor and may be formed to overlap with the display device 8006. A counter substrate (sealing substrate) of the display device 8006 can have a touch sensor function. A photosensor may be provided in each pixel of the display device 8006 so that an optical touch sensor is obtained.

The frame 8009 protects the display device 8006 and also serves as an electromagnetic shield for blocking electromagnetic waves generated by the operation of the printed board 8010. The frame 8009 may serve as a radiator plate.

The printed board 8010 has a power supply circuit and a signal processing circuit for outputting a video signal and a clock signal. As a power source for supplying power to the power supply circuit, an external commercial power source or the battery 8011 provided separately may be used. The battery 8011 can be omitted in the case of using a commercial power source.

The display module 8000 can be additionally provided with a member such as a polarizing plate, a retardation plate, or a prism sheet.

<Description of Electronic Device>

FIGS. 23A to 23G illustrate electronic devices. These electronic devices can include a housing 9000, a display portion 9001, a speaker 9003, operation keys 9005 (including a power switch or an operation switch), a connection terminal 9006, a sensor 9007 (a sensor having a function of measuring or sensing force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared ray), a microphone 9008, and the like.

The electronic devices illustrated in FIGS. 23A to 23G can have a variety of functions, for example, a function of displaying a variety of data (a still image, a moving image, a text image, and the like) on the display portion, a touch sensor function, a function of displaying a calendar, date, time, and the like, a function of controlling a process with a variety of software (programs), a wireless communication function, a function of being connected to a variety of computer networks with a wireless communication function, a function of transmitting and receiving a variety of data with a wireless communication function, a function of reading a program or data stored in a memory medium and displaying the program or data on the display portion, and the like. Note that functions that can be provided for the electronic devices illustrated in FIGS. 23A to 23G are not limited to those described above, and the electronic devices can have a variety of functions. Although not illustrated in FIGS. 23A to 23G, the electronic devices may include a plurality of display portions. The electronic devices may have a camera or the like and a function of taking a still image, a function of taking a moving image, a function of storing the taken image in a memory medium (an external memory medium or a memory medium incorporated in the camera), a function of displaying the taken image on the display portion, or the like.

The electronic devices illustrated in FIGS. 23A to 23G will be described in detail below.

Figure 23A:
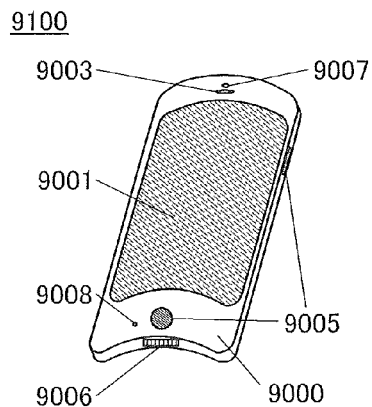
FIGS. 23A to 23G illustrate electronic devices of embodiments of the present invention.

FIG. 23A is a perspective view of a portable information terminal 9100. The display portion 9001 of the portable information terminal 9100 is flexible. Therefore, the display portion 9001 can be incorporated along a bent surface of a bent housing 9000. In addition, the display portion 9001 includes a touch sensor, and operation can be performed by touching the screen with a finger, a stylus, or the like. For example, when an icon displayed on the display portion 9001 is touched, an application can be started.

Figure 23D:
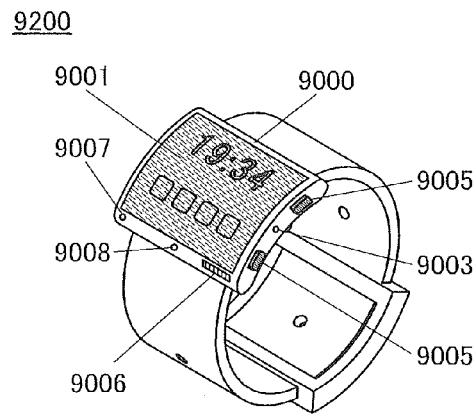
Figure 23B:
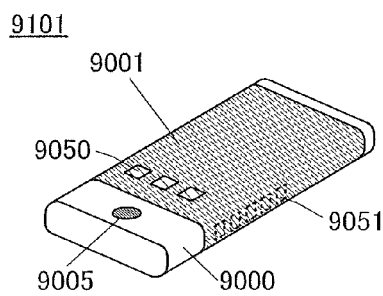

FIG. 23B is a perspective view of a portable information terminal 9101. The portable information terminal 9101 functions as, for example, one or more of a telephone set, a notebook, and an information browsing system. Specifically, the portable information terminal can be used as a smartphone. Note that the speaker 9003, the connection terminal 9006, the sensor 9007, and the like, which are not shown in FIG. 23B, can be positioned in the portable information terminal 9101 as in the portable information terminal 9100 shown in FIG. 23A. The portable information terminal 9101 can display characters and image information on its plurality of surfaces. For example, three operation buttons 9050 (also referred to as operation icons, or simply, icons) can be displayed on one surface of the display portion 9001. Furthermore, information 9051 indicated by dashed rectangles can be displayed on another surface of the display portion 9001. Examples of the information 9051 include display indicating reception of an incoming email, social networking service (SNS) message, call, and the like; the title and sender of an email and SNS message; the date; the time; remaining battery; and the reception strength of an antenna. Instead of the information 9051, the operation buttons 9050 or the like may be displayed on the position where the information 9051 is displayed.

Figure 23E:
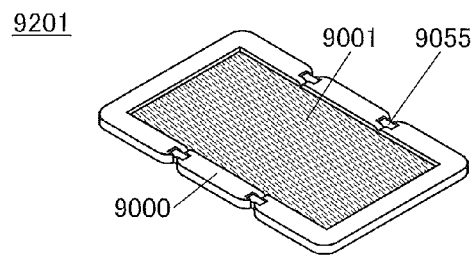
Figure 23C:
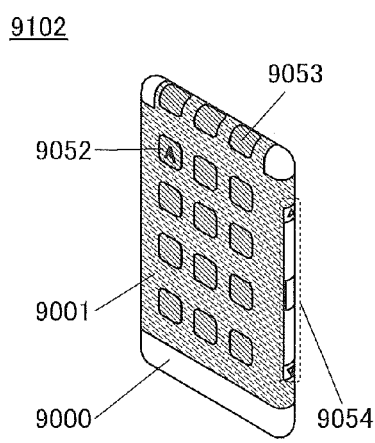

FIG. 23C is a perspective view of a portable information terminal 9102. The portable information terminal 9102 has a function of displaying information on three or more surfaces of the display portion 9001. Here, information 9052, information 9053, and information 9054 are displayed on different surfaces. For example, a user of the portable information terminal 9102 can see the display (here, the information 9053) with the portable information terminal 9102 put in a breast pocket of his/her clothes. Specifically, a caller's phone number, name, or the like of an incoming call is displayed in a position that can be seen from above the portable information terminal 9102. Thus, the user can see the display without taking out the portable information terminal 9102 from the pocket and decide whether to answer the call.

FIG. 23D is a perspective view of a watch-type portable information terminal 9200. The portable information terminal 9200 is capable of executing a variety of applications such as mobile phone calls, e-mailing, viewing and editing texts, music reproduction, Internet communication, and computer games. The display surface of the display portion 9001 is bent, and images can be displayed on the bent display surface. The portable information terminal 9200 can employ near field communication that is a communication method based on an existing communication standard. In that case, for example, mutual communication between the portable information terminal 9200 and a headset capable of wireless communication can be performed, and thus handsfree calling is possible. The portable information terminal 9200 includes the connection terminal 9006, and data can be directly transmitted to and received from another information terminal via a connector. Power charging through the connection terminal 9006 is possible. Note that the charging operation may be performed by wireless power feeding without using the connection terminal 9006.

Figure 23F:
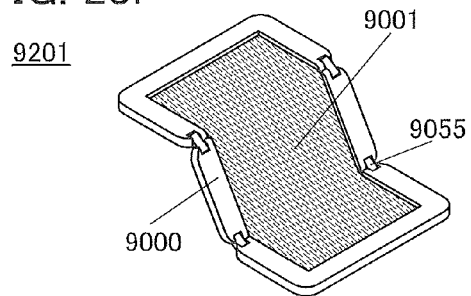
Figure 23G:
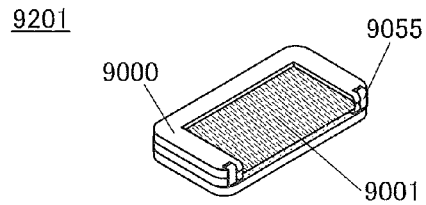

FIGS. 23E, 23F, and 23G are perspective views of a foldable portable information terminal 9201. FIG. 23E is a perspective view illustrating the portable information terminal 9201 that is opened. FIG. 23F is a perspective view illustrating the portable information terminal 9201 that is being opened or being folded. FIG. 23G is a perspective view illustrating the portable information terminal 9201 that is folded. The portable information terminal 9201 is highly portable when folded. When the portable information terminal 9201 is opened, a seamless large display region is highly browsable. The display portion 9001 of the portable information terminal 9201 is supported by three housings 9000 joined together by hinges 9055. By folding the portable information terminal 9201 at a connection portion between two housings 9000 with the hinges 9055, the portable information terminal 9201 can be reversibly changed in shape from an opened state to a folded state. For example, the portable information terminal 9201 can be bent with a radius of curvature of greater than or equal to 1 mm and less than or equal to 150 mm.

The electronic devices described in this embodiment each include the display portion for displaying some sort of data. Note that the light-emitting element of one embodiment of the present invention can also be used for an electronic device which does not have a display portion. The structure in which the display portion of the electronic device described in this embodiment is flexible and display can be performed on the bent display surface or the structure in which the display portion of the electronic device is foldable is described as an example; however, the structure is not limited thereto and a structure in which the display portion of the electronic device is not flexible and display is performed on a plane portion may be employed.

The structure described in this embodiment can be combined with any of the structures described in the other embodiments as appropriate.

Embodiment 7

In this embodiment, a light-emitting device including the light-emitting element of one embodiment of the present invention will be described with reference to FIGS. 24A to 24C and FIGS. 25A to 25D.

Figure 24A:
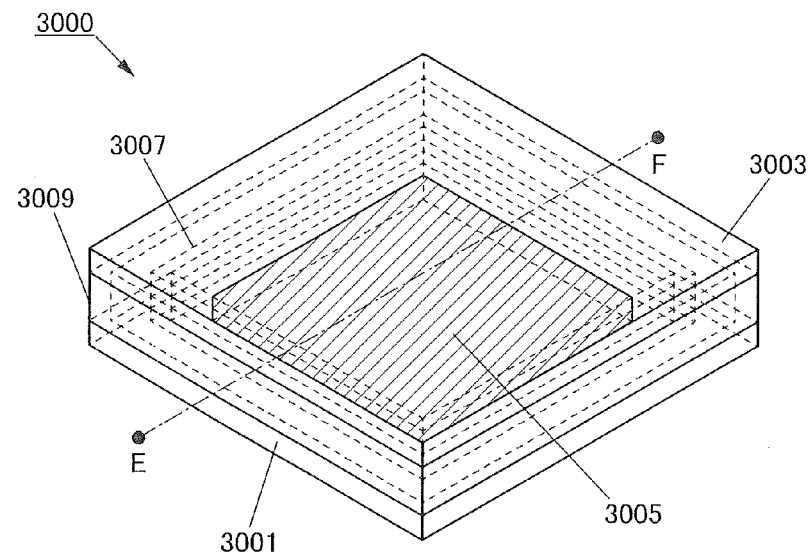
FIGS. 24A to 24C are a perspective view and cross-sectional views illustrating a light-emitting device of one embodiment of the present invention.
Figure 24B:
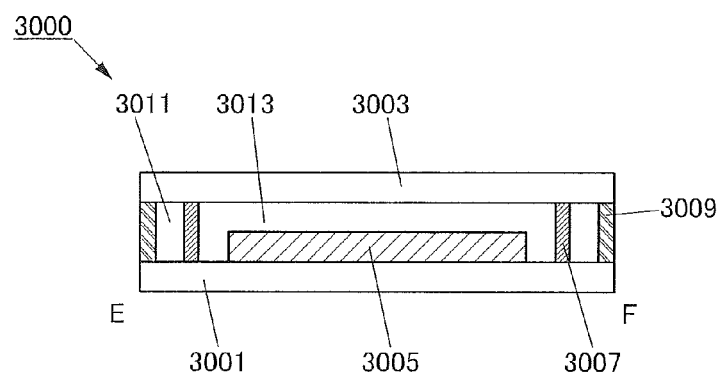

FIG. 24A is a perspective view of a light-emitting device 3000 shown in this embodiment, and FIG. 24B is a cross-sectional view along dashed-dotted line E-F in FIG. 24A. Note that in FIG. 24A, some components are illustrated by broken lines in order to avoid complexity of the drawing.

The light-emitting device 3000 illustrated in FIGS. 24A and 24B includes a substrate 3001, a light-emitting element 3005 over the substrate 3001, a first sealing region 3007 provided around the light-emitting element 3005, and a second sealing region 3009 provided around the first sealing region 3007.

Light is emitted from the light-emitting element 3005 through one or both of the substrate 3001 and a substrate 3003. In FIGS. 24A and 24B, a structure in which light is emitted from the light-emitting element 3005 to the lower side (the substrate 3001 side) is illustrated.

As illustrated in FIGS. 24A and 24B, the light-emitting device 3000 has a double sealing structure in which the light-emitting element 3005 is surrounded by the first sealing region 3007 and the second sealing region 3009. With the double sealing structure, entry of impurities (e.g., water, oxygen, and the like) from the outside into the light-emitting element 3005 can be favorably suppressed. Note that it is not necessary to provide both the first sealing region 3007 and the second sealing region 3009. For example, only the first sealing region 3007 may be provided.

Note that in FIG. 24B, the first sealing region 3007 and the second sealing region 3009 are each provided in contact with the substrate 3001 and the substrate 3003. However, without limitation to such a structure, for example, one or both of the first sealing region 3007 and the second sealing region 3009 may be provided in contact with an insulating film or a conductive film provided on the substrate 3001. Alternatively, one or both of the first sealing region 3007 and the second sealing region 3009 may be provided in contact with an insulating film or a conductive film provided on the substrate 3003.

The substrate 3001 and the substrate 3003 can have structures similar to those of the substrate 200 and the substrate 220 described in Embodiment 1, respectively. The light-emitting element 3005 can have a structure similar to that of any of the light-emitting elements described in the above embodiments.

For the first sealing region 3007, a material containing glass (e.g., a glass frit, a glass ribbon, and the like) can be used. For the second sealing region 3009, a material containing a resin can be used. With the use of the material containing glass for the first sealing region 3007, productivity and a sealing property can be improved. Moreover, with the use of the material containing a resin for the second sealing region 3009, impact resistance and heat resistance can be improved. However, the materials used for the first sealing region 3007 and the second sealing region 3009 are not limited to such, and the first sealing region 3007 may be formed using the material containing a resin and the second sealing region 3009 may be formed using the material containing glass.

The glass frit may contain, for example, magnesium oxide, calcium oxide, strontium oxide, barium oxide, cesium oxide, sodium oxide, potassium oxide, boron oxide, vanadium oxide, zinc oxide, tellurium oxide, aluminum oxide, silicon dioxide, lead oxide, tin oxide, phosphorus oxide, ruthenium oxide, rhodium oxide, iron oxide, copper oxide, manganese dioxide, molybdenum oxide, niobium oxide, titanium oxide, tungsten oxide, bismuth oxide, zirconium oxide, lithium oxide, antimony oxide, lead borate glass, tin phosphate glass, vanadate glass, or borosilicate glass. The glass frit preferably contains at least one kind of transition metal to absorb infrared light.

As the above glass frits, for example, a frit paste is applied to a substrate and is subjected to heat treatment, laser light irradiation, or the like. The frit paste contains the glass frit and a resin (also referred to as a binder) diluted by an organic solvent. Note that an absorber which absorbs light having the wavelength of laser light may be added to the glass fit. For example, an Nd:YAG laser or a semiconductor laser is preferably used as the laser. The shape of laser light may be circular or quadrangular.

As the above material containing a resin, for example, materials that include polyester, polyolefin, polyamide (e.g., nylon, aramid), polyimide, polycarbonate, an acrylic resin, urethane, an epoxy resin, or a resin having a siloxane bond can be used.

Note that in the case where the material containing glass is used for one or both of the first sealing region 3007 and the second sealing region 3009, the material containing glass preferably has a thermal expansion coefficient close to that of the substrate 3001. With the above structure, generation of a crack in the material containing glass or the substrate 3001 due to thermal stress can be suppressed.

For example, the following advantageous effect can be obtained in the case where the material containing glass is used for the first sealing region 3007 and the material containing a resin is used for the second sealing region 3009.

The second sealing region 3009 is provided closer to an outer portion of the light-emitting device 3000 than the first sealing region 3007 is. In the light-emitting device 3000, distortion due to external force or the like increases toward the outer portion. Thus, the outer portion of the light-emitting device 3000 where a larger amount of distortion is generated, that is, the second sealing region 3009 is sealed using the material containing a resin and the first sealing region 3007 provided on an inner side of the second sealing region 3009 is sealed using the material containing glass, whereby the light-emitting device 3000 is less likely to be damaged even when distortion due to external force or the like is generated.

Furthermore, as illustrated in FIG. 24B, a first region 3011 corresponds to the region surrounded by the substrate 3001, the substrate 3003, the first sealing region 3007, and the second sealing region 3009. A second region 3013 corresponds to the region surrounded by the substrate 3001, the substrate 3003, the light-emitting element 3005, and the first sealing region 3007.

The first region 3011 and the second region 3013 are preferably filled with, for example, an inert gas such as a rare gas or a nitrogen gas. Note that for the first region 3011 and the second region 3013, a reduced pressure state is preferred to an atmospheric pressure state.

Figure 24C:
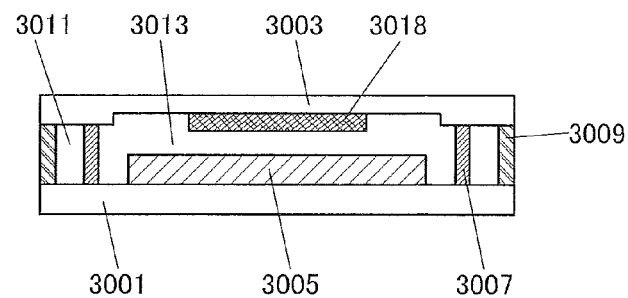

FIG. 24C illustrates a modification example of the structure in FIG. 24B. FIG. 24C is a cross-sectional view illustrating the modification example of the light-emitting device 3000.

FIG. 24C illustrates a structure in which a desiccant 3018 is provided in a recessed portion provided in part of the substrate 3003. The other components are the same as those of the structure illustrated in FIG. 24B.

As the desiccant 3018, a substance which adsorbs moisture and the like by chemical adsorption or a substance which adsorbs moisture and the like by physical adsorption can be used. Examples of the substance that can be used as the desiccant 3018 include alkali metal oxides, alkaline earth metal oxide (e.g., calcium oxide, barium oxide, and the like), sulfate, metal halides, perchlorate, zeolite, silica gel, and the like.

Next, modification examples of the light-emitting device 3000 which is illustrated in FIG. 24B are described with reference to FIGS. 25A to 25D. Note that FIGS. 25A to 25D are cross-sectional views illustrating the modification examples of the light-emitting device 3000 illustrated in FIG. 24B.

In each of the light-emitting devices illustrated in FIGS. 25A to 25D, the second sealing region 3009 is not provided but only the first sealing region 3007 is provided. Moreover, in each of the light-emitting devices illustrated in FIGS. 25A to 25D, a region 3014 is provided instead of the second region 3013 illustrated in FIG. 24B.

For the region 3014, for example, materials that include polyester, polyolefin, polyamide (e.g., nylon or aramid), polyimide, polycarbonate, an acrylic resin, an epoxy resin, urethane, an epoxy resin, or a resin having a siloxane bond can be used.

When the above-described material is used for the region 3014, what is called a solid-sealing light-emitting device can be obtained.

Figure 25A:
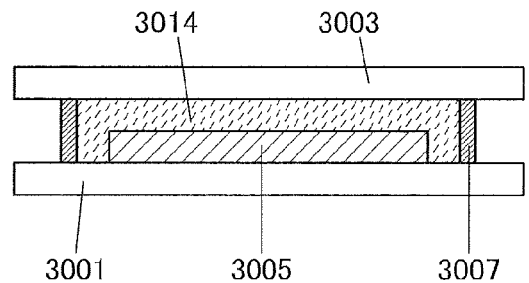
FIGS. 25A to 25D are cross-sectional views each illustrating a light-emitting device of one embodiment of the present invention.
Figure 25B:
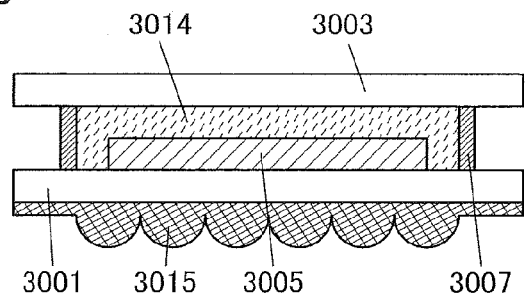

In the light-emitting device illustrated in FIG. 25B, a substrate 3015 is provided on the substrate 3001 side of the light-emitting device illustrated in FIG. 25A.

The substrate 3015 has unevenness as illustrated in FIG. 25B. With a structure in which the substrate 3015 having unevenness is provided on the side through which light emitted from the light-emitting element 3005 is extracted, the efficiency of extraction of light from the light-emitting element 3005 can be improved. Note that instead of the structure having unevenness and illustrated in FIG. 25B, a substrate having a function as a diffusion plate may be provided.

Figure 25C:
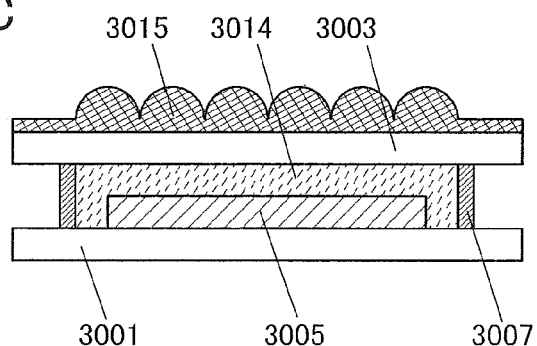

In the light-emitting device illustrated in FIG. 25C, light is extracted through the substrate 3003 side, unlike in the light-emitting device illustrated in FIG. 25A, in which light is extracted through the substrate 3001 side.

The light-emitting device illustrated in FIG. 25C includes the substrate 3015 on the substrate 3003 side. The other components are the same as those of the light-emitting device illustrated in FIG. 25B.

Figure 25D:
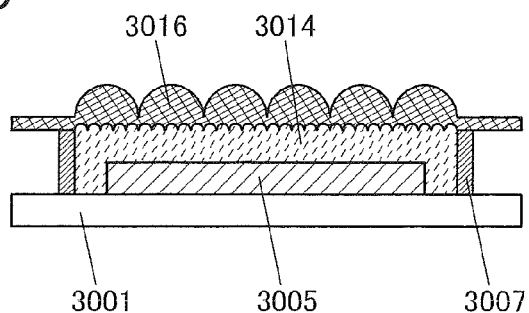

In the light-emitting device illustrated in FIG. 25D, the substrate 3003 and the substrate 3015 included in the light-emitting device illustrated in FIG. 25C are not provided but a substrate 3016 is provided.

The substrate 3016 includes first unevenness positioned closer to the light-emitting element 3005 and second unevenness positioned farther from the light-emitting element 3005. With the structure illustrated in FIG. 25D, the efficiency of extraction of light from the light-emitting element 3005 can be further improved.

Thus, the use of the structure described in this embodiment can provide a light-emitting device in which deterioration of a light-emitting element due to impurities such as moisture and oxygen is suppressed. Alternatively, with the structure described in this embodiment, a light-emitting device having high light extraction efficiency can be obtained.

Note that the structure described in this embodiment can be combined as appropriate with any of the structures described in the other embodiments and the examples.

Embodiment 8

In this embodiment, examples in which the light-emitting element of one embodiment of the present invention is applied to various lighting devices and electronic devices will be described with reference to FIGS. 26A to 26C and FIG. 27.

An electronic device or a lighting device that has a light-emitting region with a curved surface can be obtained with the use of the light-emitting element of one embodiment of the present invention which is manufactured over a substrate having flexibility.

Furthermore, a light-emitting device to which one embodiment of the present invention is applied can also be applied to lighting for motor vehicles, examples of which are lighting for a dashboard, a windshield, a ceiling, and the like.

Figure 26A:
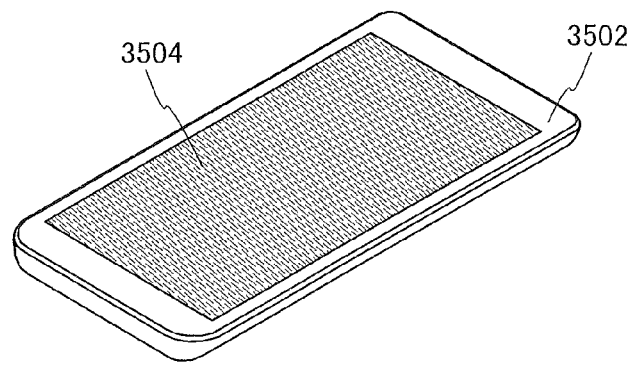
FIGS. 26A and 26B illustrate a lighting device of one embodiment of the present invention and FIG. 26C illustrates an electronic device of one embodiment of the present invention.
Figure 26B:
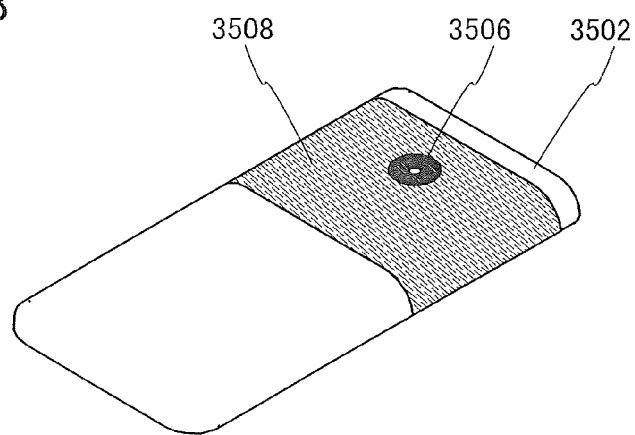

FIG. 26A is a perspective view illustrating one surface of a multifunction terminal 3500, and FIG. 26B is a perspective view illustrating the other surface of the multifunction terminal 3500. In a housing 3502 of the multifunction terminal 3500, a display portion 3504, a camera 3506, lighting 3508, and the like are incorporated. The light-emitting device of one embodiment of the present invention can be used for the lighting 3508.

The lighting 3508 that includes the light-emitting device of one embodiment of the present invention functions as a planar light source. Thus, unlike a point light source typified by an LED, the lighting 3508 can provide light emission with low directivity. When the lighting 3508 and the camera 3506 are used in combination, for example, imaging can be performed by the camera 3506 with the lighting 3508 lighting or flashing. Because the lighting 3508 functions as a planar light source, a photograph as if taken under natural light can be taken.

Note that the multifunction terminal 3500 illustrated in FIGS. 26A and 26B can have a variety of functions as in the electronic devices illustrated in FIGS. 23A to 23G.

The housing 3502 can include a speaker, a sensor (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), a microphone, and the like. When a detection device including a sensor for detecting inclination, such as a gyroscope or an acceleration sensor, is provided inside the multifunction terminal 3500, display on the screen of the display portion 3504 can be automatically switched by determining the orientation of the multifunction terminal 3500 (whether the multifunction terminal is placed horizontally or vertically for a landscape mode or a portrait mode).

The display portion 3504 may function as an image sensor. For example, an image of a palm print, a fingerprint, or the like is taken when the display portion 3504 is touched with the palm or the finger, whereby personal authentication can be performed. Furthermore, by providing a backlight or a sensing light source which emits near-infrared light in the display portion 3504, an image of a finger vein, a palm vein, or the like can be taken. Note that the light-emitting device of one embodiment of the present invention may be used for the display portion 3504.

Figure 26C:
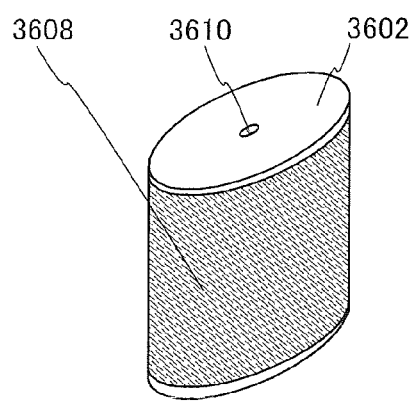

FIG. 26C is a perspective view of a security light 3600. The security light 3600 includes lighting 3608 on the outside of the housing 3602, and a speaker 3610 and the like are incorporated in the housing 3602. The light-emitting device of one embodiment of the present invention can be used for the lighting 3608.

The security light 3600 emits light when the lighting 3608 is gripped or held, for example. An electronic circuit that can control the manner of light emission from the security light 3600 may be provided in the housing 3602. The electronic circuit may be a circuit that enables light emission once or intermittently plural times or may be a circuit that can adjust the amount of emitted light by controlling the current value for light emission. A circuit with which a loud audible alarm is output from the speaker 3610 at the same time as light emission from the lighting 3608 may be incorporated.

The security light 3600 can emit light in various directions; therefore, it is possible to intimidate a thug or the like with light, or light and sound. Moreover, the security light 3600 may include a camera such as a digital still camera to have a photography function.

FIG. 27 illustrates an example in which the light-emitting element is used for an indoor lighting device 8501. Since the light-emitting element can have a larger area, a lighting device having a large area can also be formed. In addition, a lighting device 8502 in which a light-emitting region has a curved surface can also be formed with the use of a housing with a curved surface. A light-emitting element described in this embodiment is in the form of a thin film, which allows the housing to be designed more freely. Therefore, the lighting device can be elaborately designed in a variety of ways. Furthermore, a wall of the room may be provided with a large-sized lighting device 8503. Touch sensors may be provided in the lighting devices 8501, 8502, and 8503 to control the power on/off of the lighting devices.

Moreover, when the light-emitting element is used on the surface side of a table, a lighting device 8504 which has a function as a table can be obtained. When the light-emitting element is used as part of other furniture, a lighting device which has a function as the furniture can be obtained.

As described above, lighting devices and electronic devices can be obtained by application of the light-emitting device of one embodiment of the present invention. Note that the light-emitting device can be used for electronic devices in a variety of fields without being limited to the lighting devices and the electronic devices described in this embodiment.

Note that the structure described in this embodiment can be combined as appropriate with any of the structures described in the other embodiments and the examples.

Example 1

Figure 43:
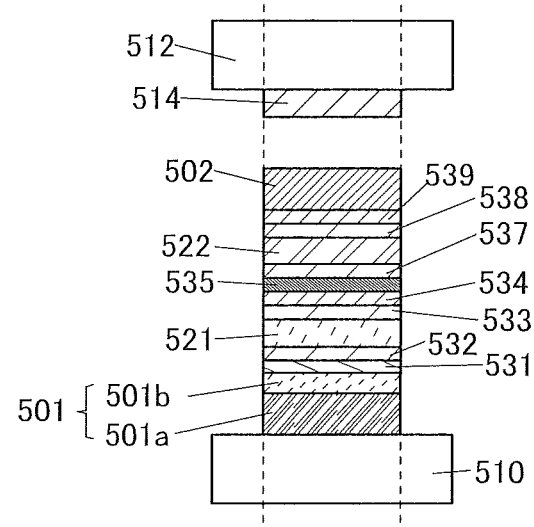
FIG. 43 is a schematic cross-sectional view illustrating a light-emitting element in Example.

In Example 1, an example of fabricating light-emitting elements of one embodiment of the present invention (Light-emitting elements 5 and 7) will be described. A schematic cross-sectional view of the light-emitting elements fabricated in Example 1 is shown in FIG. 43, the detailed structures of the light-emitting elements are shown in Tables 8 and 9, and structures and abbreviations of the compounds used here are given below.

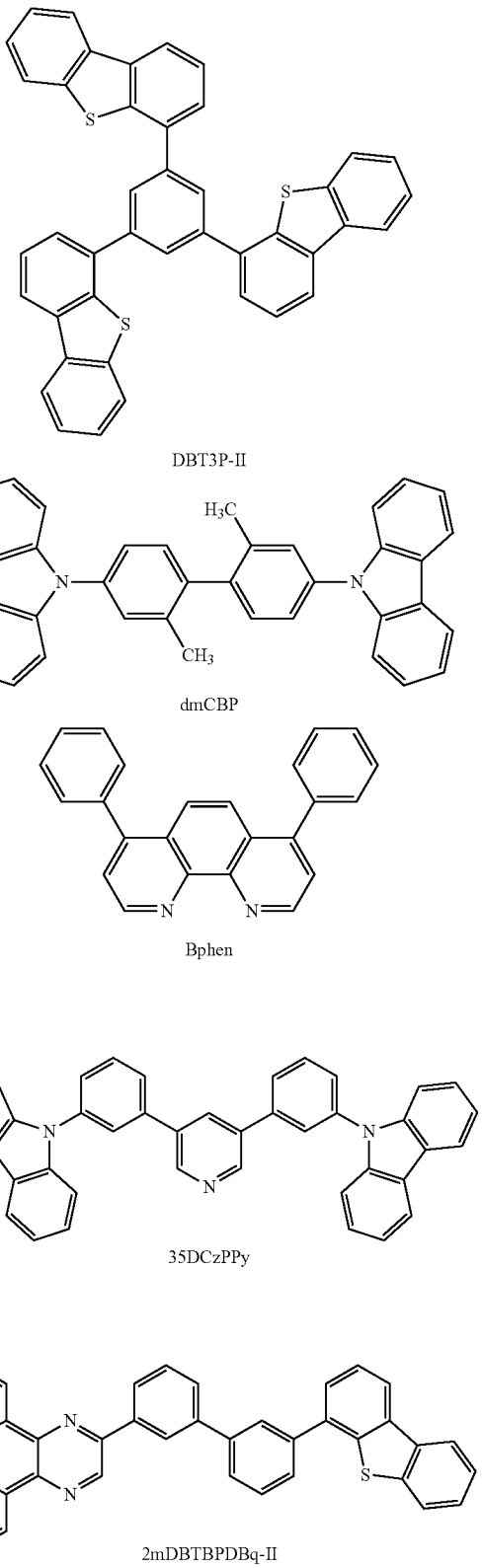

DBT3P-II dmCBP

Bphen

35DCzPPy

2mDBTBPDBq-II

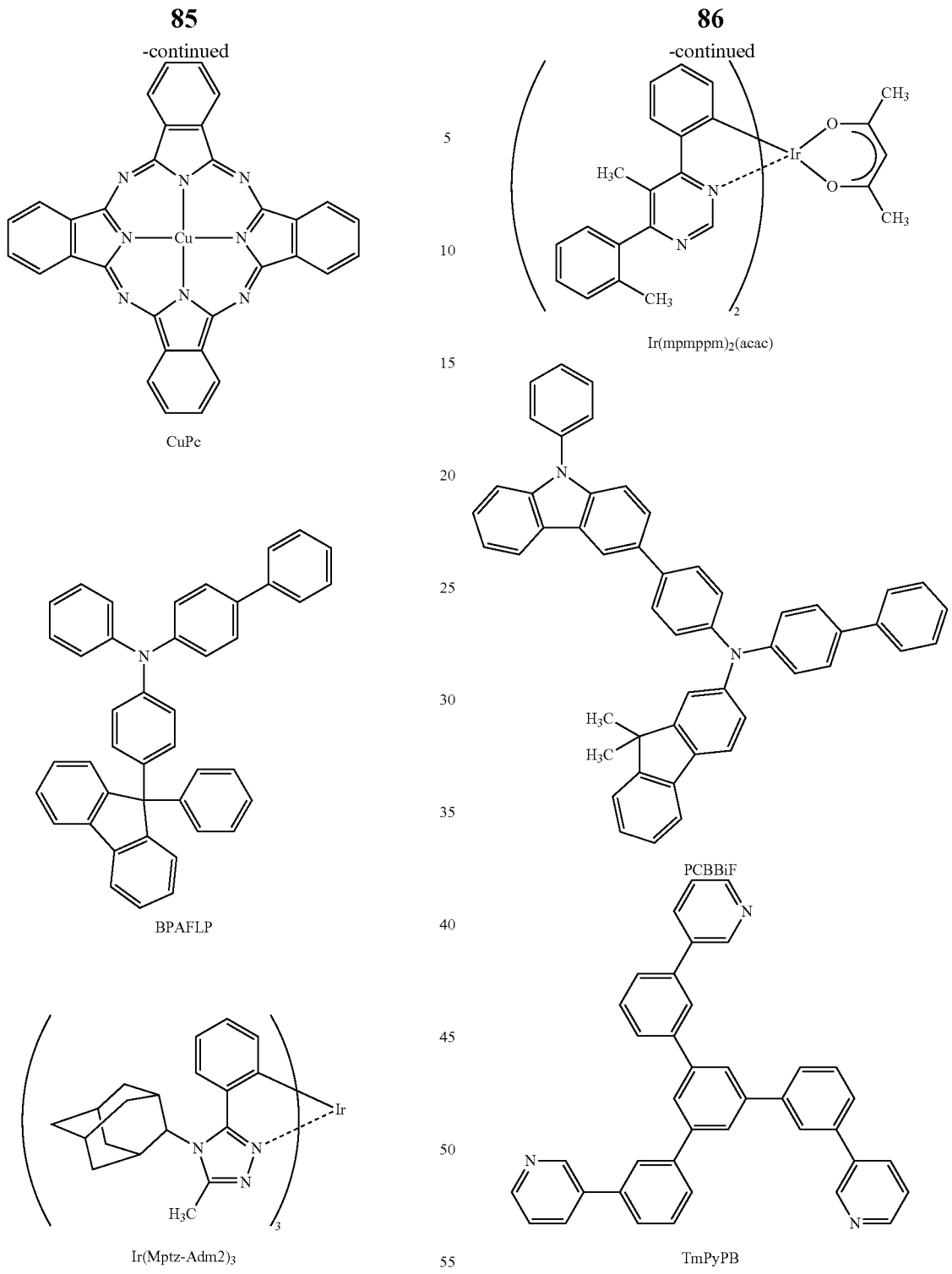
CuPc
BPAFLP
Ir(Mptz-Adm2)₃
Ir(mpmppm)₂(acac)
PCBBiF
TmPyPB
TABLE 8
| | Layer | Reference numeral | Thickness (nm) | Material | Weight ratio *1) |
|---|---|---|---|---|---|
| Light-emitting element 5 | Optical element | 514 | — | CF(Blue) | — |
| | Electrode | 502(2) | 70 | ITO | — |
| | | 502(1) | 15 | Ag:Mg | 1:0.1 |
| | Electron-injection layer | 539 | 1 | LiF | — |

TABLE 8-continued

|  | Layer | Reference numeral | Thickness (nm) | Material | Weight ratio *1) |
|---|---|---|---|---|---|
|  | Electron-transport layer | 538(2) | 20 | Bphen | — |
|  |  | 538(1) | 15 | 2mDBTBPDBq-II | — |
|  | Light-emitting layer | 522 | 40 | 2mDBTBPDBq-II:PCBBiF:Ir(mpmppm)$_2$(acac) | 0.8:0.2:0.05 |
|  | Hole-transport layer | 537 | 15 | BPAFLP | — |
|  | Charge-generation layer | 535 | 17.5 | DBT3P-II:MoO$_3$ | 1:0.5 |
|  | Electron-injection layer | 534(2) | 2 | CuPc | — |
|  |  | 534(1) | 0.1 | Li$_2$O | — |
|  | Electron-transport layer | 533(2) | 10 | Bphen | — |
|  |  | 533(1) | 10 | 35DCzPPy | — |
|  | Light-emitting layer | 521 | 30 | 35DCzPPy:Ir(Mptz-Adm2)$_3$ | 1:0.06 |
|  | Hole-transport layer | 532 | 15 | dmCBP | — |
|  | Hole-injection layer | 531 | 15 | DBT3P-II:MoO$_3$ | 1:0.5 |
|  | Electrode | 501b | 10 | ITSO | — |
|  |  | 501a | 100 | Ag—Pd—Cu | — |
| Light-emitting element 6 | Optical element | 514 | — | CF(Blue) | — |
|  | Electrode | 502(2) | 70 | ITO | — |
|  |  | 502(1) | 15 | Ag:Mg | 1:0.1 |
|  | Electron-injection layer | 539 | 1 | LiF | — |
|  | Electron-transport layer | 538(2) | 20 | Bphen | — |
|  |  | 538(1) | 15 | 2mDBTBPDBq-II | — |
|  | Light-emitting layer | 522 | 40 | 2mDBTBPDBq-II:PCBBiF:Ir(mpmppm)$_2$(acac) | 0.8:0.2:0.06 |
|  | Hole-transport layer | 537 | 15 | BPAFLP | — |
|  | Charge-generation layer | 535 | 17.5 | DBT3P-II:MoO$_3$ | 1:0.5 |
|  | Electron-injection layer | 534(2) | 2 | CuPc | — |
|  |  | 534(1) | 0.1 | Li$_2$O | — |
|  | Electron-transport layer | 533(2) | 10 | Bphen | — |
|  |  | 533(1) | 10 | 35DCzPPy | — |
|  | Light-emitting layer | 521 | 30 | 35DCzPPy:Ir(Mptz-Adm2)$_3$ | 1:0.06 |
|  | Hole-transport layer | 532 | 15 | dmCBP | — |
|  | Hole-injection layer | 531 | 47.5 | DBT3P-II:MoO$_3$ | 1:0.5 |
|  | Electrode | 501b | 85 | ITSO | — |
|  |  | 501a | 100 | Ag—Pd—Cu | — |

*1) The ratio of Ag:Mg is represented in volume ratio.

TABLE 9

|  | Layer | Reference numeral | Thickness (nm) | Material | Weight ratio *1) |
|---|---|---|---|---|---|
| Light-emitting element 7 | Optical element | 514 | — | CF(Blue) | — |
|  | Electrode | 502(2) | 70 | ITO | — |
|  |  | 502(1) | 15 | Ag:Mg | 1:0.1 |
|  | Electron-injection layer | 539 | 1 | LiF | — |
|  | Electron-transport layer | 538 | 10 | TmPyPb | — |
|  | Light-emitting layer | 522 | 30 | 35DCzPPy:Ir(Mptz-Adm2)$_3$ | 1:0.05 |
|  | Hole-transport layer | 537 | 10 | dmCBP | — |
|  | Charge-generation layer | 535 | 7.5 | DBT3P-II:MoO$_3$ | 1:0.5 |
|  | Electron-injection layer | 534(2) | 2 | CuPc | — |
|  |  | 534(1) | 0.1 | Li$_2$O | — |
|  | Electron-transport layer | 533 | 7.5 | Bphen | — |
|  | Light-emitting layer | 521 | 30 | 2mDBTBPDBq-II:PCBBiF:Ir(mpmppm)$_2$(acac) | 0.8:0.2:0.06 |
|  | Hole-transport layer | 532 | 10 | BPAFLP | — |
|  | Hole-injection layer | 531 | 15 | DBT3P-II:MoO$_3$ | 1:0.5 |
|  | Electrode | 501b | 65 | ITSO | — |
|  |  | 501a | 100 | Ag—Pd—Cu | — |

*1) The ratio of Ag:Mg is represented in volume ratio.

<1-1. Fabrication of Light-Emitting Element 5>

As a conductive layer 501a included in an electrode 501, an alloy film of silver, palladium, and copper (also referred to as an Ag—Pd—Cu film and APC) was formed over a substrate 510 to a thickness of 100 nm. Next, as a conductive layer 501b over and in contact with the conductive layer 501a, an ITSO film was formed to a thickness of 10 nm. The electrode 501 having a function of reflecting light was formed through the above steps. Note that the area of the electrode 501 was set to 4 mm$^2$ (2 mm×2 mm).

As the hole-injection layer 531, 4,4',4''-(benzene-1,3,5-triyl)tri(dibenzothiophen) (abbreviation: DBT3P-II) and molybdenum oxide (MoO$_3$) were deposited over the electrode 501 by co-evaporation in a weight ratio of DBT3P-II:MoO$_3$=1:0.5 to a thickness of 15 nm.

As a hole-transport layer 532, 4,4'-bis(9-carbazole)-2,2'-dimethylbiphenyl (abbreviation: dmCBP) was formed over the hole-injection layer 531 by evaporation to a thickness of 15 nm.

As a light-emitting layer 521, 3,5-bis[3-(9H-carbazol-9-yl)phenyl]pyridine (abbreviation: 35DCzPPy) and tris{2-[4-(2-adamantyl)-5-methyl-4H-1,2,4-triazol-3-yl-κN2]phenyl-κC}iridium(III) (abbreviation: Ir(Mptz-Adm2)$_3$) were deposited over the hole-transport layer 532 by co-evaporation in a weight ratio of 35DCzPPy:Ir(Mptz-Adm2)$_3$=1:0.06 to a thickness of 30 nm. Note that in the light-emitting layer

521, 35DCzPPy is a host material and Ir(Mptz-Adm2)$_3$ is a guest material (a phosphorescent material).

As an electron-transport layer 533, 35DCzPPy and bathophenanthroline (abbreviation: Bphen) were sequentially deposited over the light-emitting layer 521 by evaporation to thicknesses of 10 nm and 10 nm, respectively.

As an electron-injection layer 534, lithium oxide (Li$_2$O) and copper phthalocyanine (abbreviation: CuPc) were sequentially deposited over the electron-transport layer 533 by evaporation to thicknesses of 0.1 nm and 2 nm, respectively.

As a charge-generation layer 535 serving as the hole-injection layer, DBT3P-II and MoO$_3$ were deposited by co-evaporation in a weight ratio of DBT3P-II:MoO$_3$=1:0.5 to a thickness of 17.5 nm.

Then, as a hole-transport layer 537, 4-phenyl-4'-(9-phenylfluoren-9-yl)triphenylamine (abbreviation: BPAFLP) was deposited over the charge-generation layer 535 by evaporation to a thickness of 15 nm.

As the light-emitting layer 522, 2-[3'-(dibenzothiophen-4-yl)biphenyl-3-yl]dibenzo[f,h]quinoxaline (abbreviation: 2mDBTBPDBq-II), N-(1,1'-biphenyl-4-yl)-N-[4-(9-phenyl-911-carbazol-3-yl)phenyl]-9,9-dimethyl-9H-fluor en-2-amine (abbreviation: PCBBiF), and (acetylacetonato)bis[5-methyl-6-(2-methylphenyl)-4-phenylpyrimidinato]iridium (III) (abbreviation: Ir(mpmppm)$_2$(acac)) were deposited over the hole-transport layer 537 by co-evaporation in a weight ratio of 2mDBTBPDBq-II:PCBBiF:Ir(mpmppm)$_2$(acac)=0.8:0.2:0.06 to a thickness of 40 nm. Note that in the light-emitting layer 522, 2mDBTBPDBq-II is a host material, PCBBiF is an assist material, and Ir(mpmppm)$_2$(acac) is a guest material (a phosphorescent material).

As an electron-transport layer 538, 2mDBTBPDBq-II and Bphen were sequentially deposited over the light-emitting layer 522 by evaporation to a thickness of 15 nm and 20 nm, respectively. As an electron-injection layer 539, lithium fluoride (LiF) was deposited over the electron-transport layer 538 by evaporation to a thickness of 1 nm.

As an electrode 502, silver (Ag) and magnesium (Mg) were deposited over the electron-injection layer 539 by co-evaporation in a volume ratio of Ag:Mg=1:0.1 to a thickness of 15 nm, and then, an ITO film was formed to a thickness of 70 nm.

Through the above steps, the electrode 502 having a function of reflecting light and a function of transmitting light was formed. Through the above steps, the pair of electrodes and the EL layer were formed over the substrate 510. Note that in the above film formation process, the evaporation was performed by a resistance-heating method. The ITO film in the electrode 502 was formed by a sputtering method.

As an optical element 514, a blue (Blue) color filter was provided for a sealing substrate 512 of Light-emitting element 5.

Next, Light-emitting element 5 was sealed by fixing the sealing substrate 512 to the substrate 510 using a sealant for an organic EL device in a glove box containing a nitrogen atmosphere. Specifically, the sealant was applied to surround the EL layer formed over the substrate 510, the substrate 510 and the sealing substrate 512 were bonded to each other, irradiation with ultraviolet light having a wavelength of 365 nm at 6 J/cm$^2$ was performed, and heat treatment was performed at 80° C. for one hour. Through the above steps, Light-emitting element 5 was obtained.

<1-2. Fabrication of Light-Emitting Element 6>

Light-emitting element 6 was fabricated through the same steps as those for the above-described Light-emitting element 5 except steps for forming the conductive layer 501*b* and the hole-injection layer 531.

As the conductive layer 501*b* over and in contact with the conductive layer 501*a* which is included in the electrode 501, an ITSO film was formed to a thickness of 85 nm.

As the hole-injection layer 531 over the electrode 501, DBT3P-II and MoO$_3$ were deposited by co-evaporation in a weight ratio of DBT3P-II:MoO$_3$=1:0.5 to a thickness of 47.5 nm.

<1-3. Fabrication of Light-Emitting Element 7>

Light-emitting element 7 was different from Light-emitting elements 5 and 6 described above in steps of forming the electrode 501 to the electron-transport layer 538. For the other steps of Light-emitting element 7, the steps of Light-emitting elements 5 and 6 were referred to.

As the conductive layer 501*a* included in the electrode 501, an Ag—Pd—Cu film was formed over the substrate 510 to a thickness of 100 nm. Next, as the conductive layer 501*b* over and in contact with the conductive layer 501*a*, an ITSO film was formed to a thickness of 65 nm. Through the above steps, the electrode 501 having a function of reflecting light was formed. Note that the area of the electrode 501 was set to 4 mm$^2$ (2 mm×2 mm).

As the hole-injection layer 531, DBT3P-II and MoO$_3$ were deposited over the electrode 501 by co-evaporation in a weight ratio of DBT3P-II:MoO$_3$=1:0.5 to a thickness of 15 nm.

As a hole-transport layer 532, BPAFLP was deposited over the hole-injection layer 531 by evaporation to a thickness of 10 nm.

As a light-emitting layer 521, 2mDBTBPDBq-II, PCBBiF, and Ir(mpmppm)$_2$(acac) were deposited over the hole-transport layer 532 by co-evaporation in a weight ratio of 2mDBTBPDBq-II:PCBBiF:Ir(mpmppm)$_2$(acac)=0.8:0.2:0.06 to a thickness of 30 nm. Note that in the light-emitting layer 521, 2mDBTBPDBq-II is as a host material, PCBBiF is an assist material, and Ir(mpmppm)$_2$(acac) is a guest material (a phosphorescent material).

As electron-transport layer 533, Bphen was deposited by evaporation to a thickness of 7.5 nm over the light-emitting layer 521.

As the electron-injection layer 534, Li$_2$O and CuPc were deposited over the electron-transport layer 533 by evaporation to thicknesses of 0.1 nm and 2 nm, respectively.

As the charge-generation layer 535 also serving as a hole-injection layer, DBT3P-II and MoO$_3$ were deposited by co-evaporation in a weight ratio of DBT3P-II:MoO$_3$=1:0.5 to a thickness of 7.5 nm.

As the hole-transport layer 537, dmCBP was deposited over the charge-generation layer 535 by evaporation to a thickness of 10 nm.

As the light-emitting layer 522, 35DCzPPy and Ir(Mptz-Adm2)$_3$ were deposited over the hole-transport layer 537 by co-evaporation in a weight ratio of 35DCzPPy:Ir(Mptz-Adm2)$_3$=1:0.06 to a thickness of 30 nm. Note that in the light-emitting layer 522, 35DCzPPy is a host material and Ir(Mptz-Adm2)$_3$ is a guest material (a phosphorescent material).

As the electron-transport layer 538, 1,3,5-tri[3-(3-pyridyl)phenyl]benzene (abbreviation: TmPyPB) was deposited over the light-emitting layer 522 by evaporation to a thickness of 10 nm.

<1-4. Characteristics of Light-Emitting Elements 5 to 7>

Figure 44:
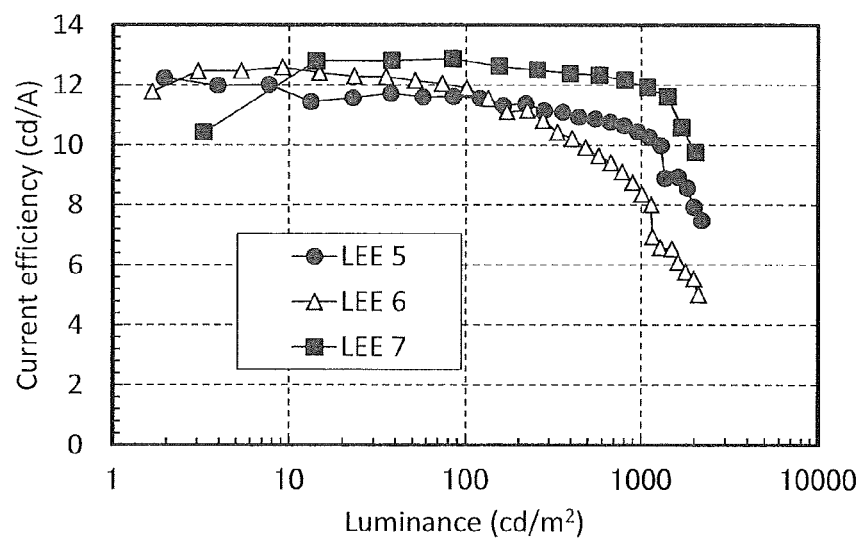
FIG. 44 is a graph showing current efficiency-luminance characteristics of light-emitting elements LEEs in Example.
Figure 45:
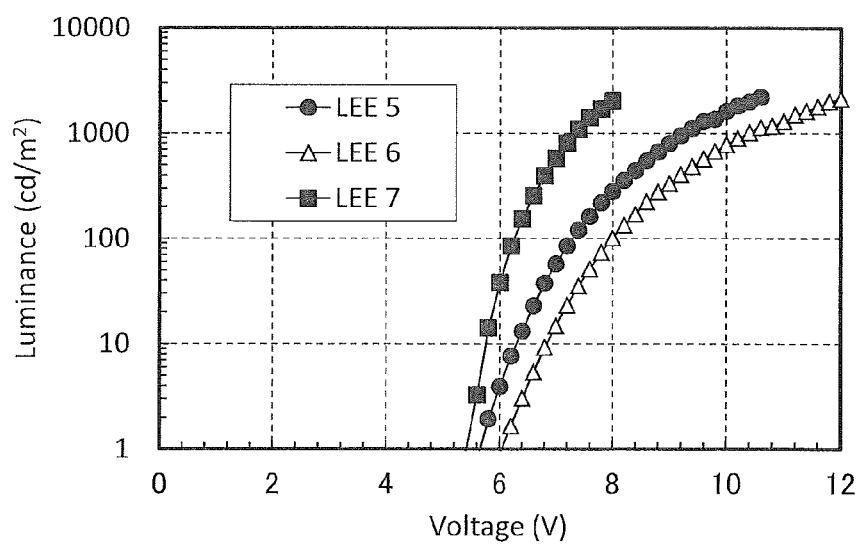
FIG. 45 is a graph showing luminance-voltage characteristics of light-emitting elements LEEs in Example.

Next, the current efficiency-luminance characteristics of the fabricated light-emitting elements 5 to 7 are shown in FIG. 44. Moreover, the luminance-voltage characteristics thereof are shown in FIG. 45. The measurements of the light-emitting elements were performed at room temperature (in an atmosphere kept at 23° C.).

Table 10 shows element characteristics of Light-emitting elements 5 to 7 at around 1000 cd/m$^2$.

TABLE 10

| | Voltage (V) | Current density (mA/cm$^2$) | CIE chromaticity coordinates (x, y) | Luminance (cd/m$^2$) | Current efficiency (cd/A) |
|---|---|---|---|---|---|
| Light-emitting element 5 | 92 | 9.1 | (0.14, 0.085) | 950 | 10 |
| Light-emitting element 6 | 10 | 12 | (0.15, 0.078) | 1000 | 8.4 |
| Light-emitting element 7 | 7.4 | 9.1 | (0.14, 0.091) | 1100 | 12 |

Figure 46:
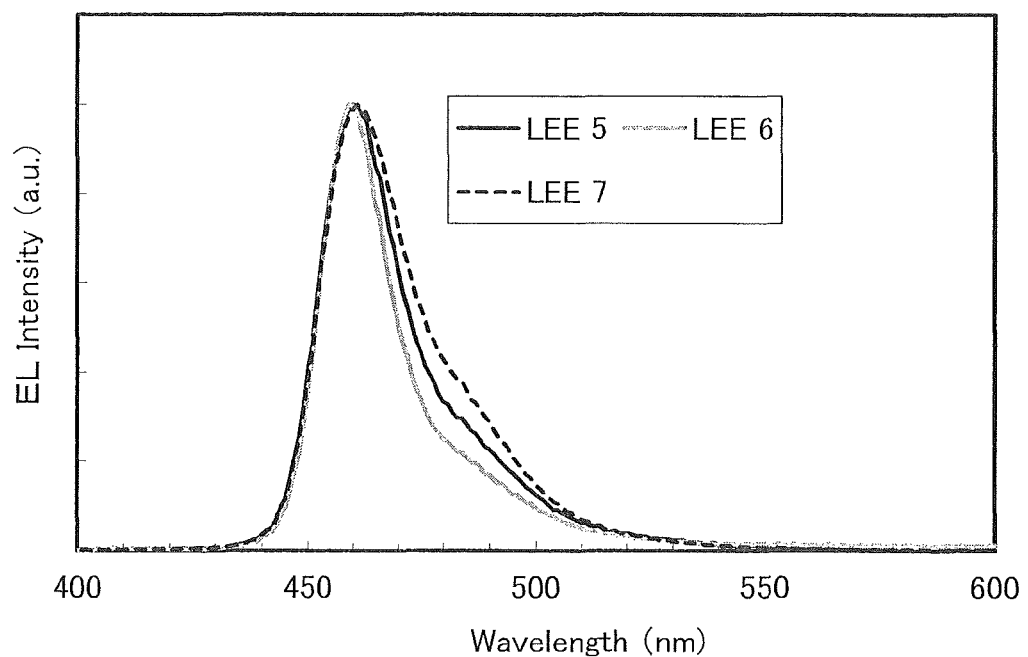
FIG. 46 is a graph showing emission spectra of light-emitting elements LEEs in Example.

FIG. 46 shows emission spectra (EL spectra) when a current at a current density of 2.5 mA/cm$^2$ was supplied to Light-emitting elements 5 to 7.

As shown in FIG. 44, FIG. 45, and Table 10, Light-emitting elements 5 to 7 emitted light at sufficiently low driving voltages. Furthermore, Light-emitting elements 5 to 7 emitted blue light with high color purity at a high current efficiency. Light-emitting element 6 emitted light of excellent blue whose chromaticity y is greater than 0.06 and less than or equal to 0.08 at a high current efficiency greater than or equal to 8 cd/A. Light-emitting elements 5 and 7 emitted favorable blue light the chromaticity y of which is greater than 0.08 and less than or equal to 0.1 at a high current efficiency greater than or equal to 10 cd/A.

Accordingly, it was found that a light-emitting element using Ir(Mptz-Adm2)$_3$ as a guest material, in other words, a light-emitting element using the guest material described in Embodiment 1, which has a function of converting the triplet excitation energy into light emission and the emission spectrum of which in a dichloromethane solution has a peak in a wavelength region ranging from 440 nm to 470 nm and has a full width at half maximum of greater than or equal to 20 nm and less than or equal to 80 nm, is suitable as a light-emitting element emitting blue light. Alternatively, a light-emitting element using a guest material whose light intensity at a wavelength of 530 nm is greater than or equal to 0% and less than or equal to 50% of the maximum light intensity, or a guest material whose chromaticity y in the CIE 1931 chromaticity coordinates, which is calculated from the emission spectrum, is greater than or equal to 0.01 and less than or equal to 0.3 is suitable as a light-emitting element emitting blue light.

As described above, with a component of one embodiment of the present invention, a light-emitting element which has high current efficiency and emits blue light with high color purity was able to be fabricated.

The structures described in Example 1 can be combined as appropriate with any of the structures described in the other examples and the embodiments.

Example 2

In Example 2, examples of fabricating light-emitting elements (Light-emitting elements 8 to 11) are described. The schematic cross-sectional views of FIGS. 1A and 1B can be referred to for cross sections of the light-emitting elements fabricated in Example 2. Table 11 shows the detailed structures of the elements. In addition, structures and abbreviations of compounds used here are given below.

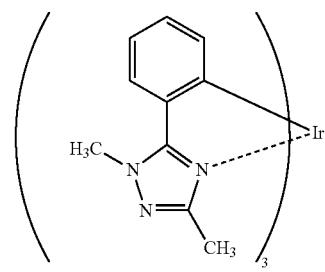

Ir(Mptz1-Me)$_3$

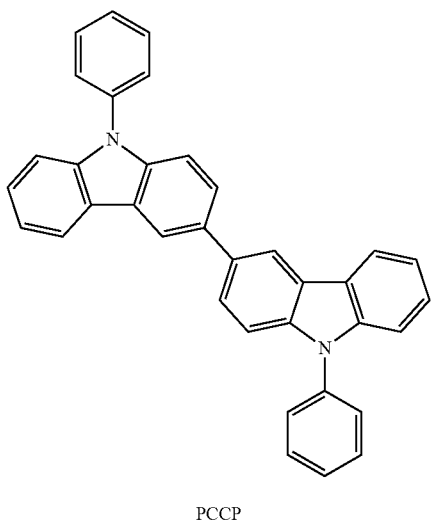

PCCP

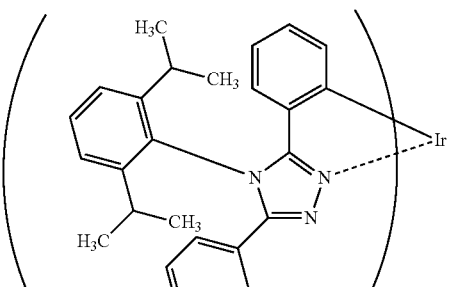

Ir(mpptz-diPrp)$_3$

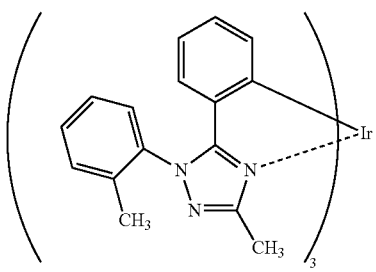

Ir(Mptz1-mp)$_3$

TABLE 11

| | Layer | Reference numeral | Thickness (nm) | Material | Weight ratio |
|---|---|---|---|---|---|
| Light-emitting element 8 | Electrode | 102 | 200 | Al | — |
| | Electron-injection layer | 119 | 1 | LiF | — |
| | Electron-transport layer | 118(2) | 15 | Bphen | — |
| | | 118(1) | 10 | 35DCzPPy | — |
| | Light-emitting layer | 130 | 30 | 35DCzPPy:Ir(Mptz-Adm2)$_3$ | 1:0.06 |
| | Hole-transport layer | 112 | 20 | dmCBP | — |
| | Hole-injection layer | 111 | 25 | DBT3P-II:MoO$_3$ | 1:0.5 |
| | Electrode | 101 | 70 | ITSO | — |
| Light-emitting element 9 | Electrode | 102 | 200 | Al | — |
| | Electron-injection layer | 119 | 1 | LiF | — |
| | Electron-transport layer | 118(2) | 15 | Bphen | — |
| | | 118(1) | 10 | 35DCzPPy | — |
| | Light-emitting layer | 130 | 30 | 35DCzPPy:Ir(Mptz1-Me)$_3$ | 1:0.06 |
| | Hole-transport layer | 112 | 20 | dmCBP | — |
| | Hole-injection layer | 111 | 15 | DBT3P-II:MoO$_3$ | 1:0.5 |
| | Electrode | 101 | 70 | ITSO | — |
| Light-emitting element 10 | Electrode | 102 | 200 | Al | — |
| | Electron-injection layer | 119 | 1 | LiF | — |
| | Electron-transport layer | 118(2) | 15 | Bphen | — |
| | | 118(1) | 10 | 35DCzPPy | — |
| | Light-emitting layer | 130(2) | 10 | 35DCzPPy:Ir(mpptz-diPrp)$_3$ | 1:0.06 |
| | | 130(1) | 20 | 35DCzPPy:PCCP:Ir(mpptz-diPrp)$_3$ | 0.3:1:0.06 |
| | Hole-transport layer | 112 | 20 | PCCP | — |
| | Hole-injection layer | 111 | 20 | DBT3P-II:MoO$_3$ | 1:0.5 |
| | Electrode | 101 | 70 | ITSO | — |
| Light-emitting element 11 | Electrode | 102 | 200 | Al | — |
| | Electron-injection layer | 119 | 1 | LiF | — |
| | Electron-transport layer | 118(2) | 15 | Bphen | — |
| | | 118(1) | 10 | 35DCzPPy | — |
| | Light-emitting layer | 130(2) | 10 | 35DCzPPy:Ir(Mptz1-mp)$_3$ | 1:0.06 |
| | | 130(1) | 20 | 35DCzPPy:PCCP:Ir(Mptz1-mp)$_3$ | 0.8:0.2:0.05 |
| | Hole-transport layer | 112 | 20 | PCCP:Ir(Mptz1-mp)$_3$ | 0.8:0.2 |
| | Hole-injection layer | 111 | 20 | DBT3P-II:MoO$_3$ | 1:0.5 |
| | Electrode | 101 | 70 | ITSO | — |

<2-1. Fabrication of Light-Emitting Element 8>

As the electrode 101 having a function of transmitting light, a 70 nm thick ITSO film was formed. The electrode area of the electrode 101 was set to 4 mm$^2$ (2 mm×2 mm).

As the hole-injection layer 111, DBT3P-II and MoO$_3$ were deposited over the electrode 101 by co-evaporation in a weight ratio of DBT3P-II:MoO$_3$=1:0.5 to a thickness of 25 nm.

As the hole-transport layer 112, dmCBP was deposited over the hole-injection layer 111 by evaporation to a thickness of 20 nm.

As the light-emitting layer 130, 35DCzPPy and Ir(Mptz-Adm2)$_3$ were deposited over the hole-transport layer 112 by co-evaporation in a weight ratio of 35DCzPPy:Ir(Mptz-Adm2)$_3$=1:0.06 to a thickness of 30 nm Note that in the light-emitting layer 130, 35DCzPPy is a host material and Ir(Mptz-Adm2)$_3$ is a guest material (a phosphorescent material).

As the electron-transport layer 118, 35DCzPPy and Bphen were sequentially deposited over the light-emitting layer 130 by evaporation to a thickness of 10 nm and 15 nm, respectively. Then, as the electron-injection layer 119, LiF was deposited over the electron-transport layer 118 by evaporation to a thickness of 1 nm.

As the electrode 102, aluminum (Al) was deposited over the electron-injection layer 119 to a thickness of 200 nm.

Next, in a glove box containing a nitrogen atmosphere, Light-emitting element 8 was sealed by fixing a sealing substrate to the substrate provided with the EL layer using a sealant for an organic EL device. Specifically, the sealant was applied to surround the EL layer, the substrate provided with the EL layer was bonded to the sealing substrate, and irradiation with ultraviolet light having a wavelength of 365 nm at 6 J/cm$^2$ and heat treatment at 80° C. for one hour were performed. Through the above steps, Light-emitting element 8 was obtained.

<2-2. Fabrication of Light-Emitting Element 9>

Light-emitting element 9 was fabricated through the same steps as those for the above-described Light-emitting element 8 except steps for forming the hole-injection layer 111 and the light-emitting layer 130.

As the hole-injection layer 111 over the electrode 101, DBT3P-II and MoO$_3$ were deposited by co-evaporation in a weight ratio of DBT3P-II:MoO$_3$=1:0.5 to a thickness of 15 nm.

As the light-emitting layer 130, 35DCzPPy and tris(1,3-dimethyl-5-phenyl-1H-1,2,4-triazolato)iridium(III) (abbreviation: Ir(Mptz1-Me)$_3$) were deposited over the hole-transport layer 112 by co-evaporation in a weight ratio of 35DCzPPy:Ir(Mptz1-Me)$_3$=1:0.06 to a thickness of 30 nm. Note that in the light-emitting layer 130, 35DCzPPy is a host material and Ir(Mptz1-Me)$_3$ is a guest material (a phosphorescent material).

<2-3. Fabrication of Light-Emitting Element 10>

Light-emitting element 10 was fabricated through the same steps as those for the above-described Light-emitting element 8 except steps for forming the hole-injection layer 111 to the light-emitting layer 130.

As the hole-injection layer 111 over the electrode 101, DBT3P-II and MoO$_3$ were deposited by co-evaporation in a weight ratio of DBT3P-II:MoO$_3$=1:0.5 to a thickness of 20 nm.

As the hole-transport layer 112, 9-phenyl-9H-3-(9-phenyl-9H-carbazol-3-yl)carbazole (abbreviation: PCCP) was deposited over the hole-injection layer 111 by evaporation to a thickness of 20 nm.

As the light-emitting layer 130, 35DCzPPy, PCCP, and tris{2-[5-(2-methylphenyl)-4-(2,6-diisopropylphenyl)-4H-1,2,4-triazol-3-yl-κN2]phenyl-κC}iridium(III) (abbreviation: Ir(mpptz-diPrp)$_3$) were deposited over the hole-transport layer 112 by co-evaporation in a weight ratio of 35DCzPPy:PCCP:Ir(mpptz-diPrp)$_3$=0.3:1:0.06 to a thickness of 20 nm, and successively, 35DCzPPy and Ir(mpptz-diPrp)$_3$ were deposited by co-evaporation in a weight ratio of 35DCzPPy:Ir(mpptz-diPrp)$_3$=1:0.06 to a thickness of 10 nm. Note that in the light-emitting layer 130, 35DCzPPy is a host material, PCCP is an assist material, and Ir(mpptz-diPrp)$_3$ is a guest material (a phosphorescent material).

<2-4. Fabrication of Light-Emitting Element 11>

Light-emitting element 11 was fabricated through the same steps as those for the above-described Light-emitting element 8 except steps for forming the hole-injection layer 111 to the light-emitting layer 130.

As the hole-injection layer 111 over the electrode 101, DBT3P-II and MoO$_3$ were deposited by co-evaporation in a weight ratio of DBT3P-II:MoO$_3$=1:0.5 to a thickness of 20 nm.

As the hole-transport layer 112, PCCP and tris[3-methyl-1-(2-methylphenyl)-5-phenyl-1H-1,2,4-triazolato]iridium (III) (abbreviation: Ir(Mptz1-mp)$_3$) were deposited over the hole-injection layer 111 by co-evaporation in a weight ratio of PCCP:Ir(Mptz1-mp)$_3$=0.8:0.2 to a thickness of 20 nm.

As the light-emitting layer 130, 35DCzPPy, PCCP, and Ir(Mptz1-mp)$_3$ were deposited over the hole-transport layer 112 by co-evaporation in a weight ratio of 35DCzPPy:PCCP:Ir(Mptz1-mp)$_3$=0.8:0.2:0.05 to a thickness of 20 nm, and successively, 35DCzPPy and Ir(Mptz1-mp)$_3$ were deposited by co-evaporation in a weight ratio of 35DCzPPy:Ir(Mptz1-mp)$_3$=1:0.06 to a thickness of 10 nm. Note that in the light-emitting layer 130, 35DCzPPy is a host material, PCCP is an assist material, and Ir(Mptz1-mp)$_3$ is a guest material (a phosphorescent material).

<2-5. Characteristics of Light-Emitting Elements 8 to 11>

Figure 47:
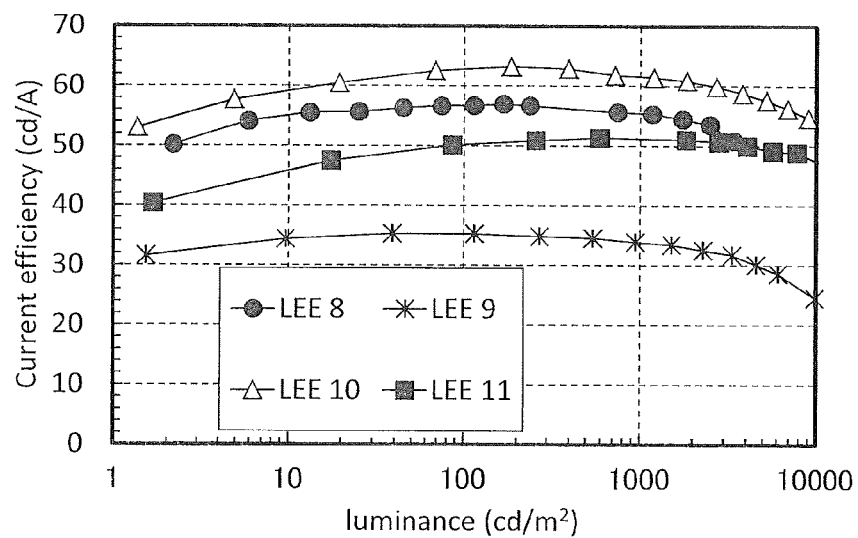
FIG. 47 is a graph showing current efficiency-luminance characteristics of light-emitting elements LEEs in Example.
Figure 48:
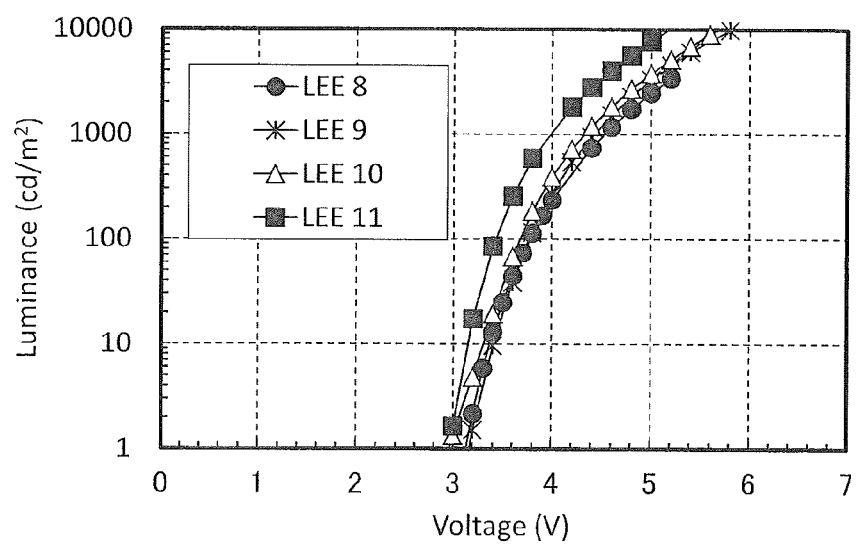
FIG. 48 is a graph showing luminance-voltage characteristics of light-emitting elements LEEs in Example.
Figure 49:
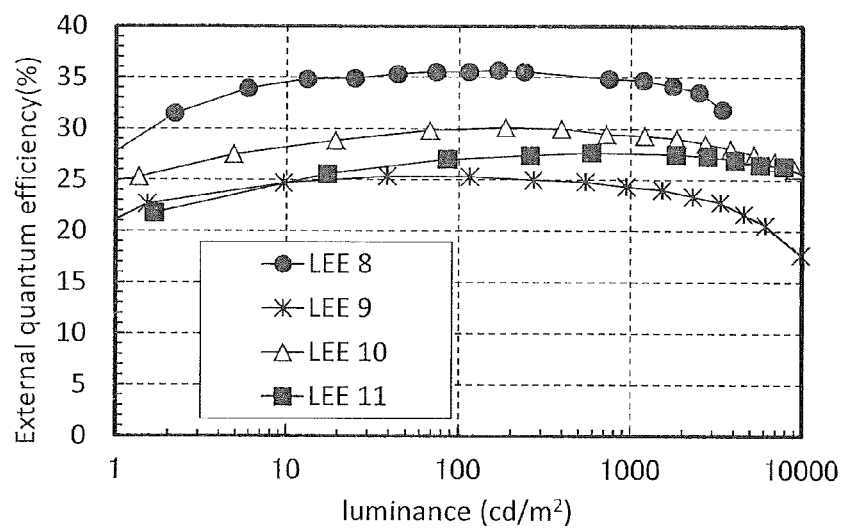
FIG. 49 is a graph showing external quantum efficiency-luminance characteristics of light-emitting elements LEEs in Example.

Next, the current efficiency-luminance characteristics of the fabricated Light-emitting elements 8 to 11 are shown in FIG. 47. Moreover, the luminance-voltage characteristics thereof are shown in FIG. 48. The external quantum efficiency-luminance characteristics are shown in FIG. 49. The measurements of the light-emitting elements were performed at room temperature (in an atmosphere kept at 23° C.).

Table 12 shows element characteristics of Light-emitting elements 8 to 11 at around 1000 cd/m$^2$.

TABLE 12

| | Voltage (V) | Current density (mA/cm$^2$) | CIE chromaticity coordinates (x, y) | Luminance (cd/m$^2$) | Current efficiency (cd/A) | External quantum efficiency (%) |
|---|---|---|---|---|---|---|
| Light-emitting element 8 | 4.6 | 2.1 | (0.15, 0.22) | 1200 | 55 | 35 |
| Light-emitting element 9 | 4.4 | 2.8 | (0.15, 0.18) | 940 | 34 | 24 |
| Light-emitting element 10 | 4.4 | 1.9 | (0.17, 0.39) | 1200 | 61 | 29 |
| Light-emitting element 11 | 4.0 | 2.2 | (0.16, 0.32) | 1100 | 51 | 28 |

Figure 50:
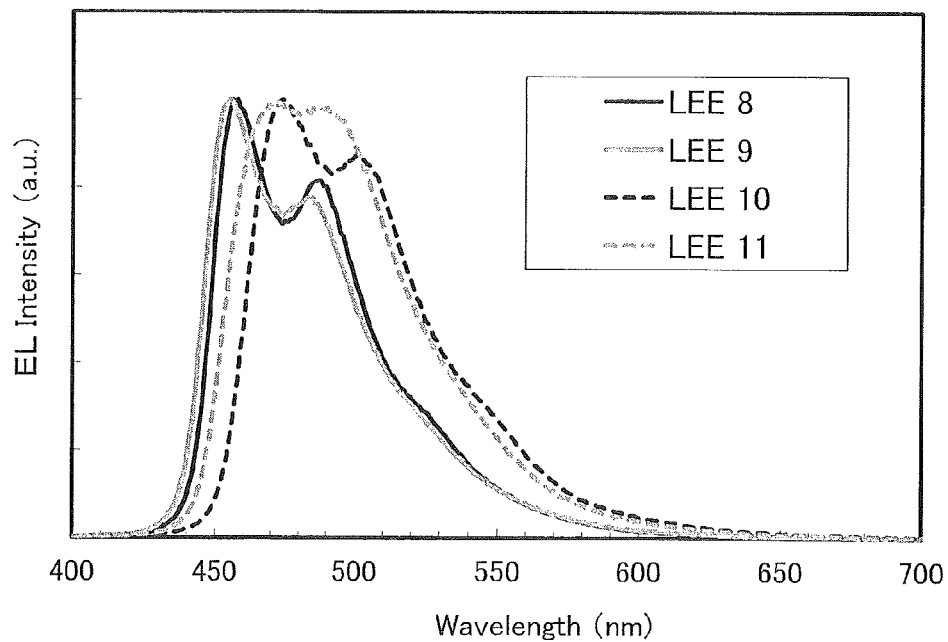
FIG. 50 is a graph showing emission spectra of light-emitting elements LEEs in Example.

FIG. 50 shows electroluminescence (EL) spectra when a current at a current density of 2.5 mA/cm$^2$ was supplied to Light-emitting elements 8 to 11. Table 13 shows wavelengths and full widths at half maximum of the peaks of the emission spectra shown in FIG. 50.

TABLE 13

| | Wavelength of the emission spectrum peak (nm) | Full width at half maximum (nm) |
|---|---|---|
| Light-emitting element 8 | 458 | 57 |
| Light-emitting element 9 | 455 | 57 |
| Light-emitting element 10 | 474 | 64 |
| Light-emitting element 11 | 472 | 70 |

As shown in FIG. 50, Table 12, and Table 13, the emission spectrum of each of Light-emitting elements 8 and 9 has a peak in a wavelength region ranging from 440 nm to 470 nm and a full width at half maximum of greater than or equal to 20 nm and less than or equal to 80 nm. Therefore, each of Light-emitting elements 8 and 9 had a chromaticity with which favorable blue light was emitted. In each of Light-emitting elements 8 and 9, the light intensity at a wavelength of 530 nm was greater than or equal to 0% and less than or equal to 50% of the maximum light intensity; and the chromaticity y in the CIE 1931 chromaticity coordinates, which was calculated from the emission spectrum, was greater than or equal to 0.01 and less than or equal to 0.3.

In contrast, the emission spectrum of each of Light-emitting elements 10 and 11 had a peak in a wavelength longer than 470 nm; thus, each of Light-emitting elements 10 and 11 had a chromaticity y greater than 0.3 with which light blue light was emitted.

Accordingly, when the guest material that can be used in the light-emitting element of one embodiment of the present invention is used in a light-emitting element that includes a first electrode having a function of reflecting light and a second electrode having a function of transmitting light, the light-emitting element shows an emission spectrum similar to that in a dichloromethane solution, as in Light-emitting elements 8 and 9. Therefore, the guest material that can be used in the light-emitting element of one embodiment of the present invention is a material whose emission spectrum has a peak in a wavelength region ranging from 440 nm to 470 nm and has a full width at half maximum of greater than or equal to 20 nm and less than or equal to 80 nm when the material is used in a light-emitting element that includes a first electrode having a function of reflecting light and a second electrode having a function of transmitting light.

Alternatively, the guest material that can be used in the light-emitting element of one embodiment of the present invention is a material whose light intensity at a wavelength of 530 nm is greater than or equal to 0% and less than or equal to 50% of the maximum light intensity or a material whose chromaticity y (the CIE 1931 chromaticity coordinates) is greater than or equal to 0.01 and less than or equal to 0.3 when the material is used in a light-emitting element that includes a first electrode having a function of reflecting light and a second electrode having a function of transmitting light.

As shown in FIGS. 47 to 49 and Table 12, Light-emitting elements 8 to 11 emitted light at sufficiently low driving voltages. Moreover, Light-emitting elements 8 and 9 showed high current efficiency and high external quantum efficiency exceeding 20% while emitted blue light with high color purity. In particular, Light-emitting element 8 showed an extremely high external quantum efficiency exceeding 30%.

Consequently, with use of Ir(Mptz-Adm2)$_3$ or Ir(Mptz1-Me)$_3$, which were used in this example, as the guest material, a light-emitting element emitting blue light with high emission efficiency and high color purity can be fabricated.

As described above, with use of the guest material that can be used for one embodiment of the present invention, a light-emitting element emitting blue light with high color purity at a high current efficiency can be fabricated.

The structures described in Example 2 can be combined as appropriate with any of the structures described in the other examples and the embodiments.

This application is based on Japanese Patent Application serial no. 2014-264945 filed with Japan Patent Office on Dec. 26, 2014, the entire contents of which are hereby incorporated by reference.

What is claimed is:

1. A light-emitting element comprising:
a first electrode;
a second electrode; and
an EL layer,
wherein the first electrode is configured to reflect light,
wherein the second electrode is configured to reflect light and transmit light,
wherein the EL layer is between the first electrode and the second electrode,
wherein the EL layer includes a first guest material,
wherein the first guest material is configured to convert triplet excitation energy into light emission, and
wherein an emission spectrum of the first guest material in a dichloromethane solution has a maximum value in a wavelength region ranging from 440 nm to 470 nm and has a full width at half maximum of greater than or equal to 20 nm and less than or equal to 80 nm.

2. The light-emitting element according to claim 1, wherein light intensity of the first guest material in the dichloromethane solution at a wavelength of 530 nm is greater than or equal to 0% and less than or equal to 50% of the maximum value.

3. The light-emitting element according to claim 1,
wherein an chromaticity y in CIE 1931 chromaticity coordinates of the first guest material is greater than or equal to 0.01 and less than or equal to 0.3, and
wherein the chromaticity y is calculated from the emission spectrum of the first guest material in the dichloromethane solution.

4. The light-emitting element according to claim 1, wherein the light-emitting element emits light whose chromaticity yin CIE 1931 chromaticity coordinates is greater than or equal to 0.01 and less than or equal to 0.06 at a current efficiency greater than or equal to 3 cd/A.

5. The light-emitting element according to claim 1, wherein the light-emitting element emits light whose chromaticity y in CIE 1931 chromaticity coordinates is greater than 0.06 and less than or equal to 0.08 at a current efficiency greater than or equal to 8 cd/A.

6. The light-emitting element according to claim 1, wherein the light-emitting element emits light whose chromaticity y in CIE 1931 chromaticity coordinates is greater than 0.08 and less than or equal to 0.1 at a current efficiency greater than or equal to 10 cd/A.

7. The light-emitting element according to claim 1, wherein the first guest material includes iridium.

8. The light-emitting element according to claim 1, wherein the first guest material includes iridium.

9. The light-emitting element according to claim 8,
wherein the first guest material includes a ligand coordinated to the iridium, and
wherein the ligand includes a nitrogen-containing five-membered heterocyclic skeleton.

10. The light-emitting element according to claim 9, wherein the nitrogen-containing five-membered heterocyclic skeleton is an imidazole skeleton or a triazole skeleton.

11. The light-emitting element according to claim 1,
wherein the first electrode includes at least one of Al and Ag, and
wherein the second electrode includes at least one of Mg and Ag.

12. A display device comprising:
the light-emitting element according to claim 1; and
at least one of a color filter and a transistor.

13. An electronic device comprising:
the display device according to claim 12; and
at least one of a housing and a touch sensor.

14. A light-emitting element comprising:
a first electrode;
a second electrode;
a first EL layer;
a second EL layer; and
a charge-generation layer,
wherein the first electrode is configured to reflect light,
wherein the second electrode is configured to reflect light and transmit light,
wherein the first EL layer, the second EL layer, and the charge-generation layer are between the first electrode and the second electrode,
wherein the first EL layer includes a first guest material,
wherein the first guest material is configured to convert triplet excitation energy into light emission, and
wherein an emission spectrum of the first guest material in a dichloromethane solution has a maximum value in a wavelength region ranging from 440 nm to 470 nm and has a full width at half maximum of greater than or equal to 20 nm and less than or equal to 80 nm.

15. The light-emitting element according to claim 14,
wherein the second EL layer includes a second guest material, and
wherein the emission spectrum of the second guest material has a maximum value in any one of a green wavelength region, a yellow-green wavelength region, a yellow wavelength region, an orange wavelength region, and a red wavelength region.

16. The light-emitting element according to claim 15, wherein the second guest material is configured to convert triplet excitation energy into light emission.

17. The light-emitting element according to claim 14, wherein the first guest material includes iridium.

18. The light-emitting element according to claim 14,
wherein the first guest material includes a ligand coordinated to the iridium, and wherein the ligand includes a nitrogen-containing five-membered heterocyclic skeleton.

19. A display device comprising:
the light-emitting element according to claim 14; and
at least one of a color filter and a transistor.

20. An electronic device comprising:
the display device according to claim 19; and
at least one of a housing and a touch sensor.

* * * * *